United States Patent
Maechling et al.

(10) Patent No.: US 9,204,646 B2
(45) Date of Patent: *Dec. 8, 2015

(54) PYRAZOLE TETRAHYDRONAPHTHYL CARBOXAMIDES

(71) Applicant: BAYER CROPSCIENCE AG, Monheim (DE)

(72) Inventors: Simon Maechling, Lyons (FR); Mazen Es-Sayed, Langenfeld (DE); Peter Dahmen, Neuss (DE); Ulrike Wachendorff-Neumann, Neuwied (DE); David Bernier, Lyons (FR); Lionel Carles, Tramoyes (FR); Christophe Dubost, Charbonnieres les bains (FR); Jean-Pierre Vors, Sainte Foy les Lyon (FR); Stephane Brunet, St Andre de Corcy (FR); Helene Lachaise, Lyons (FR)

(73) Assignee: BAYER CROPSCIENCE AG, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/399,544

(22) PCT Filed: May 6, 2013

(86) PCT No.: PCT/EP2013/059414
§ 371 (c)(1),
(2) Date: Nov. 7, 2014

(87) PCT Pub. No.: WO2013/167548
PCT Pub. Date: Nov. 14, 2013

(65) Prior Publication Data
US 2015/0119242 A1  Apr. 30, 2015

(30) Foreign Application Priority Data

May 9, 2012 (EP) .................................... 12167286
Dec. 16, 2012 (EP) .................................... 12197383

(51) Int. Cl.
| | |
|---|---|
| A01N 43/56 | (2006.01) |
| C07D 231/14 | (2006.01) |
| C07D 231/16 | (2006.01) |
| C07C 211/60 | (2006.01) |
| C07C 251/50 | (2006.01) |

(52) U.S. Cl.
CPC .............. *A01N 43/56* (2013.01); *C07C 211/60* (2013.01); *C07C 251/50* (2013.01); *C07D 231/14* (2013.01); *C07D 231/16* (2013.01)

(58) Field of Classification Search
None
See application file for complete search history.

(56) References Cited

U.S. PATENT DOCUMENTS

| | | | |
|---|---|---|---|
| 4,837,242 A * | 6/1989 | Ohsumi et al. | ............... 514/365 |
| 7,687,531 B2 | 3/2010 | Dunkel et al. | |
| 7,906,656 B2 | 3/2011 | Dunkel et al. | |
| 8,119,682 B2 | 2/2012 | Dunkel et al. | |
| 2008/0045546 A1 | 2/2008 | Bouchon et al. | |

FOREIGN PATENT DOCUMENTS

| | | |
|---|---|---|
| EP | 0199822 A | 11/1986 |
| EP | 0276177 A1 | 7/1988 |
| EP | 1400516 A1 | 3/2004 |
| JP | 62096472 A | 5/1987 |
| JP | 01313402 A | 12/1989 |
| JP | 05310512 A | 11/1993 |
| WO | 9212970 A1 | 8/1992 |
| WO | 02059086 A1 | 8/2002 |
| WO | 2004035589 A1 | 4/2004 |
| WO | 2004103975 A1 | 12/2004 |
| WO | 2005040100 A1 | 5/2005 |

OTHER PUBLICATIONS

Patani et al. (Chem. Rev. 1996, 3147-3176).*
International Search Report from Corresponding PCT/EP2013/059414, mailed Jun. 13, 2013.
Kurita et al., Efficient and Convenient Heterogeneous Palladium-Catalyzed Regioselective Deuteration at the Benzylic Position Chemistry—A European Journal, vol. 14, No. 2., Jan. 7, 2008, pp. 664-673, XP055065491.
Barker et al., "Dissociated Nonsteroidal Glucocorticoid Receptor Modulators; Discovery of the Agonist Trigger in a Tetrahydronaphthalene-Benzoxazine Series" Journal of Medicinal Chemistry, vol. 49, No. 14, Jul. 1, 2006, pp. 4216-4231, XP055065568.
Spiteller, Reduktionsprodukte des 8-Nitronaphthaldehydes-(1), Monatshefte Fur Chemie. Springer Verlag Wien. AT, vol. 90, No. 5, Jan. 1, 1959, pp. 721-728, XP007921962.
Erickson et al., "Hydrogen Bond Donor Properties of the Difluoromethyl Group", J. Org. Chem., 1995, 60, pp. 1626-1631.

* cited by examiner

*Primary Examiner* — Kamal Saeed
(74) *Attorney, Agent, or Firm* — Miles & Stockbridge PC

(57) ABSTRACT

The present invention relates to novel pyrazole(thio)tetrahydronaphthyl carboxamides, to processes for preparing these compounds, to compositions comprising these compounds, and to the use thereof as biologically active compounds, especially for control of harmful microorganisms in crop protection and in the protection of materials.

17 Claims, No Drawings

PYRAZOLE TETRAHYDRONAPHTHYL CARBOXAMIDES

CROSS REFERENCE TO RELATED APPLICATIONS

This application is a §371 National Stage Application of PCT/EP2013/059414, filed May 6, 2013, which claims priority to EP 12167286.9, filed May 9, 2012 and to EP 12197383.8, filed Dec. 1, 2012.

BACKGROUND

1. Field of the Invention

The present invention relates to novel pyrazole(thio)tetrahydronaphthyl carboxamides, to processes for preparing these compounds, to compositions comprising these compounds, and to the use thereof as biologically active compounds, especially for control of harmful microorganisms in crop protection and in the protection of materials.

2. Description of Related Art

It is already known that certain pyrazole tetrahydronaphthyl, but not tetrahydronaphthyl, carboxamides have fungicidal properties (e.g. WO 92/12970, EP-A 0 199 822, EP-A 0 276 177, JP-A 62-096472, JP-A 05-310512, JP-A 01-313402, WO 02/059086, WO 2004/103975 and *J. Org. Chem.* 1995, 60, 1626-1631).

Since the ecological and economic demands made on modern active ingredients, for example fungicides, are increasing constantly, for example with respect to activity spectrum, toxicity, selectivity, application rate, formation of residues and favourable manufacture, and there can also be problems, for example, with resistances, there is a constant need to develop novel fungicidal compositions which have advantages over the known compositions at least in some areas.

SUMMARY

This invention now provides novel 1-methyl-3-dihalogenomethyl-5-halogenopyrazole(thio)tetrahydronaphthyl carboxamides of the formula (I)

(I)

in which
Hal$^1$ represents chlorine or fluorine;
Hal$^2$ represents chlorine or fluorine;
T represents an oxygen or sulfur atom;
Q represents hydrogen, $C_1$-$C_6$-alkylsulfonyl, $C_1$-$C_4$-alkoxy-$C_1$-$C_4$-alkyl, $C_1$-$C_4$-haloalkylsulfonyl, halo-$C_1$-$C_4$-alkoxy-$C_1$-$C_4$-alkyl;
X represents halogen, nitro, cyano, $C_1$-$C_{12}$-alkyl; $C_1$-$C_6$-haloalkyl having 1 to 9 identical or different halogen atoms; $C_1$-$C_6$-alkoxy; $C_1$-$C_6$-haloalkoxy having 1 to 9 identical or different halogen atoms; $C_1$-$C_6$-alkylsulfanyl; $C_1$-$C_6$-haloalkylsulfanyl having 1 to 9 identical or different halogen atoms; $C_1$-$C_6$-alkylsulfonyl; $C_1$-$C_6$-haloalkylsulfonyl having 1 to 9 identical or different halogen atoms; $C_2$-$C_{12}$-alkenyl; $C_2$-$C_{12}$-alkynyl; $C_3$-$C_7$-cycloalkyl; phenyl; tri($C_1$-$C_8$)alkylsilyl; tri($C_1$-$C_8$)alkylsilyl-$C_1$-$C_8$-alkyl;
m represents 0, 1, 2 or 3
$R^1$, $R^2$, $R^3$, $R^4$, $R^5$, $R^6$, $R^7$ and $R^8$ independently one to another represent hydrogen; halogen; cyano; $C_1$-$C_{16}$-alkyl; $C_2$-$C_{16}$-haloalkyl having 1 to 9 identical or different halogen atoms; $C_3$-$C_8$-cycloalkyl; $C_3$-$C_7$-halocycloalkyl having 1 to 9 identical or different halogen atoms; $C_1$-$C_6$-haloalkyl having 1 to 9 identical or different halogen atoms; ($C_3$-$C_8$-cycloalkyl)-$C_1$-$C_8$-alkyl; ($C_3$-$C_8$-cycloalkyl)-$C_3$-$C_8$-cycloalkyl; $C_2$-$C_{16}$-alkenyl; $C_2$-$C_{16}$-alkynyl; $C_2$-$C_{16}$-alkenyl-$C_1$-$C_{16}$-alkyl; $C_2$-$C_{16}$-alkynyl-$C_1$-$C_{16}$-alkyl; $C_1$-$C_{16}$-alkoxy; $C_3$-$C_8$-cycloalkyloxy; ($C_3$-$C_8$-cycloalkyl)-$C_1$-$C_8$-alkyloxy; $C_1$-$C_8$-alkylsulfanyl; $C_3$-$C_8$-cycloalkylsulfanyl; ($C_3$-$C_8$-cycloalkyl)-$C_1$-$C_8$-alkylsulfanyl; $C_2$-$C_{16}$-alkenyloxy; $C_3$-$C_8$-alkynyloxy; aryl-$C_1$-$C_8$-alkyloxy which is optionally substituted by up to 6 identical or different groups $R^b$; aryl-$C_1$-$C_8$-alkylsulfanyl which is optionally substituted by up to 6 identical or different groups $R^b$; aryloxy which is optionally substituted by up to 6 identical or different groups $R^b$; arylsulfanyl which is optionally substituted by up to 6 identical or different groups $R^b$; ($C_3$-$C_8$-cycloalkyl)-$C_2$-$C_8$-alkenyl; ($C_3$-$C_8$-cycloalkyl)-$C_2$-$C_8$-alkynyl; tri($C_1$-$C_8$)alkylsilyl; tri($C_1$-$C_8$)alkylsilyl-$C_1$-$C_8$-alkyl; aryl-$C_1$-$C_8$-alkyl which is optionally substituted by up to 6 identical or different groups $R^b$; aryl-$C_2$-$C_8$-alkenyl which is optionally substituted by up to 6 identical or different groups $R^b$; aryl-$C_2$-$C_8$-alkynyl which is optionally substituted by up to 6 identical or different groups $R^b$; $C_1$-$C_8$-alkylamino; di-$C_1$-$C_8$-alkylamino; arylamino which is optionally substituted by up to 6 identical or different groups $R^b$; $C_1$-$C_8$-alkylcarbonyl; $C_1$-$C_8$-alkylcarbonyloxy; $C_1$-$C_8$-alkylcarbonylamino; $C_1$-$C_8$-alkoxycarbonyl; $C_1$-$C_8$-alkyloxycarbonyloxy; $C_1$-$C_8$-alkylcarbamoyl; di-$C_1$-$C_8$-alkylcarbamoyl; $C_1$-$C_8$-alkylaminocarbonyloxy; di-$C_1$-$C_8$-alkylaminocarbonyloxy; N—($C_1$-$C_8$-alkyl)hydroxycarbamoyl; $C_1$-$C_8$-alkoxycarbamoyl; N—($C_1$-$C_8$-alkyl)-$C_1$-$C_8$-alkoxycarbamoyl; aryl-$C_1$-$C_8$-alkylamino which is optionally substituted by up to 6 identical or different groups $R^b$; ($C_1$-$C_8$-alkoxyimino)-$C_1$-$C_8$-alkyl; ($C_2$-$C_8$-cycloalkoxyimino)-$C_1$-$C_8$-alkyl; $C_1$-$C_8$-alkyliminoxy; $C_1$-$C_8$-alkyliminoxy-$C_1$-$C_8$-alkyl; each of which is optionally substituted;
provided that $R^1$, $R^2$, $R^3$, $R^4$, $R^5$, $R^6$ and $R^7$ do not represent hydrogen at the same time when $R^8$ represents hydrogen or trifluoromethyl;
$R^1$ and $R^2$ can form together with the carbon to which they are attached a $C_3$-$C_8$-cycloalkyl; $C_3$-$C_8$-cycloalkenyl, or a saturated 5, 6 or 7 membered heterocycle; each of which is optionally substituted; or may represent a group =C(Y$^1$)Y$^2$ or a group =N—O—R$^c$;
$R^3$ and $R^4$ can form together with the carbon to which they are attached a $C_3$-$C_8$-cycloalkyl; $C_3$-$C_8$-cycloalkenyl, or a saturated 5, 6 or 7 membered heterocycle; each of which is optionally substituted; or may represent a group =C(Y$^1$)Y$^2$ or a group =N—O—R$^c$;
$R^5$ and $R^6$ can form together with the carbon to which they are attached a $C_3$-$C_8$-cycloalkyl; $C_3$-$C_8$-cycloalkenyl, or a saturated 5, 6 or 7 membered heterocycle; each of which is optionally substituted; or may represent a group =C(Y$^1$)Y$^2$ or a group =N—O—R$^c$;
$R^7$ and $R^8$ can form together with the carbon to which they are attached a $C_3$-$C_8$-cycloalkyl; $C_3$-$C_8$-cycloalkenyl, or a saturated 5, 6 or 7 membered heterocycle; each of which is optionally substituted; or may represent a group =C(Y$^1$)Y$^2$ or a group =N—O—R$^c$;

$R^1$ and $R^3$ or $R^3$ and $R^5$ or $R^5$ and $R^7$ can form with the carbons to which they are attached a $C_3$-$C_8$-cycloalkyl; $C_3$-$C_8$-cycloalkenyl, or a saturated 5, 6 or 7 membered heterocycle; each of which is optionally substituted;

$R^b$ represents halogen; nitro, cyano, $C_1$-$C_{12}$-alkyl; $C_1$-$C_6$-haloalkyl having 1 to 9 identical or different halogen atoms; $C_1$-$C_6$-alkoxy; $C_1$-$C_6$-haloalkoxy having 1 to 9 identical or different halogen atoms; $C_1$-$C_6$-alkylsulfanyl; $C_1$-$C_6$-haloalkylsulfanyl having 1 to 9 identical or different halogen atoms; $C_1$-$C_6$-alkylsulfonyl; $C_1$-$C_6$-haloalkylsulfonyl having 1 to 9 identical or different halogen atoms; $C_2$-$C_{12}$-alkenyl; $C_2$-$C_{12}$-alkynyl; $C_3$-$C_7$-cycloalkyl; phenyl; tri($C_1$-$C_8$)alkylsilyl; tri($C_1$-$C_8$)alkylsilyl-$C_1$-$C_8$-alkyl;

$Y^1$ and $Y^2$ independently of one another represent hydrogen, halogen, $C_1$-$C_{12}$-alkyl; $C_1$-$C_6$-haloalkyl having 1 to 9 identical or different halogen atoms; $C_1$-$C_8$-alkylsulfanyl; phenyl; each of which is optionally substituted; or $Y^1$ and $Y^2$ can form together with the carbon to which they are attached a $C_3$-$C_8$-cycloalkyl or a $C_3$-$C_8$-cycloalkenyl or a saturated 5, 6 or 7 membered heterocycle; each of which is optionally substituted;

$R^c$ represents $C_1$-$C_{16}$-alkyl; $C_1$-$C_6$-haloalkyl having 1 to 9 identical or different halogen atoms; $C_3$-$C_8$-cycloalkyl; ($C_3$-$C_8$-cycloalkyl)-$C_1$-$C_8$-alkyl; ($C_3$-$C_8$-cycloalkyl)-$C_3$-$C_8$-cycloalkyl; $C_2$-$C_8$-alkenyl-$C_1$-$C_{16}$-alkyl; $C_2$-$C_8$-alkynyl-$C_1$-$C_{16}$-alkyl; aryl-$C_1$-$C_8$-alkyl which is optionally substituted by up to 6 identical or different groups $R^b$; each of which is optionally substituted.

DETAILED DESCRIPTION OF A PREFERRED EMBODIMENT

In a preferred embodiment 1-methyl-3-dihalogenomethyl-5-halogenopyrazole(thio)tetrahydronaphthyl carboxamides of formula (I) are described, wherein $Hal^1$ represents chlorine or fluorine;

$Hal^2$ represents chlorine or fluorine;

T represents an oxygen atom;

Q represents hydrogen, $C_1$-$C_4$-alkylsulfonyl, $C_1$-$C_3$-alkoxy-$C_1$-$C_3$-alkyl, $C_1$-$C_4$-haloalkylsulfonyl, halo-$C_1$-$C_3$-alkoxy-$C_1$-$C_3$-alkyl having in each case 1 to 9 fluorine, chlorine and/or bromine atoms;

X represents fluorine, chlorine, methyl or trifluoromethyl;

m represents 0, 1 or 2;

$R^1$, $R^2$, $R^3$, $R^4$, $R^5$, $R^6$, $R^7$ and $R^8$ independently one to another represent hydrogen, halogen; cyano; $C_1$-$C_{16}$-alkyl; $C_1$-$C_6$-haloalkyl having 1 to 9 identical or different halogen atoms; $C_3$-$C_8$-cycloalkyl; ($C_3$-$C_8$-cycloalkyl)-$C_1$-$C_8$-alkyl; ($C_3$-$C_8$-cycloalkyl)-$C_3$-$C_8$-cycloalkyl; $C_2$-$C_8$-alkenyl; $C_2$-$C_8$-alkynyl; $C_2$-$C_8$-alkenyl-$C_1$-$C_{16}$-alkyl; $C_2$-$C_8$-alkynyl-$C_1$-$C_{16}$-alkyl; $C_1$-$C_{16}$-alkoxy; $C_3$-$C_8$-cycloalkyloxy; ($C_3$-$C_8$-cycloalkyl)-$C_1$-$C_8$-alkyloxy; $C_1$-$C_8$-alkylsulfanyl; $C_3$-$C_8$-cycloalkylsulfanyl; ($C_3$-$C_8$-cycloalkyl)-$C_1$-$C_8$-alkylsulfanyl; $C_2$-$C_8$-alkenyloxy; $C_3$-$C_8$-alkynyloxy; aryl-$C_1$-$C_8$-alkyloxy which is optionally substituted by up to 6 identical or different groups $R^b$; aryl-$C_1$-$C_8$-alkylsulfanyl which is optionally substituted by up to 6 identical or different groups $R^b$; aryloxy which is optionally substituted by up to 6 identical or different groups $R^b$; arylsulfanyl which is optionally substituted by up to 6 identical or different groups $R^b$; ($C_3$-$C_8$-cycloalkyl)-$C_2$-$C_8$-alkenyl; ($C_3$-$C_8$-cycloalkyl)-$C_2$-$C_8$-alkynyl; tri($C_1$-$C_8$)alkylsilyl; tri($C_1$-$C_8$)alkylsilyl-$C_1$-$C_8$-alkyl; aryl-$C_1$-$C_8$-alkyl which is optionally substituted by up to 6 identical or different groups $R^b$; aryl-$C_2$-$C_8$-alkenyl which is optionally substituted by up to 6 identical or different groups $R^b$; aryl-$C_2$-$C_8$-alkynyl which is optionally substituted by up to 6 identical or different groups $R^b$; each of which is optionally substituted; provided that $R^1$, $R^2$, $R^3$, $R^4$, $R^5$, $R^6$ and $R^7$ do not represent hydrogen at the same time when $R^8$ represents hydrogen or trifluoromethyl;

$R^1$ and $R^2$ can form together with the carbon to which they are attached an optionally substituted $C_3$-$C_8$-cycloalkyl; or may form the group $=C(Y^1)Y^2$ (where $Y^1$ and $Y^2$ independently of one another represent hydrogen, halogen, $C_1$-$C_{12}$-alkyl, $C_1$-$C_6$-haloalkyl having 1 to 9 identical or different halogen atoms or form together with the carbon to which they are attached an optionally substituted cyclopropyl, cyclobutyl, cyclopentyl, cyclohexyl) or a group $=N-O-R^c$ (where $R^c$ represents $C_1$-$C_{12}$-alkyl; $C_1$-$C_6$-haloalkyl having 1 to 9 identical or different halogen atoms; $C_3$-$C_6$-cycloalkyl; ($C_3$-$C_6$-cycloalkyl)-$C_1$-$C_6$-alkyl; ($C_3$-$C_6$-cycloalkyl)-$C_3$-$C_6$-cycloalkyl; $C_2$-$C_6$-alkenyl-$C_1$-$C_{12}$-alkyl; $C_2$-$C_6$-alkynyl-$C_1$-$C_{12}$-alkyl; aryl-$C_1$-$C_6$-alkyl which is optionally substituted by up to 6 identical or different groups $R^b$; each of which is optionally substituted);

$R^3$ and $R^4$ can form together with the carbon to which they are attached an optionally substituted $C_3$-$C_8$-cycloalkyl; or may form the group $=C(Y^1)Y^2$ (where $Y^1$ and $Y^2$ independently of one another represent hydrogen, halogen, $C_1$-$C_{12}$-alkyl, $C_1$-$C_6$-haloalkyl having 1 to 9 identical or different halogen atoms or form together with the carbon to which they are attached an optionally substituted cyclopropyl, cyclobutyl, cyclopentyl, cyclohexyl) or a group $=N-O-R^c$ (where $R^c$ represents $C_1$-$C_{12}$-alkyl; $C_1$-$C_6$-haloalkyl having 1 to 9 identical or different halogen atoms; $C_3$-$C_6$-cycloalkyl; ($C_3$-$C_6$-cycloalkyl)-$C_1$-$C_6$-alkyl; ($C_3$-$C_6$-cycloalkyl)-$C_3$-$C_6$-cycloalkyl; $C_2$-$C_6$-alkenyl-$C_1$-$C_{12}$-alkyl; $C_2$-$C_6$-alkynyl-$C_1$-$C_{12}$-alkyl; aryl-$C_1$-$C_6$-alkyl which is optionally substituted by up to 6 identical or different groups $R^b$; each of which is optionally substituted);

$R^5$ and $R^6$ can form together with the carbon to which they are attached an optionally substituted $C_3$-$C_8$-cycloalkyl; or may form the group $=C(Y^1)Y^2$ (where $Y^1$ and $Y^2$ independently of one another represent hydrogen, halogen, $C_1$-$C_{12}$-alkyl, $C_1$-$C_6$-haloalkyl having 1 to 9 identical or different halogen atoms or form together with the carbon to which they are attached an optionally substituted cyclopropyl, cyclobutyl, cyclopentyl, cyclohexyl) or a group $=N-O-R^c$ (where $R^c$ represents $C_1$-$C_{12}$-alkyl; $C_1$-$C_6$-haloalkyl having 1 to 9 identical or different halogen atoms; $C_3$-$C_6$-cycloalkyl; ($C_3$-$C_6$-cycloalkyl)-$C_1$-$C_6$-alkyl; ($C_3$-$C_6$-cycloalkyl)-$C_3$-$C_6$-cycloalkyl; $C_2$-$C_6$-alkenyl-$C_1$-$C_{12}$-alkyl; $C_2$-$C_6$-alkynyl-$C_1$-$C_{12}$-alkyl; aryl-$C_1$-$C_6$-alkyl which is optionally substituted by up to 6 identical or different groups $R^b$; each of which is optionally substituted);

$R^7$ and $R^8$ can form together with the carbon to which they are attached an optionally substituted $C_3$-$C_8$-cycloalkyl; or may form the group $=C(Y^1)Y^2$ (where $Y^1$ and $Y^2$ independently of one another represent hydrogen, halogen, $C_1$-$C_{12}$-alkyl, $C_1$-$C_6$-haloalkyl having 1 to 9 identical or different halogen atoms or form together with the carbon to which they are attached an optionally substituted cyclopropyl, cyclobutyl, cyclopentyl, cyclohexyl) or a group $=N-O-R^c$ (where $R^c$ represents $C_1$-$C_{12}$-alkyl; $C_1$-$C_6$-haloalkyl having 1 to 9 identical or different halogen atoms; $C_3$-$C_6$-cycloalkyl; ($C_3$-$C_6$-cycloalkyl)-$C_1$-$C_6$-alkyl; ($C_3$-$C_6$-cycloalkyl)-$C_3$-$C_6$-cycloalkyl; $C_2$-$C_6$-alkenyl-$C_1$-$C_{12}$-alkyl; $C_2$-$C_6$-alkynyl-$C_1$-$C_{12}$-alkyl; aryl-$C_1$-

$C_6$-alkyl which is optionally substituted by up to 6 identical or different groups $R^b$; each of which is optionally substituted);

$R^1$ and $R^3$ or $R^3$ and $R^5$ or $R^5$ and $R^7$ can form with the carbons to which they are attached an optionally substituted $C_3$-$C_8$-cycloalkyl;

$R^b$ represents halogen; nitro, cyano, $C_1$-$C_8$-alkyl; $C_1$-$C_4$-haloalkyl having 1 to 9 identical or different halogen atoms; $C_1$-$C_6$-alkoxy; $C_1$-$C_4$-haloalkoxy having 1 to 9 identical or different halogen atoms; $C_1$-$C_6$-alkylsulfanyl; $C_1$-$C_4$-haloalkylsulfanyl having 1 to 9 identical or different halogen atoms; $C_1$-$C_6$-alkylsulfonyl; $C_1$-$C_4$-haloalkylsulfonyl having 1 to 9 identical or different halogen atoms; $C_2$-$C_8$-alkenyl; $C_2$-$C_8$-alkynyl; $C_3$-$C_6$-cycloalkyl; phenyl; tri($C_1$-$C_6$)alkylsilyl; tri($C_1$-$C_6$)alkylsilyl-$C_1$-$C_6$-alkyl.

In a very preferred embodiment 1-Methyl-3-dihalogenomethyl-5-halogenopyrazole(thio)tetrahydronaphthyl carboxamides of formula (I) are described, wherein $Hal^1$ represents chlorine or fluorine;
$Hal^2$ represents chlorine or fluorine;
T represents an oxygen atom;
Q represents hydrogen, methylsulfonyl, ethylsulfonyl, n- or isopropylsulfonyl, n-, iso-, sec- or tert-butylsulfonyl, methoxymethyl, methoxyethyl, ethoxymethyl, ethoxyethyl, trifluoromethylsulfonyl, trifluoromethoxymethyl;
X represents fluorine, chlorine, methyl or trifluoromethyl located in the 4-, 5- or 6-position;
m represents 0 or 1;
$R^1$, $R^2$, $R^3$, $R^4$, $R^5$, $R^6$, $R^7$ and $R^8$ independently of one another represent hydrogen, fluorine, chlorine, bromine, iodine; $C_1$-$C_{12}$-alkyl; $C_1$-$C_6$-haloalkyl having 1 to 9 identical or different halogen atoms; $C_3$-$C_6$-cycloalkyl; ($C_3$-$C_6$-cycloalkyl)-$C_1$-$C_6$-alkyl; ($C_3$-$C_6$-cycloalkyl)-$C_3$-$C_6$-cycloalkyl; $C_1$-$C_{12}$-alkoxy; $C_3$-$C_6$-cycloalkyloxy; ($C_3$-$C_6$-cycloalkyl)-$C_1$-$C_6$-alkyloxy; each of which is optionally substituted; provided that $R^1$, $R^2$, $R^3$, $R^4$, $R^5$, $R^6$ and $R^7$ do not represent hydrogen at the same time when $R^8$ represents hydrogen or trifluoromethyl;
$R^1$ and $R^2$ can form together with the carbon to which they are attached an optionally substituted cyclopropyl, cyclobutyl, cyclopentyl, cyclohexyl; or may form the group $=C(Y^1)Y^2$ (where $Y^1$ and $Y^2$ independently of one another represent hydrogen, fluorine, chlorine, bromine, methyl; ethyl, propyl, isopropyl) or a group $=N-O-R^c$ (where $R^c$ represents $C_1$-$C_8$-alkyl; $C_1$-$C_4$-haloalkyl having 1 to 9 identical or different fluorine, chlorine or bromine atoms; $C_3$-$C_6$-cycloalkyl; ($C_3$-$C_6$-cycloalkyl)-$C_1$-$C_4$-alkyl; $C_2$-$C_6$-alkenyl-$C_1$-$C_8$-alkyl; $C_2$-$C_6$-alkynyl-$C_1$-$C_8$-alkyl; aryl-$C_1$-$C_4$-alkyl which is optionally substituted by up to 5 identical or different groups $R^b$; each of which is optionally substituted);
$R^3$ and $R^4$ can form together with the carbon to which they are attached an optionally substituted cyclopropyl, cyclobutyl, cyclopentyl, cyclohexyl; or may form the group $=C(Y^1)Y^2$ (where $Y^1$ and $Y^2$ independently of one another represent hydrogen, fluorine, chlorine, bromine, methyl; ethyl, propyl, isopropyl) or a group $=N-O-R^c$ (where $R^c$ represents $C_1$-$C_8$-alkyl; $C_1$-$C_4$-haloalkyl having 1 to 9 identical or different fluorine, chlorine or bromine atoms; $C_3$-$C_6$-cycloalkyl; ($C_3$-$C_6$-cycloalkyl)-$C_1$-$C_4$-alkyl; $C_2$-$C_6$-alkenyl-$C_1$-$C_8$-alkyl; $C_2$-$C_6$-alkynyl-$C_1$-$C_8$-alkyl; aryl-$C_1$-$C_4$-alkyl which is optionally substituted by up to 5 identical or different groups $R^b$; each of which is optionally substituted);
$R^5$ and $R^6$ can form together with the carbon to which they are attached an optionally substituted cyclopropyl, cyclobutyl, cyclopentyl, cyclohexyl; or may form the group $=C(Y^1)Y^2$ (where $Y^1$ and $Y^2$ independently of one another represent fluorine, chlorine, bromine, methyl; ethyl, propyl, isopropyl) or a group $=N-O-R^c$ (where $R^c$ represents $C_1$-$C_8$-alkyl; $C_1$-$C_4$-haloalkyl having 1 to 9 identical or different fluorine, chlorine or bromine atoms; $C_3$-$C_6$-cycloalkyl; ($C_3$-$C_6$-cycloalkyl)-$C_1$-$C_4$-alkyl; $C_2$-$C_6$-alkenyl-$C_1$-$C_8$-alkyl; $C_2$-$C_6$-alkynyl-$C_1$-$C_8$-alkyl; aryl-$C_1$-$C_4$-alkyl which is optionally substituted by up to 5 identical or different groups $R^b$; each of which is optionally substituted);
$R^7$ and $R^8$ can form together with the carbon to which they are attached an optionally substituted cyclopropyl, cyclobutyl, cyclopentyl, cyclohexyl; or may form the group $=C(Y^1)Y^2$ (where $Y^1$ and $Y^2$ independently of one another represent hydrogen, fluorine, chlorine, bromine, methyl; ethyl, propyl, isopropyl) or a group $=N-O-R^c$ (where $R^c$ represents $C_1$-$C_8$-alkyl; $C_1$-$C_4$-haloalkyl having 1 to 9 identical or different fluorine, chlorine or bromine atoms; $C_3$-$C_6$-cycloalkyl; ($C_3$-$C_6$-cycloalkyl)-$C_1$-$C_4$-alkyl; $C_2$-$C_6$-alkenyl-$C_1$-$C_8$-alkyl; $C_2$-$C_6$-alkynyl-$C_1$-$C_8$-alkyl; aryl-$C_1$-$C_4$-alkyl which is optionally substituted by up to 5 identical or different groups $R^b$; each of which is optionally substituted);
$R^1$ and $R^3$ or $R^3$ and $R^5$ or $R^5$ and $R^7$ can form together with the carbons to which they are attached an optionally substituted cyclopropyl, cyclobutyl, cyclopentyl, cyclohexyl.

$R^b$ represents fluorine, chlorine, bromine; $C_1$-$C_6$-alkyl; $C_1$-$C_4$-haloalkyl having 1 to 9 identical or different halogen atoms; $C_1$-$C_4$-alkoxy; $C_1$-$C_4$-haloalkoxy having 1 to 9 identical or different halogen atoms; $C_1$-$C_1$-alkylsulfanyl; $C_1$-$C_4$-haloalkylsulfanyl having 1 to 9 identical or different halogen atoms; $C_1$-$C_4$-alkylsulfonyl; $C_1$-$C_4$-haloalkylsulfonyl having 1 to 9 identical or different halogen atoms; $C_2$-$C_6$-alkenyl; $C_2$-$C_6$-alkynyl; $C_3$-$C_6$-cycloalkyl; phenyl; tri($C_1$-$C_4$)alkylsilyl; tri($C_1$-$C_4$)alkylsilyl $C_1$-$C_4$ alkyl.

The formula (I) provides a general definition of the 1-methyl-3-dihalogenomethyl-5-halogenopyrazole-(thio)tetrahydronaphthyl carboxamides according to the invention. Preferred radical definitions for the formulae shown above and below are given below. These definitions apply to the end products of the formula (I) and likewise to all intermediates.

$Hal^1$ preferably represents chlorine.
$Hal^1$ also preferably represents fluorine.
$Hal^2$ preferably represents chlorine.
$Hal^2$ also preferably represents fluorine.
T preferably represents an oxygen atom.
Q preferably represents hydrogen, $C_1$-$C_4$-alkylsulfonyl, $C_1$-$C_3$-alkoxy-$C_1$-$C_3$-alkyl, $C_1$-$C_4$-haloalkylsulfonyl, halo-$C_1$-$C_3$-alkoxy-$C_1$-$C_3$-alkyl having in each case 1 to 9 fluorine, chlorine and/or bromine atoms;
Q particularly preferably represents hydrogen, methylsulfonyl, ethylsulfonyl, n- or isopropylsulfonyl, n-, iso-, sec- or tert-butylsulfonyl, methoxymethyl, methoxyethyl, ethoxymethyl, ethoxyethyl, trifluoromethylsulfonyl, trifluoromethoxymethyl.
Q very particularly preferably represents hydrogen.
X preferably represents fluorine, chlorine, methyl or trifluoromethyl.
X particularly preferably represents fluorine, where fluorine is particularly preferably located in the 4-, 5- or 6-position, very particularly preferably in the 4- or 6-position, in particular in the 4-position of the tetrahydronaphthyl radical.
X moreover particularly preferably represents chlorine, where chlorine is particularly preferably located in the 4- or 5-position, in particular in the 4-position of the tetrahydronaphthyl radical.

X moreover particularly preferably represents methyl, where methyl is particularly preferably located in the 4- or 5-position of the tetrahydronaphthyl radical.

X moreover particularly preferably represents trifluoromethyl, where trifluoromethyl is particularly preferably located in the 4- or 5-position of the tetrahydronaphthyl radical.

m preferably represents 0, 1 or 2.

m particularly preferably represents 0 or 1.

m very particularly preferably represents 0.

$R^1$, $R^2$, $R^3$, $R^4$, $R^5$, $R^6$, $R^7$ and $R^8$ independently of one another preferably represent hydrogen, halogen; cyano; $C_1$-$C_{16}$-alkyl; $C_1$-$C_6$-haloalkyl having 1 to 9 identical or different halogen atoms; $C_3$-$C_8$-cycloalkyl; ($C_3$-$C_8$-cycloalkyl)-$C_1$-$C_8$-alkyl; ($C_3$-$C_8$-cycloalkyl)-$C_3$-$C_8$-cycloalkyl; $C_2$-$C_8$-alkenyl; $C_2$-$C_8$-alkynyl; $C_2$-$C_8$-alkenyl-$C_1$-$C_{16}$-alkyl; $C_2$-$C_8$-alkynyl-$C_1$-$C_{16}$-alkyl; $C_1$-$C_{16}$-alkoxy; $C_3$-$C_8$-cycloalkyloxy; ($C_3$-$C_8$-cycloalkyl)-$C_1$-$C_8$-alkyloxy; $C_1$-$C_8$-alkylsulfanyl; $C_3$-$C_8$-cycloalkylsulfanyl; ($C_3$-$C_8$-cycloalkyl)-$C_1$-$C_8$-alkylsulfanyl; $C_2$-$C_8$-alkenyloxy; $C_3$-$C_8$-alkynyloxy; aryl-$C_1$-$C_8$-alkyloxy which is optionally substituted by up to 6 identical or different groups $R^b$; aryl-$C_1$-$C_8$-alkylsulfanyl which is optionally substituted by up to 6 identical or different groups $R^b$; aryloxy which is optionally substituted by up to 6 identical or different groups $R^b$; arylsulfanyl which is optionally substituted by up to 6 identical or different groups $R^b$; ($C_3$-$C_8$-cycloalkyl)-$C_2$-$C_8$-alkenyl; ($C_3$-$C_8$-cycloalkyl)-$C_2$-$C_8$-alkynyl; tri($C_1$-$C_8$)alkylsilyl; tri($C_1$-$C_8$)alkylsilyl-$C_1$-$C_8$-alkyl; aryl-$C_1$-$C_8$-alkyl which is optionally substituted by up to 6 identical or different groups $R^b$; aryl-$C_2$-$C_8$-alkenyl which is optionally substituted by up to 6 identical or different groups $R^b$; aryl-$C_2$-$C_8$-alkynyl which is optionally substituted by up to 6 identical or different groups $R^b$; each of which is optionally substituted; provided that $R^1$, $R^2$, $R^3$, $R^4$, $R^5$, $R^6$ and $R^7$ do not represent hydrogen at the same time when $R^8$ represents hydrogen or trifluoromethyl.

$R^1$, $R^2$, $R^3$, $R^4$, $R^5$, $R^6$, $R^7$ and $R^8$ independently of one another particularly preferably represent hydrogen, fluorine, chlorine, bromine, iodine; $C_1$-$C_{12}$-alkyl; $C_1$-$C_6$-haloalkyl having 1 to 9 identical or different halogen atoms; $C_3$-$C_6$-cycloalkyl; ($C_3$-$C_6$-cycloalkyl)-$C_1$-$C_6$-alkyl; ($C_3$-$C_6$-cycloalkyl)-$C_3$-$C_6$-cycloalkyl; $C_1$-$C_{12}$-alkoxy; $C_3$-$C_6$-cycloalkyloxy; ($C_3$-$C_6$-cycloalkyl)-$C_1$-$C_6$-alkyloxy; each of which is optionally substituted; provided that $R^1$, $R^2$, $R^3$, $R^4$, $R^5$, $R^6$ and $R^7$ do not represent hydrogen at the same time when $R^8$ represents hydrogen or trifluoromethyl.

$R^1$, $R^2$, $R^3$, $R^4$, $R^5$, $R^6$, $R^7$ and $R^8$ independently of one another very particularly preferably represent hydrogen, methyl, ethyl, propyl, isopropyl, n-butyl, iso-butyl, sec-butyl, tert-butyl, methoxy, ethoxy, propyloxy, isopropyloxy, n-butyloxy, iso-butyloxy, sec-butyloxy, tert-butyloxy; provided that $R^1$, $R^2$, $R^3$, $R^4$, $R^5$, $R^6$ and $R^7$ do not represent hydrogen at the same time when $R^8$ represents hydrogen or trifluoromethyl.

$R^1$ and $R^2$ can preferably form together with the carbon to which they are attached an optionally substituted $C_3$-$C_8$-cycloalkyl; or may form the group $=C(Y^1)Y^2$ (where $Y^1$ and $Y^2$ independently of one another represent hydrogen, halogen, $C_1$-$C_{12}$-alkyl, $C_1$-$C_6$-haloalkyl having 1 to 9 identical or different halogen atoms or form together with the carbon to which they are attached an optionally substituted cyclopropyl, cyclobutyl, cyclopentyl, cyclohexyl) or a group $=N-O-R^c$ (where $R^c$ represents $C_1$-$C_{12}$-alkyl; $C_1$-$C_6$-haloalkyl having 1 to 9 identical or different halogen atoms; $C_3$-$C_6$-cycloalkyl; ($C_3$-$C_6$-cycloalkyl)-$C_1$-$C_6$-alkyl; ($C_3$-$C_6$-cycloalkyl)-$C_3$-$C_6$-cycloalkyl; $C_2$-$C_6$-alkenyl-$C_1$-$C_{12}$-alkyl; $C_2$-$C_6$-alkynyl-$C_1$-$C_{12}$-alkyl; aryl-$C_1$-$C_6$-alkyl which is optionally substituted by up to 6 identical or different groups $R^b$; each of which is optionally substituted).

$R^1$ and $R^2$ can preferably form together with the carbon to which they are attached an optionally substituted $C_3$-$C_8$-cycloalkyl; or may form the group $=C(Y^1)Y^2$ (where $Y^1$ and $Y^2$ independently of one another represent halogen, $C_1$-$C_{12}$-alkyl, $C_1$-$C_6$-haloalkyl having 1 to 9 identical or different halogen atoms or form together with the carbon to which they are attached an optionally substituted cyclopropyl, cyclobutyl, cyclopentyl, cyclohexyl) or a group $=N-O-R^c$ (where $R^c$ represents $C_1$-$C_{12}$-alkyl; $C_1$-$C_6$-haloalkyl having 1 to 9 identical or different halogen atoms; $C_3$-$C_6$-cycloalkyl; ($C_3$-$C_6$-cycloalkyl)-$C_1$-$C_6$-alkyl; ($C_3$-$C_6$-cycloalkyl)-$C_3$-$C_6$-cycloalkyl; $C_2$-$C_6$-alkenyl-$C_1$-$C_{12}$-alkyl; $C_2$-$C_6$-alkynyl-$C_1$-$C_{12}$-alkyl; aryl-$C_1$-$C_6$-alkyl which is optionally substituted by up to 6 identical or different groups $R^b$; each of which is optionally substituted).

$R^1$ and $R^2$ can particularly preferably form together with the carbon to which they are attached an optionally substituted cyclopropyl, cyclobutyl, cyclopentyl, cyclohexyl; or may form the group $=C(Y^1)Y^2$ (where $Y^1$ and $Y^2$ independently of one another represent hydrogen, fluorine, chlorine, bromine, methyl; ethyl, propyl, isopropyl) or a group $=N-O-R^c$ (where $R^c$ represents $C_1$-$C_8$-alkyl; $C_1$-$C_4$-haloalkyl having 1 to 9 identical or different fluorine, chlorine or bromine atoms; $C_3$-$C_6$-cycloalkyl; ($C_3$-$C_6$-cycloalkyl)-$C_1$-$C_4$-alkyl; $C_2$-$C_6$-alkenyl-$C_1$-$C_8$-alkyl; $C_2$-$C_6$-alkynyl-$C_1$-$C_8$-alkyl; aryl-$C_1$-$C_4$-alkyl which is optionally substituted by up to 5 identical or different groups $R^b$; each of which is optionally substituted).

$R^1$ and $R^2$ can particularly preferably form together with the carbon to which they are attached an optionally substituted cyclopropyl, cyclobutyl, cyclopentyl, cyclohexyl; or may form the group $=C(Y^1)Y^2$ (where $Y^1$ and $Y^2$ independently of one another represent fluorine, chlorine, bromine, methyl; ethyl, propyl, isopropyl) or a group $=N-O-R^c$ (where $R^c$ represents $C_1$-$C_8$-alkyl; $C_1$-$C_4$-haloalkyl having 1 to 9 identical or different fluorine, chlorine or bromine atoms; $C_3$-$C_6$-cycloalkyl; ($C_3$-$C_6$-cycloalkyl)-$C_1$-$C_4$-alkyl; $C_2$-$C_6$-alkenyl-$C_1$-$C_8$-alkyl; $C_2$-$C_6$-alkynyl-$C_1$-$C_8$-alkyl; aryl-$C_1$-$C_4$-alkyl which is optionally substituted by up to 5 identical or different groups $R^b$; each of which is optionally substituted).

$R^3$ and $R^4$ can preferably form together with the carbon to which they are attached an optionally substituted $C_3$-$C_8$-cycloalkyl; or may form the group $=C(Y^1)Y^2$ (where $Y^1$ and $Y^2$ independently of one another represent hydrogen, halogen, $C_1$-$C_{12}$-alkyl, $C_1$-$C_6$-haloalkyl having 1 to 9 identical or different halogen atoms or form together with the carbon to which they are attached an optionally substituted cyclopropyl, cyclobutyl, cyclopentyl, cyclohexyl) or a group $=N-O-R^c$ (where $R^c$ represents $C_1$-$C_{12}$-alkyl; $C_1$-$C_6$-haloalkyl having 1 to 9 identical or different halogen atoms; $C_3$-$C_6$-cycloalkyl; ($C_3$-$C_6$-cycloalkyl)-$C_1$-$C_6$-alkyl; ($C_3$-$C_6$-cycloalkyl)-$C_3$-$C_6$-cycloalkyl; $C_2$-$C_6$-alkenyl-$C_1$-$C_{12}$-alkyl; $C_2$-$C_6$-alkynyl-$C_1$-$C_{12}$-alkyl; aryl-$C_1$-$C_6$-alkyl which is optionally substituted by up to 6 identical or different groups $R^b$; each of which is optionally substituted).

$R^3$ and $R^4$ can preferably form together with the carbon to which they are attached an optionally substituted $C_3$-$C_8$-cycloalkyl; or may form the group $=C(Y^1)Y^2$ (where $Y^1$ and $Y^2$ independently of one another represent halogen, $C_1$-$C_{12}$-alkyl, $C_1$-$C_6$-haloalkyl having 1 to 9 identical or different halogen atoms or form together with the carbon to which they are attached an optionally substituted cyclopropyl, cyclobutyl, cyclopentyl, cyclohexyl) or a group =N—O—$R^c$ (where $R^c$ represents $C_1$-$C_{12}$-alkyl; $C_1$-$C_6$-haloalkyl having 1 to 9 identical or different halogen atoms; $C_3$-$C_6$-cycloalkyl; ($C_3$-$C_6$-cycloalkyl)-$C_1$-$C_6$-alkyl; ($C_3$-$C_6$-cycloalkyl)-$C_3$-$C_6$-cycloalkyl; $C_2$-$C_6$-alkenyl-$C_1$-$C_{12}$-alkyl; $C_2$-$C_6$-alkynyl-$C_1$-$C_{12}$-alkyl; aryl-$C_1$-$C_6$-alkyl which is optionally substituted by up to 6 identical or different groups $R^b$; each of which is optionally substituted).

$R^3$ and $R^4$ can particularly preferably form together with the carbon to which they are attached an optionally substituted cyclopropyl, cyclobutyl, cyclopentyl, cyclohexyl; or may form the group =C($Y^1$)$Y^2$ (where $Y^1$ and $Y^2$ independently of one another represent hydrogen, fluorine, chlorine, bromine, methyl; ethyl, propyl, isopropyl) or a group =N—O—$R^c$ (where $R^c$ represents $C_1$-$C_8$-alkyl; $C_1$-$C_4$-haloalkyl having 1 to 9 identical or different fluorine, chlorine or bromine atoms; $C_3$-$C_6$-cycloalkyl; ($C_3$-$C_6$-cycloalkyl)-$C_1$-$C_4$-alkyl; $C_2$-$C_6$-alkenyl-$C_1$-$C_8$-alkyl; $C_2$-$C_6$-alkynyl-$C_1$-$C_8$-alkyl; aryl-$C_1$-$C_4$-alkyl which is optionally substituted by up to 5 identical or different groups $R^b$; each of which is optionally substituted).

$R^3$ and $R^4$ can particularly preferably form together with the carbon to which they are attached an optionally substituted cyclopropyl, cyclobutyl, cyclopentyl, cyclohexyl; or may form the group =C($Y^1$)$Y^2$ (where $Y^1$ and $Y^2$ independently of one another represent fluorine, chlorine, bromine, methyl; ethyl, propyl, isopropyl) or a group =N—O—$R^c$ (where $R^c$ represents $C_1$-$C_8$-alkyl; $C_1$-$C_4$-haloalkyl having 1 to 9 identical or different fluorine, chlorine or bromine atoms; $C_3$-$C_6$-cycloalkyl; ($C_3$-$C_6$-cycloalkyl)-$C_1$-$C_4$-alkyl; $C_2$-$C_6$-alkenyl-$C_1$-$C_8$-alkyl; $C_2$-$C_6$-alkynyl-$C_1$-$C_8$-alkyl; aryl-$C_1$-$C_4$-alkyl which is optionally substituted by up to 5 identical or different groups $R^b$; each of which is optionally substituted).

$R^5$ and $R^6$ can preferably form together with the carbon to which they are attached an optionally substituted $C_3$-$C_8$-cycloalkyl; or may form the group =C($Y^1$)$Y^2$ (where $Y^1$ and $Y^2$ independently of one another represent halogen, $C_1$-$C_{12}$-alkyl, $C_1$-$C_6$-haloalkyl having 1 to 9 identical or different halogen atoms or form together with the carbon to which they are attached an optionally substituted cyclopropyl, cyclobutyl, cyclopentyl, cyclohexyl) or a group =N—O—$R^c$ (where $R^c$ represents $C_1$-$C_{12}$-alkyl; $C_1$-$C_6$-haloalkyl having 1 to 9 identical or different halogen atoms; $C_3$-$C_6$-cycloalkyl; ($C_3$-$C_6$-cycloalkyl)-$C_1$-$C_6$-alkyl; ($C_3$-$C_6$-cycloalkyl)-$C_3$-$C_6$-cycloalkyl; $C_2$-$C_6$-alkenyl-$C_1$-$C_{12}$-alkyl; $C_2$-$C_6$-alkynyl-$C_1$-$C_{12}$-alkyl; aryl-$C_1$-$C_6$-alkyl which is optionally substituted by up to 6 identical or different groups $R^b$; each of which is optionally substituted).

$R^5$ and $R^6$ can particularly preferably form together with the carbon to which they are attached an optionally substituted cyclopropyl, cyclobutyl, cyclopentyl, cyclohexyl; or may form the group =C($Y^1$)$Y^2$ (where $Y^1$ and $Y^2$ independently of one another represent hydrogen, fluorine, chlorine, bromine, methyl; ethyl, propyl, isopropyl) or a group =N—O—$R^c$ (where $R^c$ represents $C_1$-$C_8$-alkyl; $C_1$-$C_4$-haloalkyl having 1 to 9 identical or different fluorine, chlorine or bromine atoms; $C_3$-$C_6$-cycloalkyl; ($C_3$-$C_6$-cycloalkyl)-$C_1$-$C_4$-alkyl; $C_2$-$C_6$-alkenyl-$C_1$-$C_8$-alkyl; $C_2$-$C_6$-alkynyl-$C_1$-$C_8$-alkyl; aryl-$C_1$-$C_4$-alkyl which is optionally substituted by up to 5 identical or different groups $R^b$; each of which is optionally substituted).

$R^5$ and $R^6$ can particularly preferably form together with the carbon to which they are attached an optionally substituted cyclopropyl, cyclobutyl, cyclopentyl, cyclohexyl; or may form the group =C($Y^1$)$Y^2$ (where $Y^1$ and $Y^2$ independently of one another represent fluorine, chlorine, bromine, methyl; ethyl, propyl, isopropyl) or a group =N—O—$R^c$ (where $R^c$ represents $C_1$-$C_8$-alkyl; $C_1$-$C_4$-haloalkyl having 1 to 9 identical or different fluorine, chlorine or bromine atoms; $C_3$-$C_6$-cycloalkyl; ($C_3$-$C_6$-cycloalkyl)-$C_1$-$C_4$-alkyl; $C_2$-$C_6$-alkenyl-$C_1$-$C_8$-alkyl; $C_2$-$C_6$-alkynyl-$C_1$-$C_8$-alkyl; aryl-$C_1$-$C_4$-alkyl which is optionally substituted by up to 5 identical or different groups $R^b$; each of which is optionally substituted).

$R^7$ and $R^8$ can preferably form together with the carbon to which they are attached an optionally substituted $C_3$-$C_8$-cycloalkyl; or may form the group =C($Y^1$)$Y^2$ (where $Y^1$ and $Y^2$ independently of one another represent hydrogen, halogen, $C_1$-$C_{12}$-alkyl, $C_1$-$C_6$-haloalkyl having 1 to 9 identical or different halogen atoms or form together with the carbon to which they are attached an optionally substituted cyclopropyl, cyclobutyl, cyclopentyl, cyclohexyl) or a group =N—O—$R^c$ (where $R^c$ represents $C_1$-$C_{12}$-alkyl; $C_1$-$C_6$-haloalkyl having 1 to 9 identical or different halogen atoms; $C_3$-$C_6$-cycloalkyl; ($C_3$-$C_6$-cycloalkyl)-$C_1$-$C_6$-alkyl; ($C_3$-$C_6$-cycloalkyl)-$C_3$-$C_6$-cycloalkyl; $C_2$-$C_6$-alkenyl-$C_1$-$C_{12}$-alkyl; $C_2$-$C_6$-alkynyl-$C_1$-$C_{12}$-alkyl; aryl-$C_1$-$C_6$-alkyl which is optionally substituted by up to 6 identical or different groups $R^b$; each of which is optionally substituted).

$R^7$ and $R^8$ can preferably form together with the carbon to which they are attached an optionally substituted $C_3$-$C_8$-cycloalkyl; or may form the group =C($Y^1$)$Y^2$ (where $Y^1$ and $Y^2$ independently of one another represent halogen, $C_1$-$C_{12}$-alkyl, $C_1$-$C_6$-haloalkyl having 1 to 9 identical or different halogen atoms or form together with the carbon to which they are attached an optionally substituted cyclopropyl, cyclobutyl, cyclopentyl, cyclohexyl) or a group =N—O—$R^c$ (where $R^c$ represents $C_1$-$C_{12}$-alkyl; $C_1$-$C_6$-haloalkyl having 1 to 9 identical or different halogen atoms; $C_3$-$C_6$-cycloalkyl; ($C_3$-$C_6$-cycloalkyl)-$C_1$-$C_6$-alkyl; ($C_3$-$C_6$-cycloalkyl)-$C_3$-$C_6$-cycloalkyl; $C_2$-$C_6$-alkenyl-$C_1$-$C_{12}$-alkyl; $C_2$-$C_6$-alkynyl-$C_1$-$C_{12}$-alkyl; aryl-$C_1$-$C_6$-alkyl which is optionally substituted by up to 6 identical or different groups $R^b$; each of which is optionally substituted).

$R^7$ and $R^8$ can particularly preferably form together with the carbon to which they are attached an optionally substituted cyclopropyl, cyclobutyl, cyclopentyl, cyclohexyl; or may form the group =C($Y^1$)$Y^2$ (where $Y^1$ and $Y^2$ independently of one another represent hydrogen, fluorine, chlorine, bromine, methyl; ethyl, propyl, isopropyl) or a group =N—O—$R^c$ (where $R^c$ represents $C_1$-$C_8$-alkyl; $C_1$-$C_4$-haloalkyl having 1 to 9 identical or different fluorine, chlorine or bromine atoms; $C_3$-$C_6$-cycloalkyl; ($C_3$-$C_6$-cycloalkyl)-$C_1$-$C_4$-alkyl; $C_2$-$C_6$-alkenyl-$C_1$-$C_8$-alkyl; $C_2$-$C_6$-alkynyl-$C_1$-$C_8$-alkyl; aryl-$C_1$-$C_4$-alkyl which is optionally substituted by up to 5 identical or different groups $R^b$; each of which is optionally substituted).

$R^7$ and $R^8$ can particularly preferably form together with the carbon to which they are attached an optionally substituted cyclopropyl, cyclobutyl, cyclopentyl, cyclohexyl; or may form the group =C($Y^1$)$Y^2$ (where $Y^1$ and $Y^2$ independently of one another represent fluorine, chlorine, bromine, methyl; ethyl, propyl, isopropyl) or a group =N—O—$R^c$ (where $R^c$ represents $C_1$-$C_8$-alkyl; $C_1$-$C_4$-haloalkyl having 1 to 9 identical or different fluorine, chlorine or bromine atoms; $C_3$-$C_6$-cycloalkyl; ($C_3$-$C_6$-cycloalkyl)-$C_1$-$C_4$- alkyl; $C_2$-$C_6$-alkenyl-$C_1$-$C_8$-alkyl; $C_2$-$C_6$-alkynyl-$C_1$-$C_8$-alkyl; aryl-$C_1$-$C_4$-alkyl which is optionally substituted by up to 5 identical or different groups $R^b$; each of which is optionally substituted).

$R^1$ and $R^3$ or $R^3$ and $R^5$ or $R^5$ and $R^7$ can preferably form together with the carbons to which they are attached an optionally substituted $C_3$-$C_8$-cycloalkyl.

$R^1$ and $R^3$ or $R^3$ and $R^5$ or $R^5$ and $R^7$ can particularly preferably form together with the carbons to which they are attached an optionally substituted cyclopropyl, cyclobutyl, cyclopentyl, cyclohexyl.

$R^b$ preferably represents halogen; nitro, cyano, $C_1$-$C_8$-alkyl; $C_1$-$C_4$-haloalkyl having 1 to 9 identical or different halogen atoms; $C_1$-$C_6$-alkoxy; $C_1$-$C_4$-haloalkoxy having 1 to 9 identical or different halogen atoms; $C_1$-$C_6$-alkylsulfanyl; $C_1$-$C_4$-haloalkylsulfanyl having 1 to 9 identical or different halogen atoms; $C_1$-$C_6$-alkylsulfonyl; $C_1$-$C_4$-haloalkylsulfonyl having 1 to 9 identical or different halogen atoms; $C_2$-$C_8$-alkenyl; $C_2$-$C_8$-alkynyl; $C_3$-$C_6$-cycloalkyl; phenyl; tri($C_1$-$C_6$)alkylsilyl; tri($C_1$-$C_6$)alkylsilyl-$C_1$-$C_6$-alkyl.

$R^b$ particularly preferably represents fluorine, chlorine, bromine; $C_1$-$C_6$-alkyl; $C_1$-$C_4$-haloalkyl having 1 to 9 identical or different halogen atoms; $C_1$-$C_4$-alkoxy; $C_1$-$C_4$-haloalkoxy having 1 to 9 identical or different halogen atoms; $C_1$-$C_4$-alkylsulfanyl; $C_1$-$C_4$-haloalkylsulfanyl having 1 to 9 identical or different halogen atoms; $C_1$-$C_4$-alkylsulfonyl; $C_1$-$C_4$-haloalkylsulfonyl having 1 to 9 identical or different halogen atoms; $C_2$-$C_6$-alkenyl; $C_2$-$C_6$-alkynyl; $C_3$-$C_6$-cycloalkyl; phenyl; tri($C_1$-$C_4$)alkylsilyl; tri($C_1$-$C_4$)alkylsilyl $C_1$-$C_4$ alkyl.

$R^b$ very particularly preferably represents fluorine, chlorine, bromine; methyl, ethyl, n-propyl, isopropyl, n-, s-, t-butyl, trifluoromethyl, trichloromethyl, difluoromethyl, methoxy, trifluoromethoxy, methylsulfanyl, trifluoromethylsulfanyl, vinyl, allyl, ethinyl, propargyl, cyclopropyl, phenyl, trimethylsilyl.

Unless indicated otherwise, a group or a substituent which is substituted according to the invention is substituted by one or more group selected in the list consisting of halogen; nitro, cyano, $C_1$-$C_{16}$-alkyl; $C_1$-$C_6$-haloalkyl having 1 to 9 identical or different halogen atoms; $C_1$-$C_6$-alkoxy; $C_1$-$C_6$-haloalkoxy having 1 to 9 identical or different halogen atoms; $C_1$-$C_6$-alkylsulfanyl; $C_1$-$C_6$-haloalkylsulfanyl having 1 to 9 identical or different halogen atoms; $C_1$-$C_6$-alkylsulfonyl; $C_1$-$C_6$-haloalkylsulfonyl having 1 to 9 identical or different halogen atoms; $C_2$-$C_{12}$-alkenyl; $C_2$-$C_{12}$-alkynyl; $C_3$-$C_7$-cycloalkyl; phenyl; tri($C_1$-$C_8$)alkylsilyl; tri($C_1$-$C_8$)alkylsilyl-$C_1$-$C_8$-alkyl.

Finally, it has been found that the novel (thio) carboxamides of the formula (I) have very good microbicidal properties and can be used for controlling unwanted microorganisms both in crop protection and in the protection of materials.

The definition $C_1$-$C_{16}$-alkyl comprises the largest range defined here for an alkyl radical. Specifically, this definition comprises the meanings methyl, ethyl, n-, isopropyl, n-, iso-, sec-, tert-butyl, and also in each case all isomeric pentyls, hexyls, heptyls, octyls, nonyls, decyls, undecyls, dodecyls, tridecyls, tetradecyls, pentadecyls, hexadecyls. A preferred range is $C_2$-$C_{12}$-alkyl, such as ethyl and straight-chain or branched propyl, butyl, pentyl, hexyl, heptyl, octyl, nonyl, decyl, undecyl and dodecyl, particularly straight-chain or branched $C_3$-$C_{10}$-alkyl, such as propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-3-methylpropyl, n-heptyl, 1-methylhexyl, 1-ethylpentyl, 2-ethylpentyl, 1-propylbutyl, octyl, 1-methylheptyl, 2-methylheptyl, 1-ethylhexyl, 2-ethylhexyl, 1-propylpentyl, 2-propylpentyl, nonyl, 1-methyloctyl, 2-methyloctyl, 1-ethylheptyl, 2-ethylheptyl, 1-propylhexyl, 2-propylhexyl, decyl, 1-methylnonyl, 2-methylnonyl, 1-ethyloctyl, 2-ethyloctyl, 1-propylheptyl and 2-propylheptyl, in particular propyl, 1-methylethyl, butyl, 1-methylbutyl, 2-methylbutyl, 3-methylbutyl, 1,1-dimethylethyl, 1,2-dimethylbutyl, 1,3-dimethylbutyl, pentyl, 1-methylbutyl, 1-ethylpropyl, hexyl, 3-methylpentyl, heptyl, 1-methylhexyl, 1-ethyl-3-methylbutyl, 1-methylheptyl, 1,2-dimethylhexyl, 1,3-dimethyloctyl, 4-methyloctyl, 1,2,2,3-tetramethylbutyl, 1,3,3-trimethylbutyl, 1,2,3-trimethylbutyl, 1,3-dimethylpentyl, 1,3-dimethylhexyl, 5-methyl-3-hexyl, 2-methyl-4-heptyl, 2,6-dimethyl-4-heptyl and 1-methyl-2-cyclopropylethyl.

Halogen-substituted alkyl represents, for example, chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 3-chloro-1-methylbutyl, 2-chloro-1-methylbutyl, 1-chlorobutyl, 3,3-dichloro-1-methylbutyl, 3-chloro-1-methylbutyl, 1-methyl-3-trifluoromethylbutyl, 3-methyl-1-trifluoromethylbutyl.

The definition tri($C_1$-$C_8$)alkylsilyl preferably represents the following radicals: $SiMe_3$, $SiMe_2Et$, $SiMe_2CHMe_2$, $SiMe_2CH_2CHMe_2$, $SiMe_2CH_2CMe_3$, $SiMe_2CMe_3$, $SiMe_2CH_2CH_2Me$.

The definition $C_2$-$C_{16}$-alkenyl comprises the largest range defined here for an alkenyl radical. Specifically, this definition comprises the meanings ethenyl, n-, isopropenyl, n-, iso-, sec-, tert-butenyl, and also in each case all isomeric pentenyls, hexenyls, heptenyls, octenyls, nonenyls, decenyls, undecenyls, dodecenyls, tridecenyls, tetradecenyls, pentadecenyls, hexadecenyls, 1-methyl-1-propenyl, 1-ethyl-1-butenyl, 2,4-dimethyl-1-pentenyl, 2,4-dimethyl-2-pentenyl.

The definition $C_2$-$C_{16}$-alkynyl comprises the largest range defined here for an alkynyl radical. Specifically, this definition comprises the meanings ethynyl, n-, isopropynyl, n-, iso-, sec-, tert-butynyl, and also in each case all isomeric pentynyls, hexynyls, heptynyls, octynyls, nonynyls, decynyls, undecynyls, dodecynyls, tridecynyls, tetradecynyls, pentadecynyls, hexadecynyls.

The definition cycloalkyl comprises monocyclic saturated hydrocarbyl groups having 3 to 8 carbon ring members, such as cyclopropyl, cyclobutyl, cyclopentyl, cyclohexyl, cycloheptyl and cyclooctyl.

The definition aryl comprises unsubstituted or substituted, aromatic, mono-, bi- or tricyclic ring, for example phenyl, naphthyl, anthracenyl (anthryl), phenanthracenyl (phenanthryl).

The definition heterocycle comprises unsubstituted or substituted, unsaturated heterocyclic 5- to 7-membered ring containing up to 4 heteroatoms selected from N, O and S: for example 2-furyl, 3-furyl, 2-thienyl, 3-thienyl, 2-pyrrolyl, 3-pyrrolyl, 1-pyrrolyl, 3-pyrazolyl, 4-pyrazolyl, 5-pyrazolyl, 1-pyrazolyl, 1H-imidazol-2-yl, 1H-imidazol-4-yl, 1H-imidazol-5-yl, 1H-imidazol-1-yl, 2-oxazolyl, 4-oxazolyl, 5-oxazolyl, 2-thiazolyl, 4-thiazolyl, 5-thiazolyl, 3-isoxazolyl, 4-isoxazolyl, 5-isoxazolyl, 3-isothiazolyl, 4-isothiazolyl, 5-isothiazolyl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-3-yl, 1H-1,2,4-triazol-5-yl, 1H-1, 2,4-triazol-1-yl, 4H-1,2,4-triazol-3-yl, 4H-1,2,4-triazol-4-yl, 1H-tetrazol-1-yl, 1H-tetrazol-5-yl, 2H-tetrazol-2-yl, 2H-tetrazol-5-yl, 1,2,4-oxadiazol-3-yl, 1,2,4-oxadiazol-5-yl, 1,2,4-thiadiazol-3-yl, 1,2,4-thiadiazol-5-yl, 1,3,4-oxadiazol-2-yl, 1,3,4-thiadiazol-2-yl, 1,2,3-oxadiazol-4-yl, 1,2,3-oxadiazol-5-yl, 1,2,3-thiadiazol-4-yl, 1,2,3-thiadiazol-5-yl, 1,2,5-oxadiazol-3-yl, 1,2,5-thiadiazol-3-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4-triazin-5-yl, 1,2,4-triazin-6-yl.

Optionally substituted radicals may be mono- or polysubstituted, where in the case of polysubstitution, the substituents may be identical or different. Thus, the definition dialkylamino also embraces an amino group which is substituted asymmetrically by alkyl, such as, for example, methylethylamino.

Halogen-substituted radicals, such as, for example, halogenoalkyl, are mono- or polyhalogenated. In the case of polyhalogenation, the halogen atoms may be identical or different. Here, halogen represents fluorine, chlorine, bromine and iodine, in particular fluorine, chlorine and bromine.

However, the general or preferred radical definitions or illustrations given above can also be combined with one another as desired, i.e. including combinations between the respective ranges and preferred ranges. They apply to the end products and, correspondingly, to precursors and intermediates.

The radical definitions and explanations given above in general terms or stated within preferred ranges can, however, also be combined with one another as desired, i.e. including between the particular ranges and preferred ranges. They apply both to the end products and correspondingly to precursors and intermediates. In addition, individual definitions may not apply.

Preference is given to those compounds of the formula (I) in which each of the radicals have the above mentioned preferred definitions.

Particular preference is given to those compounds of the formula (I) in which each of the radicals have the above-mentioned particularly preferred definitions.

Very particular preference is given to those compounds of the formula (I) in which each of the radicals have the above-mentioned very particularly preferred definitions.

In one embodiment of the invention within the compounds of formula (I) $Hal^1$ and $Hal^2$ each represent fluorine.

In one embodiment of the invention within the compounds of formula (I) $Hal^1$ represents fluorine and $Hal^2$ represents chlorine.

In one embodiment of the invention within the compounds of formula (I) $R^1$, $R^2$, $R^3$, $R^4$, $R^5$ and $R^6$ all represent hydrogen and $R^7$ and $R^8$ both represent methyl.

In one embodiment of the invention within the compounds of formula (I) $R^2$, $R^3$, $R^4$, $R^5$ and $R^6$ all represent hydrogen and $R^1$, $R^7$ and $R^8$ all represent methyl.

If appropriate, the compounds according to the invention can be present as mixtures of different possible isomeric forms, in particular of stereoisomers, such as, for example, E and Z, threo and erythro, and also optical isomers, and, if appropriate, also of tautomers. What is claimed are both the E and the Z isomers, and also the threo and erythro, and the optical isomers, any mixtures of these isomers, and the possible tautomeric forms.

If appropriate, the compounds of the present invention can exist in one or more optical or chiral isomer forms depending on the number of asymmetric centres in the compound. The invention thus relates equally to all the optical isomers and to their racemic or scalemic mixtures (the term "scalemic" denotes a mixture of enantiomers in different proportions) and to the mixtures of all the possible stereoisomers, in all proportions. The diastereoisomers and/or the optical isomers can be separated according to the methods which are known per se by the man ordinary skilled in the art.

If appropriate, the compounds of the present invention can also exist in one or more geometric isomer forms depending on the number of double bonds in the compound. The invention thus relates equally to all geometric isomers and to all possible mixtures, in all proportions. The geometric isomers can be separated according to general methods, which are known per se by the man ordinary skilled in the art.

If appropriate, the compounds of the present invention can also exist in one or more geometric isomer forms depending on the relative position (syn/anti or cis/trans) of the substituents of ring B. The invention thus relates equally to all syn/anti (or cis/trans) isomers and to all possible syn/anti (or cis/trans) mixtures, in all proportions. The syn/anti (or cis/trans) isomers can be separated according to general methods, which are known per se by the man ordinary skilled in the art.

Illustration of the Processes and Intermediates

Carboxamides of the formula (I-a), i.e. carboxamides of formula (I) wherein T represents oxygen, are obtained when carbonyl halides or acids of formula (II) are reacted with amines of formula (III-a) if appropriate in the presence of a coupling agent, if appropriate in the presence of an acid binder and if appropriate in the presence of a diluent [Process (a)]:

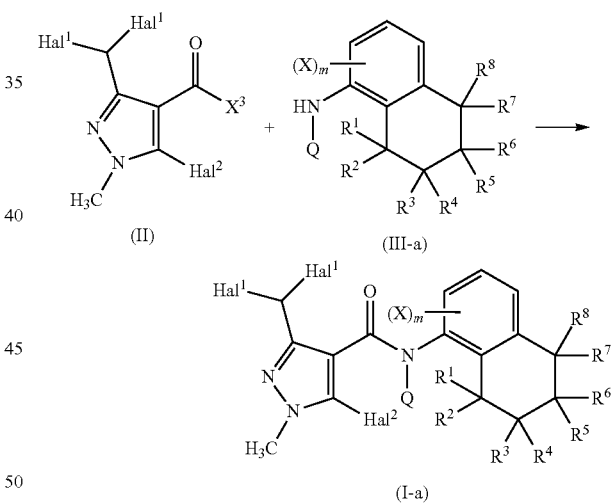

The formula (II) provides a general definition of the carbonyl halides or acids required as starting materials for carrying out the Process (a) according to the invention.

In this formula (II) $Hal^1$ and $Hal^e$ have generally and preferably those meanings which have already been mentioned for these radicals in connection with the description of the compounds of the formula (I). $X^3$ represents halogen, hydroxyl or an activated hydroxyl group, preferably represents fluorine, chlorine or hydroxyl, particularly preferably chlorine or hydroxyl.

An activated hydroxyl group shall mean that the hydroxyl forms together with the adjacent carbonyl an ester which spontaneously reacts with an amino group. Common activated esters include p-nitrophenyl, pentafluoro-phenyl and succinimido esters.

The carbonyl halides or acids of the formula (II) can be prepared from commercially available starting material using known procedures (cf. R. C. Larock *Comprehensive organic transformations*, 1989, VCH publishers).

The formula (III-a) provides a general definition of the amines required as starting materials for carrying out the Process (a) according to the invention.

In this formula (III-a) Q, X, m, $R^1$, $R^2$, $R^3$, $R^4$, $R^5$, $R^6$, $R^7$ and $R^8$ have generally, preferably, particularly preferably, very particularly preferably those meanings which have already been mentioned for these radicals in connection with the description of the compounds of the formula (I).

Thiocarboxamides of the formula (I-b), i.e. carboxamides of formula (I) wherein T represents sulfur, are obtained when carboxamides of the formula (I-a) are reacted with a thionating agent, optionally in the presence of a diluent and if appropriate in the presence of a catalytic or stoichiometric or more quantity of a base [Process (b)]:

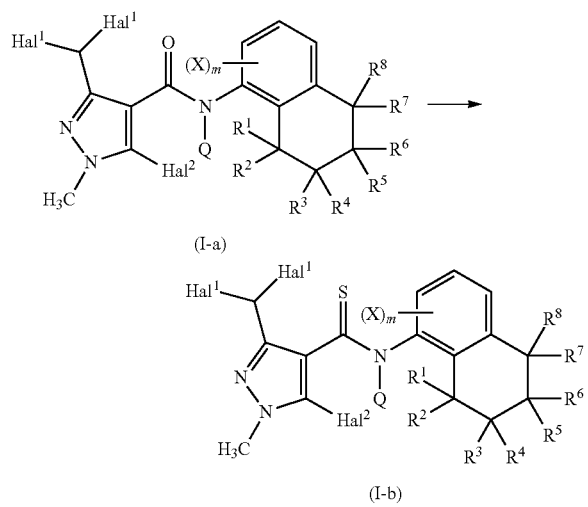

Compounds of formula (III-a) used as starting materials are prepared by known methods (Fragrance chemistry: the science of the sense of smell/edited by Ernst T. Theimer—Synthetic Benzenoid Musks by T. W. Wood; Chemistry—A European Journal, 8(4), 853-858; 2002; Tetrahedron, 59(37), 7389-7395; 2003; Journal of Medicinal Chemistry, 48(1), 71-90; 2005; Bioorganic & Medicinal Chemistry Letters, 18(6), 1830-1834; 2008), are commercially available or can be prepared by reacting bromides of formula (III-b) with tert-butyl carbamates of formula (IV) in the presence of a catalyst, optionally in the presence of an acid binder, in the presence of a diluent followed by treatment with a suitable acid [Process (c)]:

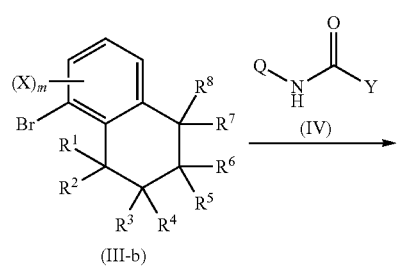

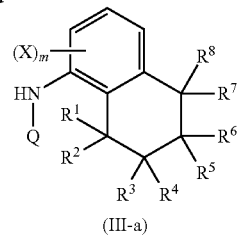

The formula (III-b) provides a general definition of the bromides required as starting materials for carrying out the Process (c) according to the invention.

In this formula (III-b) Q, X, m, $R^1$, $R^2$, $R^3$, $R^4$, $R^5$, $R^6$, $R^7$ and $R^8$ have generally, preferably, particularly preferably, very particularly preferably those meanings which have already been mentioned for these radicals in connection with the description of the compounds of the formula (I).

In formula (IV) Q has generally, preferably, particularly preferably, very particularly preferably those meanings which have already been mentioned for these radicals in connection with the description of the compounds of the formula (I). Y represents hydrogen, $C_1$-$C_6$ alkyl, $C_1$-$C_6$ alkyloxy, phenoxy, benzyloxy.

Compounds of formula (III-b) used as starting materials are prepared by known methods (Fragrance chemistry: the science of the sense of smell/edited by Ernst T. Theimer—Synthetic Benzenoid Musks by T. W. Wood; Chemistry—A European Journal, 8(4), 853-858; 2002; Tetrahedron, 59(37), 7389-7395; 2003; Journal of Medicinal Chemistry, 48(1), 71-90; 2005; Bioorganic & Medicinal Chemistry Letters, 18(6), 1830-1834; 2008; U.S. Pat. No. 5,521,317, WO 2010/109301) or are commercially available.

The amines of the formula (III-a) are also obtained according to the following schemes [Process (d)]:

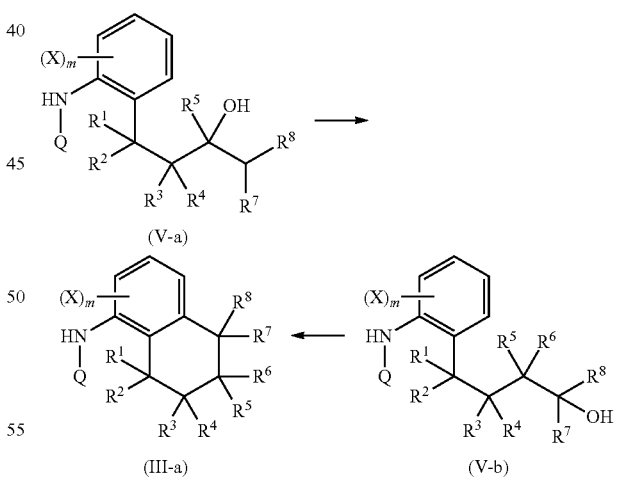

In these formulas (V-a) and (V-b) Q, X, m, $R^1$, $R^2$, $R^3$, $R^4$, $R^5$, $R^6$, $R^7$ and $R^8$ Compounds of formula (V-a) and (V-b) used as starting materials are prepared by known methods.

Suitable diluents for carrying out the Processes (a), (b), (c), and (d) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decaline; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisol; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; their mixtures with water or pure water.

The Process (a) according to the invention is, if appropriate, carried out in the presence of a suitable acid binder when $X^3$ represents halogen. Suitable acid binders are all customary inorganic or organic bases. These preferably include alkaline earth metal or alkali metal hydrides, hydroxides, amides, alkoholates, acetates, carbonates or bicarbonates, such as, for example, sodium hydride, sodium amide, lithium diisopropylamide, sodium meth-oxide, sodium ethoxide, potassium tert-butoxide, sodium hydroxide, potassium hydroxide, sodium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The Process (a) according to the invention is, if appropriate, carried out in the presence of a suitable coupling agent when $X^3$ represents hydroxyl. Suitable coupling agents are all customary carbonyl activators. These preferably include N-[3-(dimethylamino)propyl]-N'-ethyl-carbodiimide-hydrochloride, N,N'-di-sec-butylcarbodiimide, N,N'-dicyclohexykarbodiimide, N,N'-diisopropylcarbodiimide, 1-(3-(dimethylamino)propyl)-3-ethykarbodiimide me-thiodide, 2-bromo-3-ethyl-4-methylthiazolium tetrafluoroborate, N,N-bis[2-oxo-3-oxazolidinyl]phosphorodiamidic chloride, chlorotripyrrolidinophosphonium hexafluorophosphate, bromtripyrrolidinophosphonium hexafluorophosphate, O-(1H-benzotriazol-1-yloxy)tris(dimethylamino)phosphonium hexafluorophosphate, O-(1H-benzotriazol-1-yl)-N,N,N',N'-tetramethyluronium hexafluorophosphate, O-(1H-benzotriazol-1-yl)-N,N,N',N'-bis(tetramethylene)uronium hexafluorophosphate, O-(1H-benzotriazol-1-yl)-N,N,N',N'-bis(tetramethylene)uronium tetrafluoroborate, N,N,N',N'-bis(tetramethylene)chlorouronium tetrafluoroborate, O-(7-azabenzotriazol-1-yl)-N,N,N,N-tetramethyluronium hexafluorophosphate and 1-hydroxybenzotriazole. These reagents can be employed separately, but also in combination.

When carrying out the Process (a) according to the invention, the reaction temperatures can be varied within a relatively wide range. In general, the process is carried out at temperatures of from 0° C. to 150° C., preferably at temperatures of from 20° C. to 110° C.

For carrying out the Process (a) according to the invention for preparing the compounds of the formula (I-a) in general from 0.2 to 5 mol, preferably from 0.5 to 2 mol, of amine of the formula (III-a) are employed per mole of the carbonyl halide or acid of the formula (II). Work-up is carried out by customary methods.

For carrying out the Process (b) according to the invention for preparing the compounds of the formula (I-b) starting amide derivatives of formula (I-a) can be prepared according to Process (a).

Suitable thionating agents for carrying out Process (b) according to the invention can be sulfur (S), sulfhydric acid ($H_2S$), sodium sulfide ($Na_2S$), sodium hydrosulfide (NaHS), boron trisulfide ($B_2S_3$), bis(diethylaluminium) sulfide (($AlEt_2)_2S$), ammonium sulfide (($NH_4)_2S$), phosphorous pentasulfide ($P_2S_5$), Lawesson's reagent (2,4-bis(4-methoxyphenyl)-1,2,3,4-dithiadiphosphetane 2,4-disulfide) or a polymer-supported thionating reagent such as described in *J. Chem. Soc., Perkin* 1 2001, 358.

Process (c) is performed in the presence of a catalyst, optionally in the presence of an acid binder, optionally in the presence of a diluent and followed by treatment with a suitable acid.

Suitable acids for this purpose are chosen amongst usual Brønsted acids such as for example HCl, $H_2SO_4$, $KHSO_4$, AcOH, trifluoroacetic acid, p-toluenesulfonic acid, camphorsulfonic acid, triethanolamine-HCl, Pyridine HCl.

Suitable catalysts for carrying out processes (c) and (d) according to the invention may be chosen from metal salt or complex. Suitable metal derivatives for this purpose are based on palladium or copper. Suitable metal salts or complexes for this purpose are palladium chloride, palladium acetate, tetrakis(triphenylphosphine)palladium, bis(triphenylphosphine)palladium dichloride or 1,1'-bis(diphenylphosphino)ferrocenepalladium(II) chloride, copper iodide, copper bromide, copper thiophene carboxylate, copper trifluoromethane sulfonate, copper (I) oxide It is also possible to generate a palladium complex in the reaction mixture by separate addition to the reaction of a palladium salt and a ligand or salt, such as a phosphine, for example triethylphosphine, tri-tert-butylphosphine, tri-cyclohexylphosphine, 2-(dicyclohexylphosphine)biphenyl, 2-(di-tert-butylphosphin)biphenyl, 2-(dicyclohexylphosphine)-2'-(N,N-dimethylamino)-biphenyl, triphenylphosphine, tris-(o-tolyl)phosphine, sodium 3-(diphenylphosphino)benzolsulfonate, tris-2-(methoxyphenyl)phosphine, 2,2'-bis-(diphenylphosphine)-1,1'-binaphthyl, 1,4-bis-(diphenylphosphine)butane, 1,2-bis-(diphenylphosphine)ethane, 1,4-bis-(dicyclohexylphosphine) butane, 1,2-bis-(dicyclohexylphosphine)ethane, 2-(dicyclohexylphosphine)-2'-(N,N-dimethylamino)-biphenyl, bis(diphenylphosphino)ferrocene, tris-(2,4-tert-butylphenyl)-phosphite, (R)-(−)-1-[(S)-2-(diphenylphosphino)ferrocenyl]ethyldi-tert-butylphosphine, (S)-(+)-1-[(R)-2-(diphenylphosphino)ferrocenyl]-ethyldicyclohexylphosphine, (R)-(−)-1-[(S)-2-(diphenylphosphino)ferrocenyl]ethyldicyclohexylphosphine, (S)-(+)-1-[(R)-2-(diphenylphosphino)ferrocenyl]ethyldi-t-butylphosphine or 1,3-bis(2,4,6-trimethylphenyl)imidazolium chloride.

It is also possible to generate a copper complex in the reaction mixture by separate addition to the reaction of a copper salt and a ligand or salt, such as a diamine for example cyclohexyl 1,2-diamine, N,N'-dimethylethylene diamine, cyclohexyl N,N'-dimethylamine.

It is also advantageous to choose the appropriate catalyst and/or ligand from commercial catalogues such as "Metal Catalysts for Organic Synthesis" by Strem Chemicals or "Phosphorous Ligands and Compounds" by Strem Chemicals.

When carrying out the Process (c) according to the invention, the reaction temperatures can be varied within a relatively wide range. In general, the process is carried out at temperatures of from 0° C. to 150° C., preferably at temperatures of from 20° C. to 110° C.

For carrying out the Process (c) according to the invention for preparing the compounds of the formula (III-a) in general from 0.2 to 5 mol, preferably from 0.5 to 2 mol, of compound of the formula (IV) are employed per mole of bromides of the formula (III-b). Work-up is carried out by customary methods.

When carrying out the Process (d) according to the invention, the reaction temperatures can be varied within a relatively wide range. In general, the process is carried out at temperatures of from 0° C. to 150° C., preferably at temperatures of from 60° C. to 140° C.

For carrying out the Process (d) according to the invention for preparing the compounds of the formula (I-a) in general from 0.2 to 5 mol, preferably from 0.5 to 2 mol, of compound of the formula (V) are employed per mole of the bromides of the formula (III-b). Work-up is carried out by customary methods.

Suitable bases for carrying out the processes (b) according to the invention can be inorganic and organic bases which are customary for such reactions. Preference is given to using alkaline earth metal, alkali metal hydride, alkali metal hydroxides or alkali metal alkoxides, such as sodium hydroxide, sodium hydride, calcium hydroxide, potassium hydroxide, potassium tert-butoxide or other ammonium hydroxide, alkali metal carbonates, such as sodium carbonate, potassium carbonate, potassium bicarbonate, sodium bicarbonate, cesium carbonate, alkali metal or alkaline earth metal acetates, such as sodium acetate, potassium acetate, calcium acetate, and also tertiary amines, such as trimethylamine, triethylamine, diisopropylethylamine, tributylamine, N,N-dimethylaniline, pyridine, N-methylpiperidine, N,N-dimethylaminopyridine, 1,4-diazabicyclo[2.2.2]octane (DABCO), 1,5-diazabicyclo[4.3.0]non-5-ene (DBN) or 1,8-diazabicyclo[5.4.0]undec-7-ene (DBU).

Suitable acid binders for carrying out the processes (a), (c), and (d) according to the invention can be inorganic and organic bases which are customary for such reactions. Preference is given to using alkaline earth metal, alkali metal hydride, alkali metal hydroxides or alkali metal alkoxides, such as sodium hydroxide, sodium hydride, calcium hydroxide, potassium hydroxide, potassium tert-butoxide or other ammonium hydroxide, alkali metal carbonates, such as sodium carbonate, potassium carbonate, potassium bicarbonate, sodium bicarbonate, cesium carbonate, alkali metal or alkaline earth metal acetates, such as sodium acetate, potassium acetate, calcium acetate, and also tertiary amines, such as trimethylamine, triethylamine, diisopropylethylamine, tributylamine, N,N-dimethylaniline, pyridine, N-methylpiperidine, N,N-dimethylaminopyridine, 1,4-diazabicyclo[2.2.2]octane (DABCO), 1,5-diazabicyclo[4.3.0]non-5-ene (DBN) or 1,8-diazabicyclo[5.4.0]undec-7-ene (DBU).

The present invention also describes novel intermediates being compounds according to formula (III-a)

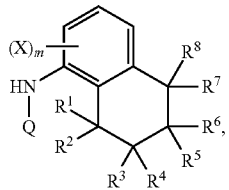

(III-a)

wherein
Q represents hydrogen;
X represents fluorine;
m represents 0 or 1;
$R^1$, $R^2$, $R^3$, $R^4$, $R^5$, $R^6$, $R^7$ and $R^8$ independently from each other represent hydrogen or methyl;
$R^7$ and $R^8$ form the group $=C(Y^1)Y^2$ (where $Y^1$ and $Y^2$ independently of one another represent hydrogen or a group $=N-O-R^c$ (where $R^c$ represents methyl or ethyl).

The Processes (a), (b), (c) and (d) are generally carried out under atmospheric pressure. However, it is also possible to operate under elevated or reduced pressure—in general between 0.1 bar and 10 bar.

Composition/Formulation

The present invention further relates to a crop protection composition for controlling unwanted microorganisms, especially unwanted fungi and bacteria, comprising an effective and non-phytotoxic amount of the inventive active ingredients. These are preferably fungicidal compositions which comprise agriculturally suitable auxiliaries, solvents, carriers, surfactants or extenders.

In the context of the present invention, "control of harmful microorganisms" means a reduction in infestation by harmful microorganisms, compared with the untreated plant measured as fungicidal efficacy, preferably a reduction by 25-50%, compared with the untreated plant (100%), more preferably a reduction by 40-79%, compared with the untreated plant (100%); even more preferably, the infection by harmful microorganisms is entirely sup-pressed (by 70-100%). The control may be curative, i.e. for treatment of already infected plants, or protective, for protection of plants which have not yet been infected.

An "effective but non-phytotoxic amount" means an amount of the inventive composition which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on several factors, for example on the fungus to be controlled, the plant, the climatic conditions and the ingredients of the inventive compositions.

Suitable organic solvents include all polar and non-polar organic solvents usually employed for formulation purposes. Preferable the solvents are selected from ketones, e.g. methyl-isobutyl-ketone and cyclohexanone, amides, e.g. dimethyl formamide and alkanecarboxylic acid amides, e.g. N,N-dimethyl decaneamide and N,N-dimethyl octanamide, furthermore cyclic solvents, e.g. N-methyl-pyrrolidone, N-octyl-pyrrolidone, N-dodecyl-pyrrolidone, N-octyl-caprolactame, N-dodecyl-caprolactame and butyrolactone, furthermore strong polar solvents, e.g. dimethylsulfoxide, and aromatic hydrocarbons, e.g. xylol, Solvesso™, mineral oils, e.g. white spirit, petroleum, alkyl benzenes and spindle oil, also esters, e.g. propyleneglycol-monomethylether acetate, adipic acid dibutylester, acetic acid hexylester, acetic acid heptylester, citric acid tri-n-butylester and phthalic acid di-n-butylester, and also alcohols, e.g. benzyl alcohol and 1-methoxy-2-propanol.

According to the invention, a carrier is a natural or synthetic, organic or inorganic substance with which the active ingredients are mixed or combined for better applicability, in particular for application to plants or plant parts or seed. The carrier, which may be solid or liquid, is generally inert and should be suitable for use in agriculture.

Useful solid or liquid carriers include: for example ammonium salts and natural rock dusts, such as kaolins, clays, talc, chalk, quartz, attapulgite, montmorillonite or diatomaceous earth, and synthetic rock dusts, such as finely divided silica, alumina and natural or synthetic silicates, resins, waxes, solid fertilizers, water, alcohols, especially butanol, organic solvents, mineral and vegetable oils, and derivatives thereof. Mixtures of such carriers can likewise be used.

Suitable solid filler and carrier include inorganic particles, e.g. carbonates, silikates, sulphates and oxides with an average particle size of between 0.005 and 20 μm, preferably of between 0.02 to 10 μm, for example ammonium sulphate, ammonium phosphate, urea, calcium carbonate, calcium sulphate, magnesium sulphate, magnesium oxide, aluminium oxide, silicium dioxide, so-called fine-particle silica, silica gels, natural or synthetic silicates, and alumosilicates and plant products like cereal flour, wood powder/sawdust and cellulose powder.

Useful solid carriers for granules include: for example crushed and fractionated natural rocks such as calcite, marble, pumice, sepiolite, dolomite, and synthetic granules of inorganic and organic meals, and also granules of organic material such as sawdust, coconut shells, maize cobs and tobacco stalks.

Useful liquefied gaseous extenders or carriers are those liquids which are gaseous at standard temperature and under standard pressure, for example aerosol propellants such as halohydrocarbons, and also butane, propane, nitrogen and carbon dioxide.

In the formulations, it is possible to use tackifiers such as carboxymethylcellulose, and natural and synthetic polymers in the form of powders, granules or latices, such as gum arabic, polyvinyl alcohol and polyvinyl acetate, or else natural phospholipids, such as cephalins and lecithins, and synthetic phospholipids. Further additives may be mineral and vegetable oils.

If the extender used is water, it is also possible to employ, for example, organic solvents as auxiliary solvents. Useful liquid solvents are essentially: aromatics such as xylene, toluene or alkylnaphthalenes, chlorinated aromatics and chlorinated aliphatic hydrocarbons such as chlorobenzenes, chloroethylenes or dichloromethane, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

Suitable surfactants (adjuvants, emulsifiers, dispersants, protective colloids, wetting agent and adhesive) include all common ionic and non-ionic substances, for example ethoxylated nonylphenols, polyalkylene glycolether of linear or branched alcohols, reaction products of alkyl phenols with ethylene oxide and/or propylene oxide, reaction products of fatty acid amines with ethylene oxide and/or propylene oxide, furthermore fattic acid esters, alkyl sulfonates, alkyl sulphates, alkyl ethersulphates, alkyl etherphosphates, arylsulphate, ethoxylated arylalkylphenols, e.g. tristyryl-phenol-ethoxylates, furthermore ethoxylated and propoxylated arylalkylphenols like sulphated or phosphated arylalkylphenol-ethoxylates and -ethoxy- and -propoxylates. Further examples are natural and synthetic, water soluble polymers, e.g. lignosulphonates, gelatine, gum arabic, phospholipides, starch, hydrophobic modified starch and cellulose derivatives, in particular cellulose ester and cellulose ether, further polyvinyl alcohol, polyvinyl acetate, polyvinyl pyrrolidone, polyacrylic acid, polymethacrylic acid and co-polymerisates of (meth)acrylic acid and (meth)acrylic acid esters, and further co-polymerisates of methacrylic acid and methacrylic acid esters which are neutralized with alkalimetal hydroxide and also condensation products of optionally substituted naphthalene sulfonic acid salts with formaldehyde. The presence of a surfactant is necessary if one of the active ingredients and/or one of the inert carriers is insoluble in water and when application is effected in water. The proportion of surfactants is between 5 and 40 percent by weight of the inventive composition.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Antifoams which may be present in the formulations include e.g. silicone emulsions, longchain alcohols, fattiy acids and their salts as well as fluoroorganic substances and mixtures thereof.

Examples of thickeners are polysaccharides, e.g. xanthan gum or veegum, silicates, e.g. attapulgite, bentonite as well as fine-particle silica.

If appropriate, it is also possible for other additional components to be present, for example protective colloids, binders, adhesives, thickeners, thixotropic substances, penetrants, stabilizers, sequestrants, complexing agents.

In general, the active ingredients can be combined with any solid or liquid additive commonly used for formulation purposes.

The inventive active ingredients or compositions can be used as such or, depending on their particular physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, gas (under pressure), gas generating product, foams, pastes, pesticide coated seed, suspension concentrates, suspoemulsion concentrates, soluble concentrates, suspensions, wettable powders, soluble powders, dusts and granules, water-soluble and water-dispersible granules or tablets, water-soluble and water-dispersible powders for the treatment of seed, wettable powders, natural products and synthetic substances impregnated with active ingredient, and also microencapsulations in polymeric substances and in coating materials for seed, and also ULV cold-fogging and warm-fogging formulations.

The inventive compositions include not only formulations which are already ready for use and can be applied with a suitable apparatus to the plant or the seed, but also commercial concentrates which have to be diluted with water prior to use. Customary applications are for example dilution in water and subsequent spraying of the resulting spray liquor, application after dilution in oil, direct application without dilution, seed treatment or soil application of granules.

The inventive compositions and formulations generally contain between 0.05 and 99% by weight, 0.01 and 98% by weight, preferably between 0.1 and 95% by weight, more preferably between 0.5 and 90% of active ingredient, most preferably between 10 and 70% by weight. For special applications, e.g. for protection of wood and de-rived timber products the inventive compositions and formulations generally contain between 0.0001 and 95% by weight, preferably 0.001 to 60% by weight of active ingredient.

The contents of active ingredient in the application forms prepared from the commercial formulations may vary in a broad range. The concentration of the active ingredients in the application forms is generally between 0.000001 to 95% by weight, preferably between 0.0001 and 2% by weight.

The formulations mentioned can be prepared in a manner known per se, for example by mixing the active ingredients with at least one customary extender, solvent or diluent, adjuvant, emulsifier, dispersant, and/or binder or fixative, wetting agent, water repellent, if appropriate desiccants and UV stabilizers and, if appropriate, dyes and pigments, antifoams, preservatives, inorganic and organic thickeners, adhesives, gibberellins and also further processing auxiliaries and also water. Depending on the formulation type to be prepared further processing steps are necessary, e.g. wet grinding, dry grinding and granulation.

The inventive active ingredients may be present as such or in their (commercial) formulations and in the use forms prepared from these formulations as a mixture with other (known) active ingredients, such as insecticides, attractants, sterilants, bactericides, acaricides, nematicides, fungicides, growth regulators, herbicides, fertilizers, safeners and/or semiochemicals.

The inventive treatment of the plants and plant parts with the active ingredients or compositions is effected directly or by action on their surroundings, habitat or storage space by the customary treatment methods, for example by dipping, spraying, atomizing, irrigating, evaporating, dusting, fogging, broadcasting, foaming, painting, spreading-on, watering (drenching), drip irrigating and, in the case of propagation material, especially in the case of seeds, also by dry seed treatment, wet seed treatment, slurry treatment, incrustation, coating with one or more coats, etc. It is also possible to deploy the active ingredients by the ultra-low volume method or to inject the active ingredient preparation or the active ingredient itself into the soil.

Plant/Crop Protection

The inventive active ingredients or compositions have potent microbicidal activity and can be used for control of unwanted microorganisms, such as fungi and bacteria, in crop protection and in the protection of materials.

The invention also relates to a method for controlling unwanted microorganisms, characterized in that the inventive active ingredients are applied to the phytopathogenic fungi, phytopathogenic bacteria and/or their habitat. Fungicides can be used in crop protection for control of phytopathogenic fungi. They are characterized by an out-standing efficacy against a broad spectrum of phytopathogenic fungi, including soilborne pathogens, which are in particular members of the classes *Plasmodiophoromycetes, Peronosporomycetes* (Syn. *Oomycetes*), *Chytridiomycetes, Zygomycetes, Ascomycetes, Basidiomycetes and Deuteromycetes* (Syn. *Fungi impeifecti*). Some fungicides are systemically active and ca be used in plant protection as foliar, seed dressing or soil fungicide. Furthermore, they are suitable for combating fungi, which inter alia infest wood or roots of plant.

Bactericides can be used in crop protection for control of Pseudomonadaceae, Rhizobiaceae, Enterobacteriaceae, Corynebacteriaceae and Streptomycetaceae.

Non-limiting examples of pathogens of fungal diseases which can be treated in accordance with the invention include:

diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; *Uncinula* species, for example *Uncinula necator*;

diseases caused by rust disease pathogens, for example *Gymnosporangium* species, for example *Gymnosporangium sabinae*; *Hemileia* species, for example *Hemileia vastatrix*; *Phakopsora* species, for example *Phakopsora pachyrhizi* and *Phakopsora meibomiae*; *Puccinia* species, for example *Puccinia recondite, P. triticina, P. graminis* or *P. striiformis*; *Uromyces* species, for example *Uromyces appendiculatus*;

diseases caused by pathogens from the group of the Oomycetes, for example *Albugo* species, for example *Algubo candida*; *Bremia* species, for example *Bremia lactucae*; *Peronospora* species, for example *Peronospora pisi* or *P. brassicae*; *Phytophthora* species, for example *Phytophthora infestans*; *Plasmopara* species, for example *Plasmopara viticola*; *Pseudoperonospora* species, for example *Pseudoperonospora humuli* or *Pseudoperonospora cubensis*; *Pythium* species, for example *Pythium ultimum*;

leaf blotch diseases and leaf wilt diseases caused, for example, by *Alternaria* species, for example *Alternaria solani*; *Cercospora* species, for example *Cercospora beticola*; *Cladiosporium* species, for example *Cladiosporium cucumerinum*; *Cochliobolus* species, for example *Cochliobolus sativus* (conidia form: *Drechslera,* Syn: *Helminthosporium*), *Cochliobolus miyabeanus*; *Colletotrichum* species, for example *Colletotrichum lindemuthanium*; *Cycloconium* species, for example *Cycloconium oleaginum*; *Diaporthe* species, for example *Diaporthe citri*; *Elsinoe* species, for example *Elsinoe fawcettii*; *Gloeosporium* species, for example *Gloeosporium laeticolor*; *Glomerella* species, for example *Glomerella cingulata*; *Guignardia* species, for example *Guignardia bidwelli*; *Leptosphaeria* species, for example *Leptosphaeria maculans, Leptosphaeria nodorum*; *Magnaporthe* species, for example *Magnaporthe grisea*; *Microdochium* species, for example *Microdochium nivale*; *Mycosphaerella* species, for example *Mycosphaerella graminicola, M. arachidicola* and *M. fijiensis*; *Phaeosphaeria* species, for example *Phaeosphaeria nodorum*; *Pyrenophora* species, for example *Pyrenophora teres, Pyrenophora tritici* repentis; *Ramularia* species, for example *Ramularia collo-cygni, Ramularia areola*; *Rhynchosporium* species, for example *Rhynchosporium secalis*; *Septoria* species, for example *Septoria apii, Septoria lycopersii*; *Typhula* species, for example *Typhula incarnate*; *Venturia* species, for example *Venturia inaequalis*;

root and stem diseases caused, for example, by *Corticium* species, for example *Corticium graminearum*; *Fusarium* species, for example *Fusarium oxysporum*; *Gaeumannomyces* species, for example *Gaeumannomyces graminis*; *Rhizoctonia* species, such as, for example *Rhizoctonia solani*; *Sarocladium* diseases caused for example by *Sarocladium oryzae*; *Sclerotium* diseases caused for example by *Sclerotium oryzae*; *Tapesia* species, for example *Tapesia acuformis*; *Thielaviopsis* species, for example *Thielaviopsis basicola*;

ear and panicle diseases (including corn cobs) caused, for example, by *Alternaria* species, for example *Alternaria* spp.; *Aspergillus* species, for example *Aspergillus flavus*; *Cladosporium* species, for example *Cladosporium cladosporioides*; *Claviceps* species, for example *Claviceps purpurea*; *Fusarium* species, for example *Fusarium culmorum*; *Gibberella* species, for example *Gibberella zeae*; *Monographella* species, for example *Monographella nivalis*; *Septoria* species, for example *Septoria nodorum*;

diseases caused by smut fungi, for example *Sphacelotheca* species, for example *Sphacelotheca reiliana*; *Tilletia* species, for example *Tilletia caries, T. controversa*; *Urocystis* species, for example *Urocystis occulta*; *Ustilago* species, for example *Ustilago nuda, U. nuda tritici*;

fruit rot caused, for example, by *Aspergillus* species, for example *Aspergillus flavus*; *Botrytis* species, for example *Botrytis cinerea*; *Penicillium* species, for example *Penicillium expansum* and *P. purpurogenum*; *Sclerotinia* species, for example *Sclerotinia sclerotiorum*; *Verticilium* species, for example *Verticilium alboatrum*;

seed and soilborne decay, mould, wilt, rot and damping-off diseases caused, for example, by *Alternaria* species, caused for example by *Alternaria brassicicola; Aphanomyces* species, caused for example by *Aphanomyces euteiches; Ascochyta* species, caused for example by *Ascochyta lentis; Aspergillus* species, caused for example by *Aspergillus flavus; Cladosporium* species, caused for example by *Cladosporium herbarum; Cochliobolus* species, caused for example by *Cochliobolus sativus*; (Conidiaform: *Drechslera, Bipolaris* Syn: *Helminthosporium*); *Colletotrichum* species, caused for example by *Colletotrichum coccodes; Fusarium* species, caused for example by *Fusarium culmorum; Gibberella* species, caused for example by *Gibberella zeae; Macrophomina* species, caused for example by *Macrophomina phaseolina; Monographella* species, caused for example by *Monographella nivalis; Penicillium* species, caused for example by *Penicillium expansum; Phoma* species, caused for example by *Phoma lingam; Phomopsis* species, caused for example by *Phomopsis sojae; Phytophthora* species, caused for example by *Phytophthora cactorum; Pyrenophora* species, caused for example by *Pyrenophora graminea; Pyricularia* species, caused for example by *Pyricularia oryzae; Pythium* species, caused for example by *Pythium ultimum; Rhizoctonia* species, caused for example by *Rhizoctonia solani; Rhizopus* species, caused for example by *Rhizopus oryzae; Sclerotium* species, caused for example by *Sclerotium rolfsii; Septoria* species, caused for example by *Septoria nodorum; Typhula* species, caused for example by *Typhula incarnate; Verticillium* species, caused for example by *Verticillium dahliae;* cancers, galls and witches' broom caused, for example, by *Nectria* species, for example *Nectria galligena*; wilt diseases caused, for example, by *Monilinia* species, for example *Monilinia laxa;* leaf blister or leaf curl diseases caused, for example, by *Exobasidium* species, for example *Exobasidium vexans; Taphrina* species, for example *Taphrina deformans;* decline diseases of wooden plants caused, for example, by Esca disease, caused for example by *Phaemoniella clamydospora, Phaeoacremonium aleophilum* and *Fomitiporia mediterranea; Eutypa* dyeback, caused for example by *Eutypa lata; Ganoderma* diseases caused for example by *Ganoderma boninense; Rigidoporus* diseases caused for example by *Rigidoporus lignosus;* diseases of flowers and seeds caused, for example, by *Botrytis* species, for example *Botrytis cinerea;* diseases of plant tubers caused, for example, by *Rhizoctonia* species, for example *Rhizoctonia solani; Helminthosporium* species, for example *Helminthosporium solani;*

Club root caused, for example, by *Plasmodiophora* species, for example *Plamodiophora brassicae;* diseases caused by bacterial pathogens, for example *Xanthomonas* species, for example *Xanthomonas campestris* pv. *oryzae; Pseudomonas* species, for example *Pseudomonas syringae* pv. *lachrymans; Erwinia* species, for example *Erwinia amylovora.*

The following diseases of soya beans can be controlled with preference:

Fungal diseases on leaves, stems, pods and seeds caused, for example, by *Alternaria* leaf spot (*Alternaria* spec. *atrans tenuissima*), Anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera* trispora (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), *fusarium* blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The inventive fungicidal compositions can be used for curative or protective/preventive control of phytopathogenic fungi. The invention therefore also relates to curative and protective methods for controlling phytopathogenic fungi by the use of the inventive active ingredients or compositions, which are applied to the seed, the plant or plant parts, the fruit or the soil in which the plants grow.

The fact that the active ingredients are well tolerated by plants at the concentrations required for controlling plant diseases allows the treatment of above-ground parts of plants, of propagation stock and seeds, and of the soil.

According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

The inventive active ingredients, when they are well tolerated by plants, have favourable homeotherm toxicity and are well tolerated by the environment, are suitable for protecting plants and plant organs, for enhancing harvest yields, for improving the quality of the harvested material. They can preferably be used as crop protection compositions. They are active against normally sensitive and resistant species and against all or some stages of development.

Plants which can be treated in accordance with the invention include the following main crop plants: maize, soya bean, alfalfa, cotton, sunflower, *Brassica* oil seeds such as *Brassica napus* (e.g. canola, rapeseed), *Brassica rapa, B. juncea* (e.g. (field) mustard) and *Brassica carinata, Arecaceae* sp. (e.g. oilpalm, coconut), rice, wheat, sugar beet, sugar cane, oats, rye, barley, millet and sorghum, triticale, flax, nuts, grapes and vine and various fruit and vegetables from various botanic taxa, e.g. *Rosaceae* sp. (e.g. pome fruits such as apples and pears, but also stone fruits such as apricots, cherries, almonds, plums and peaches, and berry fruits such as strawberries, raspberries, red and black currant and gooseberry), *Ribesioidae* sp., *Juglandaceae* sp., *Betulaceae* sp., *Anacardiaceae* sp., *Fagaceae* sp., *Moraceae* sp., *Oleaceae* sp. (e.g. olive tree), *Actinidaceae* sp., *Lauraceae* sp. (e.g. avocado, cinnamon, camphor), *Musaceae* sp. (e.g. banana trees and plantations), *Rubiaceae* sp. (e.g. coffee), *Theaceae* sp. (e.g. tea), *Sterculiceae* sp., *Rutaceae* sp. (e.g. lemons, oranges, mandarins and grapefruit); *Solanaceae* sp. (e.g. tomatoes, potatoes, peppers, capsicum, aubergines, tobacco), *Liliaceae* sp., *Compositae* sp. (e.g. lettuce, artichokes and chicory—including root chicory, endive or common chicory), *Umbelliferae* sp. (e.g. carrots, parsley, celery and celeriac), *Cucurbitaceae* sp. (e.g. cucumbers—including gherkins, pumpkins, watermelons, calabashes and melons), *Alliaceae* sp. (e.g. leeks and onions), *Cruciferae* sp. (e.g. white cabbage, red cabbage, broccoli, cauliflower, Brussels sprouts, pak choi, kohlrabi, radishes, horseradish, cress and chinese cabbage), *Leguminosae* sp. (e.g. peanuts, peas, lentils and beans—e.g. common beans and broad beans), *Chenopodiaceae* sp. (e.g. Swiss chard, fodder beet, spin-ach, beetroot), *Linaceae* sp. (e.g. hemp), *Cannabeacea* sp. (e.g. *cannabis*), *Malvaceae* sp. (e.g. okra, cocoa), *Papaveraceae* (e.g. poppy), *Asparagaceae* (e.g. asparagus); useful plants and ornamental plants in the garden and woods including turf, lawn, grass and *Stevia rebaudiana*; and in each case genetically modified types of these plants.

Resistance Induction/Plant Health and Other Effects

The active compounds according to the invention also exhibit a potent strengthening effect in plants. Accordingly, they can be used for mobilizing the defences of the plant against attack by undesirable microorganisms.

Plant-strengthening (resistance-inducing) substances are to be understood as meaning, in the present context, those substances which are capable of stimulating the defence system of plants in such a way that the treated plants, when subsequently inoculated with undesirable microorganisms, develop a high degree of resistance to these microorganisms.

The active compounds according to the invention are also suitable for increasing the yield of crops. In addition, they show reduced toxicity and are well tolerated by plants.

Further, in context with the present invention plant physiology effects comprise the following:

Abiotic stress tolerance, comprising temperature tolerance, drought tolerance and recovery after drought stress, water use efficiency (correlating to reduced water consumption), flood tolerance, ozone stress and UV tolerance, tolerance towards chemicals like heavy metals, salts, pesticides (safener) etc.

Biotic stress tolerance, comprising increased fungal resistance and increased resistance against nematodes, viruses and bacteria. In context with the present invention, biotic stress tolerance preferably comprises increased fungal resistance and increased resistance against nematodes Increased plant vigor, comprising plant health/plant quality and seed vigor, reduced stand failure, improved appearance, increased recovery, improved greening effect and improved photosynthetic efficiency.

Effects on plant hormones and/or functional enzymes.

Effects on growth regulators (promoters), comprising earlier germination, better emergence, more developed root system and/or improved root growth, increased ability of tillering, more productive tillers, earlier flowering, increased plant height and/or biomass, shorting of stems, improvements in shoot growth, number of kernels/ear, number of ears/m$^2$, number of stolons and/or number of flowers, enhanced harvest index, bigger leaves, less dead basal leaves, improved phyllotaxy, earlier maturation/earlier fruit finish, homogenous riping, increased duration of grain filling, better fruit finish, bigger fruit/vegetable size, sprouting resistance and reduced lodging.

Increased yield, referring to total biomass per hectare, yield per hectare, kernel/fruit weight, seed size and/or hectoliter weight as well as to increased product quality, comprising:

improved processability relating to size distribution (kernel, fruit, etc.), homogenous riping, grain moisture, better milling, better vinification, better brewing, increased juice yield, harvestability, digestibility, sedimentation value, falling number, pod stability, storage stability, improved fiber length/strength/uniformity, increase of milk and/or meet quality of silage fed animals, adaption to cooking and frying;

further comprising improved marketability relating to improved fruit/grain quality, size distribution (kernel, fruit, etc.), increased storage/shelf-life, firmness/softness, taste (aroma, texture, etc.), grade (size, shape, number of berries, etc.), number of berries/fruits per bunch, crispness, freshness, coverage with wax, frequency of physiological disorders, colour, etc.;

further comprising increased desired ingredients such as e.g. protein content, fatty acids, oil content, oil quality, aminoacid composition, sugar content, acid content (pH), sugar/acid ratio (Brix), polyphenols, starch content, nutritional quality, gluten content/index, energy content, taste, etc.;

and further comprising decreased undesired ingredients such as e.g. less mycotoxins, less aflatoxins, geosmin level, phenolic aromas, lacchase, polyphenol oxidases and peroxidases, nitrate content etc.

Sustainable agriculture, comprising nutrient use efficiency, especially nitrogen (N)-use efficiency, phosphours (P)-use efficiency, water use efficiency, improved transpiration, respiration and/or $CO_2$ assimilation rate, better nodulation, improved Ca-metabolism etc.

Delayed senescence, comprising improvement of plant physiology which is manifested, for example, in a longer grain filling phase, leading to higher yield, a longer duration of green leaf colouration of the plant and thus comprising colour (greening), water content, dryness etc. Accordingly, in the context of the present invention, it has been found that the specific inventive application of the active compound combination makes it possible to prolong the green leaf area duration, which delays the maturation (senescence) of the plant. The main advantage to the farmer is a longer grain filling phase leading to higher yield. There is also an advantage to the farmer on the basis of greater flexibility in the harvesting time.

Therein "sedimentation value" is a measure for protein quality and describes according to Zeleny (Zeleny value) the degree of sedimentation of flour suspended in a lactic acid solution during a standard time interval. This is taken as a measure of the baking quality. Swelling of the gluten fraction of flour in lactic acid solution affects the rate of sedimentation of a flour suspension. Both a higher gluten content and a better gluten quality give rise to slower sedimentation and higher Zeleny test values. The sedimentation value of flour depends on the wheat protein composition and is mostly correlated to the protein content, the wheat hardness, and the volume of pan and hearth loaves. A stronger correlation between loaf volume and Zeleny sedimentation volume compared to SDS sedimentation volume could be due to the protein content influencing both the volume and Zeleny value (*Czech J. Food Sci. Vol.* 21, No. 3: 91-96, 2000).

Further the "falling number" as mentioned herein is a measure for the baking quality of cereals, especially of wheat. The falling number test indicates that sprout damage may have occurred. It means that changes to the physical properties of the starch portion of the wheat kernel has already happened. Therein, the falling number instrument analyzes viscosity by measuring the resistance of a flour and water paste to a falling plunger. The time (in seconds) for this to happen is known as the falling number. The falling number results are recorded as an index of enzyme activity in a wheat or flour sample and results are expressed in time as seconds. A high falling number (for example, above 300 seconds) indicates minimal enzyme activity and sound quality wheat or flour. A low falling number (for example, below 250 seconds) indicates substantial enzyme activity and sprout-damaged wheat or flour.

The term "more developed root system"/"improved root growth" refers to longer root system, deeper root growth, faster root growth, higher root dry/fresh weight, higher root volume, larger root surface area, bigger root diameter, higher root stability, more root branching, higher number of root hairs, and/or more root tips and can be measured by analyzing the root architecture with suitable methodologies and Image analysis programmes (e.g. WinRhizo).

The term "crop water use efficiency" refers technically to the mass of agriculture produce per unit water consumed and economically to the value of product(s) produced per unit water volume consumed and can e.g. be measured in terms of yield per ha, biomass of the plants, thousand-kernel mass, and the number of ears per m2.

The term "nitrogen-use efficiency" refers technically to the mass of agriculture produce per unit nitrogen consumed and economically to the value of product(s) produced per unit nitrogen consumed, reflecting uptake and utilization efficiency.

Improvement in greening/improved colour and improved photosynthetic efficiency as well as the delay of senescence can be measured with well-known techniques such as a HandyPea system (Hansatech). Fv/Fm is a parameter widely used to indicate the maximum quantum efficiency of photosystem II (PSII). This parameter is widely considered to be a selective indication of plant photosynthetic performance with healthy samples typically achieving a maximum Fv/Fm value of approx. 0.85. Values lower than this will be observed if a sample has been exposed to some type of biotic or abiotic stress factor which has reduced the capacity for photochemical quenching of energy within PSII. Fv/Fm is presented as a ratio of variable fluorescence (Fv) over the maximum fluorescence value (Fm). The Performance Index is essentially an indicator of sample vitality. (See e.g. *Advanced Techniques in Soil Microbiology*, 2007, 11, 319-341; *Applied Soil Ecology*, 2000, 15, 169-182.)

The improvement in greening/improved colour and improved photosynthetic efficiency as well as the delay of senescence can also be assessed by measurement of the net photosynthetic rate (Pn), measurement of the chlorophyll content, e.g. by the pigment extraction method of Ziegler and Ehle, measurement of the photochemical efficiency (Fv/Fm ratio), determination of shoot growth and final root and/or canopy biomass, determination of tiller density as well as of root mortality.

Within the context of the present invention preference is given to improving plant physiology effects which are selected from the group comprising: enhanced root growth/more developed root system, improved greening, improved water use efficiency (correlating to reduced water consumption), improved nutrient use efficiency, comprising especially improved nitrogen (N)-use efficiency, delayed senescence and enhanced yield.

Within the enhancement of yield preference is given as to an improvement in the sedimentation value and the falling number as well as to the improvement of the protein and sugar content—especially with plants selected from the group of cereals (preferably wheat).

Preferably the novel use of the fungicidal compositions of the present invention relates to a combined use of a) preventively and/or curatively controlling pathogenic fungi and/or nematodes, with or without resistance management, and b) at least one of enhanced root growth, improved greening, improved water use efficiency, delayed senescence and enhanced yield. From group b) enhancement of root system, water use efficiency and N-use efficiency is particularly preferred.

Seed Treatment

The invention further comprises a method for treating seed.

The invention further relates to seed which has been treated by one of the methods described in the previous paragraph. The inventive seeds are employed in methods for the protection of seed from unwanted microorganisms. In these methods, seed treated with at least one inventive active ingredient is used.

The inventive active ingredients or compositions are also suitable for treating seed. A large part of the damage to crop plants caused by harmful organisms is triggered by the infection of the seed during storage or after sowing, and also during and after germination of the plant. This phase is particularly critical since the roots and shoots of the growing plant are particularly sensitive, and even minor damage may result in the death of the plant. There is therefore a great interest in protecting the seed and the germinating plant by using appropriate compositions.

The control of phytopathogenic fungi by treating the seed of plants has been known for a long time and is the subject of constant improvements. However, the treatment of seed entails a series of problems which cannot always be solved in a satisfactory manner. For instance, it is desirable to develop methods for protecting the seed and the germinating plant, which dispense with, or at least significantly reduce, the additional deployment of crop protection compositions after planting or after emergence of the plants. It is also desirable to optimize the amount of the active ingredient used so as to provide the best possible protection for the seed and the germinating plant from attack by phytopathogenic fungi, but without damaging the plant itself by the active ingredient employed. In particular, methods for the treatment of seed should also take account of the intrinsic fungicidal properties of transgenic plants in order to achieve optimal protection of the seed and the germinating plant with a minimum expenditure of crop protection compositions.

The present invention therefore also relates to a method for protection of seed and germinating plants from attack by phytopathogenic fungi, by treating the seed with an inventive composition. The invention likewise relates to the use of the inventive compositions for treatment of seed to protect the seed and the germinating plant from phytopathogenic fungi. The invention further relates to seed which has been treated with an inventive composition for protection from phytopathogenic fungi.

The control of phytopathogenic fungi which damage plants post-emergence is effected primarily by treating the soil and the above-ground parts of plants with crop protection compositions. Owing to the concerns regarding a possible influence of the crop protection compositions on the environment and the health of humans and animals, there are efforts to reduce the amount of active ingredients deployed.

One of the advantages of the present invention is that the particular systemic properties of the inventive active ingredients and compositions mean that treatment of the seed with these active ingredients and compositions not only protects the seed itself, but also the resulting plants after emergence, from phytopathogenic fungi. In this way, the immediate treatment of the crop at the time of sowing or shortly thereafter can be dispensed with.

It is likewise considered to be advantageous that the inventive active ingredients or compositions can especially also be used with transgenic seed, in which case the plant growing from this seed is capable of expressing a protein which acts against pests. By virtue of the treatment of such seed with the inventive active ingredients or compositions, merely the expression of the protein, for example an insecticidal protein, can control certain pests. Surprisingly, a further synergistic effect can be observed in this case, which additionally increases the effectiveness for protection against attack by pests.

The inventive compositions are suitable for protecting seed of any plant variety which is used in agriculture, in greenhouses, in forests or in horticulture and viticulture. In particular, this is the seed of cereals (such as wheat, barley, rye, triticale, sorghum/millet and oats), maize, cotton, soya beans, rice, potatoes, sunflower, bean, coffee, beet (for example sugar beet and fodder beet), peanut, oilseed rape, poppy, olive, coconut, cocoa, sugar cane, tobacco, vegetables (such as tomato, cucumbers, onions and lettuce), turf and ornamentals (see also below). The treatment of the seed of cereals (such as wheat, barley, rye, triticale and oats), maize and rice is of particular significance.

As also described below, the treatment of transgenic seed with the inventive active ingredients or compositions is of particular significance. This relates to the seed of plants containing at least one heterologous gene. Definition and examples of suitable heterologous genes are given below.

In the context of the present invention, the inventive composition is applied to the seed alone or in a suitable formulation. Preferably, the seed is treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again.

When treating the seed, care must generally be taken that the amount of the inventive composition applied to the seed and/or the amount of further additives is selected such that the germination of the seed is not impaired, or that the resulting plant is not damaged. This has to be borne in mind in particular in the case of active ingredients which can have phytotoxic effects at certain application rates.

The inventive compositions can be applied directly, i.e. without containing any other components and without having been diluted. In general, it is preferable to apply the compositions to the seed in the form of a suitable formulation. Suitable formulations and methods for seed treatment are known to those skilled in the art and are described, for example, in the following documents: U.S. Pat. No. 4,272,417, U.S. Pat. No. 4,245,432, U.S. Pat. No. 4,808,430, U.S. Pat. No. 5,876,739, US 2003/0176428 A1, WO 2002/080675, WO 2002/028186.

The active ingredients usable in accordance with the invention can be converted to the customary seed dressing formulations, such as solutions, emulsions, suspensions, powders, foams, slurries or other coating compositions for seed, and also ULV formulations.

These formulations are prepared in a known manner, by mixing the active ingredients with customary additives, for example customary extenders and also solvents or diluents, dyes, wetting agents, dispersants, emulsifiers, antifoams, preservatives, secondary thickeners, adhesives, gibberellins and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of active agrochemical ingredients. Preference is given to using alkyl naphthalenesulphonates, such as diisopropyl or diisobutyl naphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Usable with preference are nonionic or anionic dispersants or mixtures of nonionic or anionic dispersants. Suitable nonionic dispersants include especially ethylene oxide/propylene oxide block polymers, alkylphenol polyglycol ethers and tristryrylphenol polyglycol ether, and the phosphated or sulphated derivatives thereof. Suitable anionic dispersants are especially lignosulphonates, polyacrylic acid salts and aryl-sulphonate/formaldehyde condensates.

Antifoams which may be present in the seed dressing formulations usable in accordance with the invention are all foam-inhibiting substances conventionally used for the formulation of active agrochemical ingredients. Silicone antifoams and magnesium stearate can be used with preference.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances usable for such purposes in agrochemical compositions. Preferred examples include cellulose derivatives, acrylic acid derivatives, xanthan, modified clays and finely divided silica.

Adhesives which may be present in the seed dressing formulations usable in accordance with the invention are all customary binders usable in seed dressing products. Preferred examples include polyvinylpyrrolidone, polyvinyl acetate, polyvinyl alcohol and tylose.

The gibberellins which may be present in the seed dressing formulations usable in accordance with the invention may preferably be gibberellins A1, A3 (=gibberellic acid), A4 and A7; particular preference is given to using gibberellic acid. The gibberellins are known (cf. R. Wegler "Chemie der Pflanzenschutz- and Schädlings-bekämpfungsmittel" [Chemistry of the Crop Protection Compositions and Pesticides], vol. 2, Springer Verlag, 1970, p. 401-412).

The seed dressing formulations usable in accordance with the invention can be used, either directly or after previously having been diluted with water, for the treatment of a wide range of different seed, including the seed of transgenic plants. In this case, additional synergistic effects may also occur in interaction with the substances formed by expression.

For treatment of seed with the seed dressing formulations usable in accordance with the invention, or the preparations prepared therefrom by adding water, all mixing units usable customarily for the seed dressing are useful. Specifically, the procedure in the seed dressing is to place the seed into a mixer, to add the particular desired amount of seed dressing formulations, either as such or after prior dilution with water, and to mix everything until the formulation is distributed homogeneously on the seed. If appropriate, this is followed by a drying process.

Mycotoxins

In addition, the inventive treatment can reduce the mycotoxin content in the harvested material and the foods and feeds prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *F. acuminatum, F. asiaticum, F. avenaceum, F. crookwellense, F. culmorum, F. graminearum (Gibberella zeae), F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. sub glutinans, F. tricinctum, F. verticillioides* etc., and also by *Aspergillus* spec., such as *A. flavus, A. parasiticus, A. nomius, A. ochraceus, A. clavatus, A. terreus, A. versicolor, Penicillium* spec., such as *P. verrucosum, P. viridicatum, P. citrinum, P. expansum, P. claviforme, P. roqueforti, Claviceps* spec., such as *C. purpurea, C. fusiformis, C. paspali, C. africana, Stachybotrys* spec. and others.

Material Protection

The inventive active ingredients or compositions can also be used in the protection of materials, for protection of industrial materials against attack and destruction by unwanted microorganisms, for example fungi and insects.

In addition, the inventive compounds can be used as antifouling compositions, alone or in combinations with other active ingredients.

Industrial materials in the present context are understood to mean inanimate materials which have been prepared for use in industry. For example, industrial materials which are to be protected by inventive active ingredients from microbial alteration or destruction may be adhesives, glues, paper, wallpaper and board/cardboard, textiles, carpets, leather, wood, fibers and tissues, paints and plastic articles, cooling lubricants and other materials which can be infected with or destroyed by microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials within the scope of the present invention preferably include adhesives, sizes, paper and card, leather, wood, paints, cooling lubricants and heat transfer fluids, more preferably wood.

The inventive active ingredients or compositions may prevent adverse effects, such as rotting, decay, discoloration, decoloration or formation of mould.

In the case of treatment of wood the compounds/compositions according to the invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention or a composition according to the invention; this includes for example direct application, spraying, dipping, injection or any other suitable means.

In addition, the inventive compounds can be used to protect objects which come into contact with saltwater or brackish water, especially hulls, screens, nets, buildings, moorings and signalling systems, from fouling.

The inventive method for controlling unwanted fungi can also be employed for protecting storage goods. Storage goods are understood to mean natural substances of vegetable or animal origin or processed products thereof which are of natural origin, and for which long-term protection is desired. Storage goods of vegetable origin, for example plants or plant parts, such as stems, leaves, tubers, seeds, fruits, grains, can be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The inventive active ingredients may prevent adverse effects, such as rotting, decay, discoloration, decoloration or formation of mould.

Microorganisms capable of degrading or altering the industrial materials include, for example, bacteria, fungi, yeasts, *algae* and slime organisms. The inventive active ingredients preferably act against fungi, especially moulds, wood-discoloring and wood-destroying fungi (*Ascomycetes, Basidiomycetes, Deuteromycetes* and *Zygomycetes*), and against slime organisms and *algae*. Examples include microorganisms of the following genera: *Alternaria*, such as *Alternaria tenuis; Aspergillus*, such as *Aspergillus niger; Chaetomium*, such as *Chaetomium globosum; Coniophora*, such as *Coniophora puetana; Lentinus*, such as *Lentinus tigrinus; Penicillium*, such as *Penicillium glaucum; Polyporus*, such as *Polyporus versicolor; Aureobasidium*, such as *Aureobasidium pullulans; Sclerophoma*, such as *Sclerophoma pityophila; Trichoderma*, such as *Trichoderma viride; Ophiostoma* spp., *Ceratocystis* spp., *Humicola* spp., *Petriella* spp., *Trichurus* spp., *Coriolus* spp., *Gloeophyllum* spp., *Pleurotus* spp., *Poria* spp., *Serpula* spp. and *Tyromyces* spp., *Cladosporium* spp., *Paecilomyces* spp. *Mucor* spp., *Escherichia*, such as *Escherichia coli; Pseudomonas*, such as *Pseudomonas aeruginosa; Staphylococcus*, such as *Staphylococcus aureus, Candida* spp. and *Saccharomyces* spp., such as *Saccharomyces cerevisae*.

Antimycotic Activity

In addition, the inventive active ingredients also have very good antimycotic activity. They have a very broad antimycotic activity spectrum, especially against dermatophytes and yeasts, moulds and diphasic fungi (for example against *Candida* species, such as *C. albicans, C. glabrata*), and *Epidermophyton floccosum, Aspergillus* species, such as *A. niger* and *A. fumigatus, Trichophyton* species, such as *T. mentagrophytes, Microsporon* species such as *M. canis* and *M. audoui-*

*nii.* The list of these fungi by no means constitutes a restriction of the mycotic spectrum covered, and is merely of illustrative character.

The inventive active ingredients can therefore be used both in medical and in non-medical applications.

GMO

As already mentioned above, it is possible to treat all plants and their parts in accordance with the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts" or "parts of plants" or "plant parts" have been explained above. More preferably, plants of the plant cultivars which are commercially available or are in use are treated in accordance with the invention. Plant cultivars are understood to mean plants which have new properties ("traits") and have been obtained by conventional breeding, by mutagenesis or by recombinant DNA techniques. They can be cultivars, varieties, bio- or genotypes.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or poly-peptide of interest or by downregulating or silencing other gene(s) which are present in the plant (using for example, antisense technology, cosuppression technology, RNA interference—RNAi—technology or microRNA—miRNA—technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted microorganisms. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted microorganisms, the treated plants display a substantial degree of resistance to these microorganisms. In the present case, unwanted microorganisms are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Examples of nematode or insect resistant plants are described in e.g. U.S. patent application Ser. Nos. 11/765,491, 11/765,494, 10/926,819, 10/782,020, 12/032,479, 10/783,417, 10/782,096, 11/657,964, 12/192,904, 11/396,808, 12/166,253, 12/166,239, 12/166,124, 12/166,209, 11/762,886, 12/364,335, 11/763,947, 12/252,453, 12/209,354, 12/491,396, 12/497,221, 12/644,632, 12/646,004, 12/701,058, 12/718,059, 12/721,595, 12/638,591.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses). Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species (WO 92/05251, WO 95/09910, WO 98/27806, WO 05/002324, WO 06/021972 and U.S. Pat. No. 6,229,072). However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as bat-star (e.g. WO 91/02069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-resistant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enol-pyruvylshikimate-3-phosphate synthase (EPSPS). Examples of such EPSPS genes are the AroA gene (mutant CT7) of the bacterium *Salmonella typhimurium* (*Science* 1983, 221, 370-371), the CP4 gene of the bacterium *Agrobacterium* sp. (*Curr. Topics Plant Physiol.* 1992, 7, 139-145), the genes encoding a *Petunia* EPSPS (*Science* 1986, 233, 478-481), a Tomato EPSPS (*J. Biol. Chem.* 1988, 263, 4280-4289), or an *Eleusine* EPSPS (WO 01/66704). It can also be a mutated EPSPS as described in for example EP 0837944, WO 00/66746, WO 00/66747 or WO 02/26995. Glyphosate-tolerant plants can also be obtained by expressing a gene that encodes a glyphosate oxido-reductase enzyme as described in U.S. Pat. No. 5,776,760 and U.S. Pat. No. 5,463,175. Glyphosate-tolerant plants can also be obtained by expressing a gene that encodes a glyphosate acetyl transferase enzyme as described in for example WO 02/036782, WO 03/092360, WO 2005/012515 and WO 2007/024782. Glyphosate-tolerant plants can also be obtained by selecting plants containing naturally-occurring mutations of the above-mentioned genes, as described in for example WO 01/024615 or WO 03/013226. Plants expressing EPSPS genes that confer glyphosate tolerance are described in e.g. U.S. patent application Ser. Nos. 11/517,991, 10/739,610, 12/139,408, 12/352,532, 11/312,866, 11/315,678, 12/421, 292, 11/400,598, 11/651,752, 11/681,285, 11/605,824, 12/468,205, 11/760,570, 11/762,526, 11/769,327, 11/769, 255, 11/943801 or Ser. No. 12/362,774. Plants comprising other genes that confer glyphosate tolerance, such as decarboxylase genes, are described in e.g. U.S. patent application Ser. Nos. 11/588,811, 11/185,342, 12/364,724, 11/185,560 or Ser. No. 12/423,926.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition, e.g. described in U.S. patent application Ser. No. 11/760,602. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. Nos. 5,561,236; 5,648,477; 5,646,024; 5,273, 894; 5,637,489; 5,276,268; 5,739,082; 5,908,810 and 7,112, 665.

Further herbicide-tolerant plants are also plants that are made tolerant to the herbicides inhibiting the enzyme hydroxyphenylpyruvatedioxygenase (HPPD). HPPD is an enzyme that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme as described in WO 96/38567, WO 99/24585, WO 99/24586, WO 09/144079, WO 02/046387, or U.S. Pat. No. 6,768,044. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate deshydrogenase (PDH) activity in addition to a gene encoding an HPPD-tolerant enzyme, as described in WO 04/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide resistant plants are plants that are made tolerant to acetolactate synthase (ALS) inhibitors. Known ALS-inhibitors include, for example, sulfonylurea, imidazolinone, triazolopyrimidines, pryimidinyoxy-(thio) benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright (*Weed Science* 2002, 50, 700-712), but also, in U.S. Pat. Nos. 5,605,011, 5,378,824, 5,141,870, and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and WO 96/33270. Other imidazolinone-tolerant plants are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerant plants are also described in for example WO 2007/024782 and U.S. Patent Application 61/288,958.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084, 082, for rice in WO 97/41218, for sugar beet in U.S. Pat. No. 5,773,702 and WO 99/057965, for lettuce in U.S. Pat. No. 5,198,599, or for sunflower in WO 01/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al. (1998, Microbiology and Molecular Biology Reviews, 62: 807-813), updated by Crickmore et al. (2005) at the *Bacillus thuringiensis* toxin nomenclature, online at: http://www.lifesci.sussex.ac.uk/Home/Neil_Crickmore/BY), or insecticidal portions thereof, e.g., proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP-A 1 999 141 and WO 2007/107302), or such proteins en-coded by synthetic genes as e.g. described in and U.S. patent application Ser. No. 12/249,016; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Nat. Biotechnol. 2001, 19, 668-72; *Applied Environm. Microbiol.* 2006, 71, 1765-1774) or the binary toxin made up of the Cry1A or Cry1F proteins and the Cry2Aa or Cry2Ab or Cry2Ae proteins (U.S. patent application Ser. No. 12/214,022 and EP-A 2 300 618); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON89034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or 9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. patent application Ser. No. 61/126,083 and Ser. No. 61/195,019), or the binary toxin made up of the VIP3 protein and the Cry2Aa or Cry2Ab or Cry2Ae proteins (U.S. patent application Ser. No. 12/214,022 and EP-A 2 300 618).

10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein)

Of course, an insect-resistant transgenic plant, as used herein, also includes any plant comprising a combination of genes encoding the proteins of any one of the above classes 1 to 10. In one embodiment, an insect-resistant plant contains more than one transgene encoding a protein of any one of the above classes 1 to 10, to expand the range of target insect species affected when using different proteins directed at different target insect species, or to delay insect resistance development to the plants by using different proteins insecticidal to the same target insect species but having a different mode of action, such as binding to different receptor binding sites in the insect.

An "insect-resistant transgenic plant", as used herein, further includes any plant containing at least one transgene comprising a sequence producing upon expression a double-stranded RNA which upon ingestion by a plant insect pest inhibits the growth of this insect pest, as described e.g. in WO 2007/080126, WO 2006/129204, WO 2007/074405, WO 2007/080127 and WO 2007/035650.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

1) plants which contain a transgene capable of reducing the expression and/or the activity of poly(ADP-ribose) polymerase (PARP) gene in the plant cells or plants as described in WO 00/04173, WO 2006/045633, EP-A 1 807 519, or EP-A 2 018 431.

2) plants which contain a stress tolerance enhancing transgene capable of reducing the expression and/or the activity of the PARG encoding genes of the plants or plants cells, as described e.g. in WO 2004/090140.

3) plants which contain a stress tolerance enhancing transgene coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase as described e.g. in EP-A 1 794 306, WO 2006/133827, WO 2007/107326, EP-A 1 999 263, or WO 2007/107326.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications. Said transgenic plants synthesizing a modified starch are disclosed, for example, in EP-A 0 571 427, WO 95/04826, EP-A 0 719 338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO 99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 04/056999, WO 05/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, WO 2008/017518, WO 2008/080630, WO 2008/080631, WO 2008/090008, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. No. 5,824,790, U.S. Pat. No. 6,013,861, WO 94/04693, WO 94/09144, WO 94/11520, WO 95/35026, WO 97/20936, WO 2010/012796, WO 2010/003701, 2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, as disclosed in EP-A 0 663 956, WO 96/01904, WO 96/21023, WO 98/39460, and WO 99/24593, plants producing alpha-1,4-glucans as disclosed in WO 95/31553, US 2002031826, U.S. Pat. No. 6,284, 479, U.S. Pat. No. 5,712,107, WO 97/47806, WO 97/47807, WO 97/47808 and WO 00/14249, plants producing alpha-1,6 branched alpha-1,4-glucans, as disclosed in WO 00/73422, plants producing alternan, as disclosed in e.g. WO 00/47727, WO 00/73422, U.S. Pat. No. 5,908,975 and EP-A 0 728 213, 3) transgenic plants which produce hyaluronan, as for example disclosed in WO 2006/032538, WO 2007/039314, WO 2007/039315, WO 2007/039316, JP-A 2006-304779, and WO 2005/012529.

4) transgenic plants or hybrid plants, such as onions with characteristics such as 'high soluble solids content', 'low pungency' (LP) and/or 'long storage' (LS), as described in U.S. patent application Ser. No. 12/020,360.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:

a) Plants, such as cotton plants, containing an altered form of cellulose synthase genes as described in WO 98/00549.
b) Plants, such as cotton plants, containing an altered form of rsw2 or rsw3 homologous nucleic acids as described in WO 2004/053219.
c) Plants, such as cotton plants, with increased expression of sucrose phosphate synthase as described in WO 01/17333.
d) Plants, such as cotton plants, with increased expression of sucrose synthase as described in WO 02/45485.
e) Plants, such as cotton plants, wherein the timing of the plasmodesmatal gating at the basis of the fiber cell is altered, e.g. through downregulation of fiber-selective β-1, 3-glucanase as described in WO 2005/017157, or as described in WO 2009/143995.
f) Plants, such as cotton plants, having fibers with altered reactivity, e.g. through the expression of N-acetylglucosaminetransferase gene including nodC and chitin synthase genes as described in WO 2006/136351.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics and include:

a) Plants, such as oilseed rape plants, producing oil having a high oleic acid content as described e.g. in U.S. Pat. No. 5,969,169, U.S. Pat. No. 5,840,946 or U.S. Pat. No. 6,323, 392 or U.S. Pat. No. 6,063,947
b) Plants such as oilseed rape plants, producing oil having a low linolenic acid content as described in U.S. Pat. No. 6,270,828, U.S. Pat. No. 6,169,190, or U.S. Pat. No. 5,965, 755
c) Plant such as oilseed rape plants, producing oil having a low level of saturated fatty acids as described e.g. in U.S. Pat. No. 5,434,283 or U.S. patent application Ser. No. 12/668,303

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering as described in U.S. Patent Application 61/135,230, WO 2009/068313 and WO 2010/006732.

Plants or plant cultivars (that can be obtained by plant biotechnology methods such as genetic engineering) which may also be treated according to the invention are plants, such as Tobacco plants, with altered post-translational protein modification patterns, for example as described in WO 2010/121818 and WO 2010/145846.

Particularly useful transgenic plants which may be treated according to the invention are plants containing transformation events, or combination of transformation events, that are the subject of petitions for non-regulated status, in the United States of America, to the Animal and Plant Health Inspection Service (APHIS) of the United States Department of Agriculture (USDA) whether such petitions are granted or are still pending. At any time this information is readily available from APHIS (4700 River Road, Riverdale, Md. 20737, USA), for instance on its internet site (URL http://www.aphis.usda.gov/brs/not_reg.html). On the filing date of this application the petitions for nonregulated status that were pending with APHIS or granted by APHIS were those which contains the following information:

Petition: the identification number of the petition. Technical descriptions of the transformation events can be found in the individual petition documents which are obtainable from APHIS, for example on the APHIS website, by reference to this petition number. These descriptions are herein incorporated by reference.

Extension of Petition: reference to a previous petition for which an extension is requested.

Institution: the name of the entity submitting the petition.

Regulated article: the plant species concerned.

Transgenic phenotype: the trait conferred to the plants by the transformation event.

Transformation event or line: the name of the event or events (sometimes also designated as lines or lines) for which nonregulated status is requested.

APHIS documents: various documents published by APHIS in relation to the Petition and which can be requested with APHIS.

Additional particularly useful plants containing single transformation events or combinations of transformation events are listed for example in the databases from various national or regional regulatory agencies (see for example http://gmoinfo.jrc.it/gmp_browse.aspx and http://www.agbios.com/dbase.php).

Particularly useful transgenic plants which may be treated according to the invention are plants containing transformation events, or a combination of transformation events, and that are listed for example in the databases for various national or regional regulatory agencies including Event 1143-14A (cotton, insect control, not deposited, described in WO 2006/128569); Event 1143-51B (cotton, insect control, not deposited, described in WO 2006/128570); Event 1445 (cotton, herbicide tolerance, not deposited, described in US-A 2002-120964 or WO 02/034946); Event 17053 (rice, herbicide tolerance, deposited as PTA-9843, described in WO 2010/117737); Event 17314 (rice, herbicide tolerance, deposited as PTA-9844, described in WO 2010/117735); Event 281-24-236 (cotton, insect control-herbicide tolerance, deposited as PTA-6233, described in WO 2005/103266 or US-A 2005-216969); Event 3006-210-23 (cotton, insect control-herbicide tolerance, deposited as PTA-6233, described in US-A 2007-143876 or WO 2005/103266); Event 3272 (corn, quality trait, deposited as PTA-9972, described in WO 2006/098952 or US-A 2006-230473); Event 40416 (corn, insect control-herbicide tolerance, deposited as ATCC PTA-11508, described in WO 2011/075593); Event 43A47 (corn, insect control-herbicide tolerance, deposited as ATCC PTA-11509, described in WO 2011/075595); Event 5307 (corn, insect control, deposited as ATCC PTA-9561, described in WO 2010/077816); Event ASR-368 (bent grass, herbicide tolerance, deposited as ATCC PTA-4816, described in US-A 2006-162007 or WO 2004/053062); Event B16 (corn, herbicide tolerance, not deposited, described in US-A 2003-126634); Event BPS-CV127-9 (soybean, herbicide tolerance, deposited as NCIMB No. 41603, described in WO 2010/080829); Event CE43-67B (cotton, insect control, deposited as DSM ACC2724, described in US-A 2009-217423 or WO2006/128573); Event CE44-69D (cotton, insect control, not deposited, described in US-A 2010-0024077); Event CE44-69D (cotton, insect control, not deposited, described in WO 2006/128571); Event CE46-02A (cotton, insect control, not deposited, described in WO 2006/128572); Event COT102 (cotton, insect control, not deposited, described in US-A 2006-130175 or WO 2004/039986); Event COT202 (cotton, insect control, not deposited, described in US-A 2007-067868 or WO 2005/054479); Event COT203 (cotton, insect control, not deposited, described in WO 2005/054480); Event DAS40278 (corn, herbicide tolerance, deposited as ATCC PTA-10244, described in WO 2011/022469); Event DAS-59122-7 (corn, insect control-herbicide tolerance, deposited as ATCC PTA-11384, described in US-A 2006-070139); Event DAS-59132 (corn, insect control-herbicide tolerance, not deposited, described in WO 2009/100188); Event DAS68416 (soybean, herbicide tolerance, deposited as ATCC PTA-10442, described in WO 2011/066384 or WO 2011/066360); Event DP-098140-6 (corn, herbicide tolerance, deposited as ATCC PTA-8296, described in US-A 2009-137395 or WO 2008/112019); Event DP-305423-1 (soybean, quality trait, not deposited, described in US-A 2008-312082 or WO 2008/054747); Event DP-32138-1 (corn, hybridization system, deposited as ATCC PTA-9158, described in US-A 2009-0210970 or WO 2009/103049); Event DP-356043-5 (soybean, herbicide tolerance, deposited as ATCC PTA-8287, described in US-A 2010-0184079 or WO 2008/002872); Event EE-1 (brinjal, insect control, not deposited, described in WO 2007/091277); Event FI117 (corn, herbicide tolerance, deposited as ATCC 209031, described in US-A 2006-059581 or WO 98/044140); Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO 98/044140); Event GHB119 (cotton, insect control-herbicide tolerance, deposited as ATCC PTA-8398, described in WO 2008/151780); Event GHB614 (cotton, herbicide tolerance, deposited as ATCC PTA-6878, described in US-A 2010-050282 or WO 2007/017186); Event GJ11 (corn, herbicide tolerance, deposited as ATCC 209030, described in US-A 2005-188434 or WO 98/044140); Event GM RZ13 (sugar beet, virus resistance, deposited as NCIMB-41601, described in WO 2010/076212); Event H7-1 (sugar beet, herbicide tolerance, deposited as NCIMB 41158 or NCIMB 41159, described in US-A 2004-172669 or WO 2004/074492); Event JOPLIN1 (wheat, disease tolerance, not deposited, described in US-A 2008-064032); Event LL27 (soybean, herbicide tolerance, deposited as NCIMB41658, described in WO 2006/108674 or US-A 2008-320616); Event LL55 (soybean, herbicide tolerance, deposited as NCIMB 41660, described in WO 2006/108675 or US-A 2008-196127); Event LLcotton25 (cotton, herbicide tolerance, deposited as ATCC PTA-3343, described in WO 03/013224 or US-A 2003-097687); Event LLRICE06 (rice, herbicide tolerance, deposited as ATCC-23352, described in U.S. Pat. No. 6,468,747 or WO 00/026345); Event LLRICE601 (rice, herbicide tolerance, deposited as ATCC PTA-2600, described in US-A 2008-2289060 or WO 00/026356); Event LY038 (corn, quality trait, deposited as ATCC PTA-5623, described in US-A 2007-028322 or WO 2005/061720); Event MIR162 (corn, insect control, deposited as PTA-8166, described in US-A 2009-300784 or WO 2007/142840); Event MIR604 (corn, insect control, not deposited, described in US-A 2008-167456 or WO 2005/103301); Event MON15985 (cotton, insect control, deposited as ATCC PTA-2516, described in US-A 2004-250317 or WO 02/100163); Event MON810 (corn, insect control, not deposited, described in US-A 2002-102582); Event MON863 (corn, insect control, deposited as ATCC PTA-2605, described in WO 2004/011601 or US-A 2006-095986); Event MON87427 (corn, pollination control, deposited as ATCC PTA-7899, described in WO 2011/062904); Event MON87460 (corn, stress tolerance, deposited as ATCC PTA-8910, described in WO 2009/111263 or US-A 2011-

0138504); Event MON87701 (soybean, insect control, deposited as ATCC PTA-8194, described in US-A 2009-130071 or WO 2009/064652); Event MON87705 (soybean, quality trait-herbicide tolerance, deposited as ATCC PTA-9241, described in US-A 2010-0080887 or WO 2010/037016); Event MON87708 (soybean, herbicide tolerance, deposited as ATCC PTA9670, described in WO 2011/034704); Event MON87754 (soybean, quality trait, deposited as ATCC PTA-9385, described in WO 2010/024976); Event MON87769 (soybean, quality trait, deposited as ATCC PTA-8911, described in US-A 2011-0067141 or WO 2009/102873); Event MON88017 (corn, insect control-herbicide tolerance, deposited as ATCC PTA-5582, described in US-A 2008-028482 or WO 2005/059103); Event MON88913 (cotton, herbicide tolerance, deposited as ATCC PTA-4854, described in WO 2004/072235 or US-A 2006-059590); Event MON89034 (corn, insect control, deposited as ATCC PTA-7455, described in WO 2007/140256 or US-A 2008-260932); Event MON89788 (soybean, herbicide tolerance, deposited as ATCC PTA-6708, described in US-A 2006-282915 or WO 2006/130436); Event MS11 (oilseed rape, pollination control-herbicide tolerance, deposited as ATCC PTA-850 or PTA-2485, described in WO 01/031042); Event MS8 (oilseed rape, pollination control-herbicide tolerance, deposited as ATCC PTA-730, described in WO 01/041558 or US-A 2003-188347); Event NK603 (corn, herbicide tolerance, deposited as ATCC PTA-2478, described in US-A 2007-292854); Event PE-7 (rice, insect control, not deposited, described in WO 2008/114282); Event RF3 (oilseed rape, pollination control-herbicide tolerance, deposited as ATCC PTA-730, described in WO 01/041558 or US-A 2003-188347); Event RT73 (oilseed rape, herbicide tolerance, not deposited, described in WO 02/036831 or US-A 2008-070260); Event T227-1 (sugar beet, herbicide tolerance, not deposited, described in WO 02/44407 or US-A 2009-265817); Event T25 (corn, herbicide tolerance, not deposited, described in US-A 2001-029014 or WO 01/051654); Event T304-40 (cotton, insect control-herbicide tolerance, deposited as ATCC PTA-8171, described in US-A 2010-077501 or WO 2008/122406); Event T342-142 (cotton, insect control, not deposited, described in WO 2006/128568); Event TC1507 (corn, insect control-herbicide tolerance, not deposited, described in US-A 2005-039226 or WO 2004/099447); Event VIP1034 (corn, insect control-herbicide tolerance, deposited as ATCC PTA-3925, described in WO 03/052073), Event 32316 (corn, insect control-herbicide tolerance, deposited as PTA-11507, described in WO 2011/084632), Event 4114 (corn, insect control-herbicide tolerance, deposited as PTA-11506, described in WO 2011/084621).

Application Rates and Timing

When using the inventive active ingredients as fungicides, the application rates can be varied within a relatively wide range, depending on the kind of application. The application rate of the inventive active ingredients is
  in the case of treatment of plant parts, for example leaves: from 0.1 to 10 000 g/ha, preferably from 10 to 1000 g/ha, more preferably from 10 to 800 g/ha, even more preferably from 50 to 300 g/ha (in the case of application by watering or dripping, it is even possible to reduce the application rate, especially when inert substrates such as rockwool or perlite are used);
  in the case of seed treatment: from 2 to 200 g per 100 kg of seed, preferably from 3 to 150 g per 100 kg of seed, more preferably from 2.5 to 25 g per 100 kg of seed, even more preferably from 2.5 to 12.5 g per 100 kg of seed;
  in the case of soil treatment: from 0.1 to 10 000 g/ha, preferably from 1 to 5000 g/ha.

These application rates are merely by way of example and are not limiting for the purposes of the invention.

The inventive active ingredients or compositions can thus be used to protect plants from attack by the pathogens mentioned for a certain period of time after treatment. The period for which protection is provided extends generally for 1 to 28 days, preferably for 1 to 14 days, more preferably for 1 to 10 days, most preferably for 1 to 7 days, after the treatment of the plants with the active ingredients, or for up to 200 days after a seed treatment.

The method of treatment according to the invention also provides the use or application of compounds (A) and (B) and/or (C) in a simultaneous, separate or sequential manner. If the single active ingredients are applied in a sequential manner, i.e. at different times, they are applied one after the other within a reasonably short period, such as a few hours or days. Preferably the order of applying the compounds (A) and (B) and/or (C) is not essential for working the present invention.

The plants listed can particularly advantageously be treated in accordance with the invention with the compounds of the general formula (I) and the inventive compositions. The preferred ranges stated above for the active ingredients or compositions also apply to the treatment of these plants. Particular emphasis is given to the treatment of plants with the compounds or compositions specifically mentioned in the present text.

The invention is illustrated by the examples below. However, the invention is not limited to the examples.

PREPARATION EXAMPLES

In analogy to the examples above and according to the general description of the processes of preparing the compounds according to the invention the compounds in the following Table 1 may be obtained.

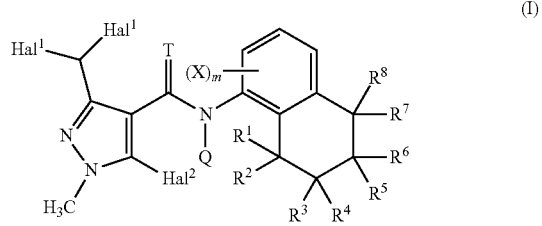
(I)

TABLE 1

| Ex. | Hal¹ | Hal² | T | Q | X | m | R¹ | R² | R³ | R⁴ | R⁵ | R⁶ | R⁷ | R⁸ | logP |
|---|---|---|---|---|---|---|---|---|---|---|---|---|---|---|---|
| 1 | F | F | O | H | — | 0 | H | H | H | H | H | H | Me | Me | 3.67[a] |
| 2 | F | Cl | O | H | — | 0 | H | H | H | H | H | H | Me | Me | 3.89[a] |

TABLE 1-continued

| Ex. | Hal$^1$ | Hal$^2$ | T | Q | X | m | R$^1$ | R$^2$ | R$^3$ | R$^4$ | R$^5$ | R$^6$ | R$^7$ | R$^8$ | logP | |
|---|---|---|---|---|---|---|---|---|---|---|---|---|---|---|---|---|
| 3 | F | F | O | H | — | 0 | Me | H | H | H | H | H | Me | Me | 3.92[a] | |
| 4 | F | Cl | O | H | — | 0 | Me | H | H | H | H | H | Me | Me | 4.14[a] | |
| 5 | F | Cl | O | H | — | 0 | H | H | H | H | Me | Me | =CH$_2$ | | 4.14[a] | |
| 6 | F | F | O | H | — | 0 | H | H | H | H | Me | Me | =CH$_2$ | | 3.87[a] | |
| 7 | F | Cl | O | H | — | 0 | H | H | H | H | Me | H | Me | H | 4.09[a] | R$_5$ and R$_7$ are cis configurated |
| 8 | F | F | O | H | — | 0 | H | H | H | H | Me | H | Me | H | 3.83[a] | R$_5$ and R$_7$ are cis configurated |
| 9 | F | F | O | H | — | 0 | Me | H | Me | H | H | H | H | H | 3.68[a] | R$_1$ and R$_3$ are cis configurated |
| 10 | F | Cl | O | H | — | 0 | Me | H | Me | H | H | H | H | H | 3.92[a] | R$_1$ and R$_3$ are cis configurated |
| 11 | F | Cl | O | H | — | 0 | H | H | H | H | Me | Me | Me | H | 4.39[a] | |
| 12 | F | F | O | H | — | 0 | H | H | H | H | Me | Me | Me | H | 4.11[a] | |
| 13 | F | F | O | H | — | 0 | H | H | Me | Me | H | H | H | H | 3.72[a] | |
| 14 | F | Cl | O | H | — | 0 | H | H | Me | Me | H | H | H | H | 3.9[a] | |
| 15 | F | Cl | O | H | — | 0 | H | H | H | H | Me | H | Me | Me | 4.29[a] | |
| 16 | F | Cl | O | H | 4-F | 1 | H | H | H | H | H | H | Me | Me | 4.01[a] | |
| 17 | F | Cl | S | H | 4-F | 1 | H | H | H | H | H | H | Me | Me | 4.24[a] | |
| 18 | F | F | O | H | — | 0 | H | H | H | H | H | H | =N—OEt | | 3.31[a] | |
| 19 | F | F | O | H | — | 0 | H | H | H | H | H | H | =N—OMe | | 2.86[a] | |
| 20 | F | Br | O | H | — | 0 | H | H | H | H | H | H | =N—OEt | | 3.57[a] | |
| 21 | F | Cl | O | H | — | 0 | H | H | H | H | H | H | =N—OEt | | 3.55[a] | |
| 22 | F | F | O | H | — | 0 | H | H | H | H | Me | Me | H | H | 3.79[a] | |
| 23 | F | Br | O | H | — | 0 | H | H | H | H | Me | Me | H | H | 4.04[a] | |
| 24 | F | F | O | H | 4-F | 1 | H | H | H | H | H | H | Me | Me | 3.76[a] | |
| 25 | F | Cl | O | H | — | 0 | H | H | H | H | Me | Me | H | H | 4.04[a] | |
| 26 | F | Br | O | H | — | 0 | H | H | H | H | H | H | =N—OMe | | 3.13[a] | |
| 27 | F | Cl | O | H | — | 0 | Me | Me | H | H | H | H | H | H | 3.69[a] | |
| 28 | F | Cl | O | H | — | 0 | H | H | H | H | H | H | =N—OMe | | 3.09[a] | |
| 29 | F | F | O | H | — | 0 | Me | Me | H | H | H | H | H | H | 3.44[a] | |
| 30 | F | F | O | H | — | 0 | H | H | H | H | H | H | =N—OMe | | 2.86[a] | |
| 31 | F | Br | S | H | — | 0 | H | H | H | H | Me | Me | H | H | 4.11[a] | |
| 32 | F | F | S | H | — | 0 | H | H | H | H | Me | Me | H | H | 3.99[a] | |
| 33 | F | Cl | S | H | — | 0 | H | H | H | H | Me | Me | H | H | 4.11[a] | |

Me = methyl, Et = ethyl

In analogy to the examples above and according to the general description of the processes of preparing the compounds according to the invention the compounds according to formula (III-a) in the following Table 2 may be obtained.

TABLE 2

| Ex. | Q | X | m | R$^1$ | R$^2$ | R$^3$ | R$^4$ | R$^5$ | R$^6$ | R$^7$ | R$^8$ | logP | |
|---|---|---|---|---|---|---|---|---|---|---|---|---|---|
| III-a-1 | H | — | 0 | H | H | H | H | H | H | Me | Me | 1.69[a] | |
| III-a-2 | H | — | 0 | Me | H | H | H | H | H | Me | Me | 2.56[a] | |
| III-a-3 | H | — | 0 | H | H | H | H | Me | Me | =CH$_2$ | | 2.44[a] | |
| III-a-4 | H | — | 0 | H | H | H | H | Me | H | Me | H | 1.93[a] | R$_5$ and R$_7$ cis configured |
| III-a-5 | H | — | 0 | H | H | H | H | Me | Me | Me | H | 2.11[a] | |
| III-a-6 | H | — | 0 | H | H | Me | Me | H | H | H | H | 1.88[a] | |
| III-a-7 | H | — | 0 | H | H | H | H | Me | H | Me | Me | 2.18[a] | |
| III-a-8 | H | 4-F | 1 | H | H | H | H | H | H | Me | Me | 1.96[a] | |
| III-a-9 | H | — | 0 | H | H | H | H | H | H | =N—OEt | | 1.98[a] | |
| III-a-10 | H | — | 0 | H | H | H | H | H | H | =N—OMe | | 1.47[a] | |
| III-a-11 | H | — | 0 | Me | Me | H | H | H | H | H | H | | |
| III-a-12 | H | — | 0 | H | H | H | H | Me | Me | H | H | 1.86[a] | |

Measurement of log P values was performed according EEC directive 79/831 Annex V.A8 by HPLC (High Performance Liquid Chromatography) on reversed phase columns with the following methods:

[a]Measurement of LC-MS was done at pH 2.7 with 0.1% formic acid in water and with acetonitrile (contains 0.1% formic acid) as eluent with a linear gradient from 10% acetonitrile to 95% acetonitrile.

Calibration was done with not branched alkan2-ones (with 3 to 16 carbon atoms) with known log P-values (measurement of log P values using retention times with linear interpolation between successive alkanones). lambda-maX-values were determined using UV-spectra from 200 nm to 400 nm and the peak values of the chromatographic signals.

NMR Peak Lists

1H-NMR data of selected examples are written in form of 1H-NMR-peak lists. To each signal peak are listed the δ-value in ppm and the signal intensity in round brackets. Between the δ-value—signal intensity pairs are semicolons as delimiters.

The peak list of an example has therefore the form:

δ$_1$ (intensity$_1$); δ$_2$ (intensity$_2$); . . . ; δ$_i$(intensity$_i$); . . . ; δ$_n$(intensity$_n$)

NMR Peak Lists Active Ingredient

Example 1, Solvent: CDCl3, Spectrometer: 300,16 MHz
7.7063 (1.21); 7.6861 (1.34); 7.4999 (1.42); 7.2558 (1.35); 7.2212 (3.52); 7.1937 (1.34); 7.0371 (1.40); 6.8578 (0.70); 3.8467 (8.14); 2.6250 (2.88); 1.8477 (2.14); 1.8394 (2.16); 1.6564 (2.72); 1.6367 (2.81); 1.2936 (16.00); −0.0002 (0.36)

Example 2, Solvent: CDCl3, Spectrometer: 300,16 MHz
7.7791 (1.14); 7.7239 (1.06); 7.7002 (1.13); 7.2963 (0.64); 7.2607 (3.11); 7.2337 (2.78); 7.2039 (1.17); 7.1789 (0.41);7.1160 (1.29); 6.9370 (0.67); 3.9548 (7.95); 2.6702 (1.26); 2.6508 (2.51); 2.6317 (1.42); 2.0456 (0.42); 1.8535 (1.62); 1.8343 (1.48); 1.6656 (2.11); 1.6556 (1.78); 1.6471 (1.80); 1.5723 (1.86); 1.2980 (16.00); 1.2624 (7.48); 0.8820 (3.94); 0.8593 (1.89); −0.0002 (1.41)

Example 3, Solvent: CDCl3, Spectrometer: 300,16 MHz
7.7196 (1.34); 7.7137 (1.36); 7.6954 (1.52); 7.6894 (1.54); 7.6170 (1.10); 7.2721 (1.94); 7.2570 (1.39); 7.2482 (0.66); 7.2418 (1.01); 7.2216 (3.45); 7.2148 (3.31); 7.2112 (3.88); 7.1867 (2.74); 7.1602 (0.95); 7.0926 (4.06); 6.9131 (2.00); 3.8442 (10.51); 3.0319 (0.60); 3.0280 (0.60); 3.0177 (0.64); 3.0106 (0.90); 2.9949 (0.62); 2.9876 (0.65); 2.0338 (0.75); 2.0193 (0.56); 2.0097 (0.62); 2.0017 (0.55); 1.9940 (0.50); 1.9756 (0.66); 1.9706 (0.71); 1.9570 (0.96); 1.9456 (1.34); 1.9063 (1.00); 1.8992 (1.00); 1.8586 (0.81); 1.8521 (0.49); 1.7093 (0.65); 1.6673 (0.44); 1.6596 (0.79); 1.6520 (0.85); 1.6456 (0.80); 1.6247 (0.43); 1.6168 (0.66); 1.6112 (0.84); 1.6048 (0.98); 1.5448 (1.28); 1.5315 (0.68); 1.5052 (0.81); 1.4957 (0.66); 1.4877 (0.56); 1.3560 (16.00); 1.3060 (0.49); 1.2991 (0.50); 1.2900 (0.71); 1.2669 (2.60); 1.2520 (1.36); 1.2326 (8.94); 1.2193 (15.58); 1.2093 (9.49); 0.9025 (0.88); 0.8806 (3.00); 0.8574 (1.06); −0.0002 (0.78)

Example 4, Solvent: CDCl3, Spectrometer: 300,16 MHz
7.8726 (1.10); 7.6929 (1.09); 7.6867 (1.13); 7.6688 (1.25); 7.6626 (1.33); 7.3405 (1.61); 7.2605 (36.02); 7.2512 (0.98); 7.2406 (3.54); 7.2323 (4.84); 7.2075 (2.59); 7.1810 (0.90); 7.1606 (3.45); 6.9807 (1.69); 3.9671 (15.87); 3.0668 (0.59); 3.0577 (0.61); 3.0494 (0.86); 3.0348 (0.57); 3.0268 (0.64); 2.0461 (0.72); 2.0301 (0.54); 2.0209 (0.57); 2.0146 (0.55); 2.0053 (0.51); 1.9866 (0.61); 1.9817 (0.66); 1.9683 (0.87); 1.9550 (1.24); 1.9155 (0.96); 1.9081 (1.03); 1.8609 (0.50); 1.6612 (0.45); 1.6532 (0.74); 1.6458 (0.88); 1.6398 (0.74); 1.6352 (0.73); 1.6183 (0.43); 1.6106 (0.64); 1.6038 (0.80); 1.5989 (0.94); 1.5473 (19.21); 1.5366 (1.04); 1.5102 (0.89); 1.5010 (0.70); 1.4926 (0.59); 1.3631 (16.00); 1.3312 (0.84); 1.3061 (1.71); 1.2671 (10.59); 1.2346 (11.09); 1.2265 (16.00); 1.2112 (9.78); 0.9039 (3.71); 0.8820 (12.52); 0.8588 (4.53); 0.0107 (0.62); −0.0002 (25.50); −0.0111 (1.13)

Example 5, Solvent: DMSO, Spectrometer: 300,16 MHz
9.5050 (1.51); 7.5404 (1.05); 7.5165 (1.24); 7.4040 (0.65); 7.3781 (0.83); 7.3409 (0.94); 7.2331 (0.89); 7.2068 (1.40); 7.1806 (0.66); 7.1617 (2.03); 6.9826 (0.98); 5.4994 (2.89); 5.0846 (3.06); 3.9219 (7.91); 3.8659 (0.34); 3.3241 (24.45); 2.7834 (0.89); 2.7613 (1.97); 2.7391 (1.02); 2.5131 (2.72); 2.5071 (5.92); 2.5011 (8.22); 2.4951 (6.06); 2.4891 (2.96); 1.6431 (1.08); 1.6212 (2.41); 1.5991 (1.07); 1.1006 (16.00); −0.0002 (6.13)

Example 6, Solvent: DMSO, Spectrometer: 300,16 MHz
9.3001 (1.40); 7.5376 (1.05); 7.5141 (1.20); 7.5109 (1.19); 7.4018 (0.87); 7.3772 (1.15); 7.3439 (1.02); 7.2285 (0.97); 7.2023 (1.54); 7.1760 (0.71); 7.1650 (2.34); 6.9861 (1.09); 5.4997 (2.87); 5.0841 (3.05); 3.8302 (5.84); 3.3255 (20.12); 2.7463 (0.86); 2.7242 (1.93); 2.7020 (0.98); 2.5133 (1.66); 2.5072 (3.69); 2.5011 (5.15); 2.4950 (3.80); 2.4890 (1.83); 1.6364 (1.06); 1.6145 (2.40); 1.5922 (1.07); 1.0997 (16.00); 1.0599 (0.49); −0.0002 (4.27)

Example 7, Solvent: DMSO, Spectrometer: 300,16 MHz
9.3525 (2.79); 7.3285 (1.92); 7.3075 (1.21); 7.2805 (1.55); 7.1645 (1.38); 7.1493 (4.23); 7.1389 (3.05); 7.1132 (1.75); 7.0638 (2.73); 7.0410 (1.58); 6.9701 (1.90); 3.9151 (16.00); 3.3897 (0.34); 3.3245 (68.29); 3.2576 (0.34); 2.8560 (0.92); 2.8375 (1.10); 2.8317 (1.12); 2.8158 (1.34); 2.7984 (0.79); 2.7593 (0.83); 2.7482 (0.99); 2.7396 (1.11); 2.7290 (0.89); 2.6659 (0.61); 2.6416 (0.80); 2.6323 (0.87); 2.6081 (0.95); 2.5747 (0.49); 2.5514 (0.42); 2.5129 (4.99); 2.5070 (10.81); 2.5009 (15.05); 2.4948 (11.15); 2.4889 (5.49); 1.8902 (0.78); 1.8755 (0.80); 1.8665 (0.72); 1.8556 (0.64); 1.6767 (0.34); 1.6669 (0.41); 1.6450 (0.79); 1.6340 (1.02); 1.6203 (1.21); 1.5973 (0.89); 1.5832 (0.92); 1.5601 (0.87); 1.5374 (0.54); 1.5255 (0.50); 1.0890 (9.05); 1.0652 (8.97); 0.9748 (8.46); 0.9519 (8.21); 0.0106 (0.34); −0.0002 (11.04); −0.0111 (0.56)

Example 8, Solvent: DMSO, Spectrometer: 300,16 MHz
9.1512 (3.59); 7.3322 (2.67); 7.3040 (2.22); 7.2790 (2.96); 7.1610 (2.33); 7.1533 (6.15); 7.1357 (4.16); 7.1103 (2.48); 7.0646 (3.52); 7.0392 (2.01); 6.9743 (2.82); 5.7579 (0.88); 3.8239 (16.00); 3.3901 (0.58); 3.3233 (90.95); 3.2571 (0.61); 2.8548 (1.23); 2.8389 (1.45); 2.8151 (1.28); 2.7909 (0.52); 2.7603 (0.65); 2.7389 (0.64); 2.7118 (1.09); 2.7010 (1.38); 2.6929 (1.41); 2.6834 (1.06); 2.6363 (0.86); 2.6005 (1.14); 2.5776 (1.36); 2.5536 (0.60); 2.5435 (0.70); 2.5131 (9.50); 2.5071 (20.15); 2.5010 (27.71); 2.4949 (20.28); 2.4889 (9.86); 1.8919 (1.07); 1.8769 (1.07); 1.8664 (0.95); 1.8549 (0.83); 1.6627 (0.54); 1.6385 (1.15); 1.6295 (1.38); 1.6159 (1.84); 1.5946 (1.34); 1.5798 (1.21); 1.5594 (1.12); 1.5364 (0.69); 1.5230 (0.63); 1.0866 (11.89); 1.0628 (11.79); 0.9739 (11.25); 0.9511 (10.87); 0.9099 (0.37); 0.0105 (0.64); −0.0002 (23.22); −0.0111 (1.14)

Example 9, Solvent: DMSO, Spectrometer: 300,16 MHz
9.5012 (0.48); 9.2780 (1.24); 9.2587 (2.74); 8.4423 (0.40); 7.3259 (2.02); 7.3213 (1.59); 7.2752 (0.74); 7.2497 (0.96); 7.2357 (1.57); 7.2101 (2.35); 7.1469 (4.20); 7.1417 (2.42); 7.1335 (2.19); 7.1249 (1.00); 7.1081 (3.93); 7.0995 (1.69); 7.0825 (2.34); 7.0738 (1.22); 6.9910 (2.98); 6.9677 (3.99); 4.1842 (0.36); 3.9680 (2.59); 3.8318 (16.00); 3.3251 (47.20); 3.0290 (1.00); 3.0145 (1.21); 3.0068 (1.10); 2.9915 (1.07); 2.9691 (0.40); 2.8911 (0.38); 2.8614 (0.64); 2.8334 (1.99); 2.8099 (2.61); 2.7784 (1.02); 2.7563 (0.54); 2.7249 (0.96); 2.7048 (0.88); 2.5128 (6.61); 2.5070 (13.58); 2.5011 (18.32); 2.4951 (13.34); 2.4894 (6.52); 1.9233 (0.34); 1.8148 (1.20); 1.7772 (0.62); 1.6202 (0.58); 1.5888 (1.64); 1.5631 (2.04); 1.5342 (1.13); 1.4643 (0.38); 1.4470 (0.38); 1.4226 (0.35); 1.4081 (0.34); 1.2236 (0.70); 1.1151 (3.04); 1.0917 (2.95); 1.0631 (0.41); 1.0510 (0.43); 1.0377 (0.41); 1.0071 (8.00); 0.9845 (7.58); 0.9257 (10.78); 0.9025 (10.63); 0.8823 (1.68); 0.8590 (1.39); −0.0002 (9.77); −0.0631 (0.60)

Example 10, Solvent: DMSO, Spectrometer: 300,16 MHz
9.4694 (1.01); 9.4493 (2.06); 7.3198 (1.47); 7.3140 (0.81); 7.2239 (0.57); 7.1975 (1.45); 7.1708 (1.90); 7.1400 (4.67); 7.1344 (2.08); 7.1142 (2.67); 7.1049 (1.33); 7.0885 (1.40); 7.0792 (0.73); 6.9993 (2.10); 6.9739 (1.52); 6.9609 (1.67); 6.9551 (0.87); 3.9669 (0.38); 3.9212 (16.00); 3.3241 (62.92); 3.0711 (0.71); 3.0570 (0.77); 3.0487 (0.74); 3.0329 (0.75); 2.9182 (0.39); 2.8867 (0.45); 2.8614 (0.33); 2.8266 (1.10); 2.8084 (1.54); 2.7787 (0.68); 2.7583 (0.40); 2.7205 (0.84); 2.7091 (0.61); 2.6581 (0.33); 2.5130 (7.43); 2.5071 (16.07); 2.5010 (22.30); 2.4949 (16.50); 2.4890 (8.08); 1.8086 (0.87); 1.7730 (0.44); 1.6279 (0.36); 1.5948 (1.03); 1.5714 (1.36); 1.5408 (0.75); 1.4190 (0.33); 1.2198 (0.53); 1.1307 (2.62); 1.1074 (2.60); 1.0496 (0.33); 1.0051 (5.62); 0.9824 (5.49); 0.9409 (5.98); 0.9180 (7.25); 0.8974 (2.82); 0.0107 (0.47); −0.0002 (14.78); −0.0111 (0.70); −0.0650 (0.58)

Example 11, Solvent: CDCl3, Spectrometer: 499,93 MHz
7.8325 (1.25); 7.8166 (1.40); 7.7848 (1.20); 7.2568 (12.59); 7.2379 (0.84); 7.2252 (1.41); 7.2030 (1.20); 7.1874 (2.41); 7.1712 (1.85); 7.1527 (0.55); 7.1172 (2.58); 7.0350 (2.25); 7.0196 (1.95); 7.0092 (1.42); 3.9886 (0.33); 3.9533 (15.28); 2.6977 (0.42); 2.6933 (0.44); 2.6844 (0.42); 2.6730 (0.81); 2.6640 (1.01); 2.6596 (1.01); 2.6508

(0.88); 2.6268 (0.75); 2.6123 (0.97); 2.6091 (0.98); 2.5942 (1.05); 2.5786 (0.48); 2.5753 (0.48); 2.5567 (0.58); 2.5417 (1.46); 2.5274 (1.53); 2.5134 (0.60); 2.2687 (0.38); 1.8166 (0.56); 1.8027 (0.68); 1.7984 (0.72); 1.7896 (0.84); 1.7847 (0.73); 1.7758 (0.86); 1.7715 (0.91); 1.7575 (0.69); 1.6784 (1.34); 1.5358 (1.61); 1.5277 (1.31); 1.5172 (1.03); 1.5139 (1.02); 1.5028 (0.92); 1.4898 (0.76); 1.4868 (0.77); 1.4778 (0.66); 1.4313 (3.05); 1.2568 (1.00); 1.1871 (9.25); 1.1727 (9.32); 0.9528 (15.44); 0.9387 (16.00); 0.9220 (1.31); 0.9071 (0.77); 0.8957 (0.69); 0.8811 (0.46); 0.0697 (1.99); 0.0060 (0.41); −0.0002 (8.70)

Example 12, Solvent: CDCl3, Spectrometer: 499,93 MHz
7.8148 (1.24); 7.7989 (1.29); 7.5253 (0.32); 7.5097 (0.88); 7.2567 (18.06); 7.2377 (0.53); 7.1961 (1.08); 7.1804 (2.27); 7.1702 (0.65); 7.1647 (1.37); 7.1525 (0.43); 7.1468 (1.53); 7.0391 (3.07); 7.0283 (2.05); 7.0129 (1.67); 6.9702 (0.39); 6.9313 (1.50); 3.8543 (10.08); 2.6687 (0.33); 2.6641 (0.36); 2.6551 (0.33); 2.6439 (0.73); 2.6350 (0.86); 2.6304 (0.88); 2.6216 (0.74); 2.6048 (0.65); 2.5906 (0.82); 2.5870 (0.83); 2.5724 (0.88); 2.5523 (0.71); 2.5375 (1.51); 2.5225 (1.39); 2.5086 (0.45); 2.4554 (0.36); 2.4411 (0.33); 2.2687 (0.41); 1.8150 (0.62); 1.8010 (0.71); 1.7964 (0.84); 1.7880 (0.87); 1.7830 (0.74); 1.7741 (0.87); 1.7700 (0.94); 1.7560 (0.72); 1.6780 (1.02); 1.5434 (0.52); 1.5254 (0.73); 1.5181 (0.83); 1.5164 (0.84); 1.5133 (0.88); 1.5116 (0.91); 1.5044 (0.81); 1.5025 (0.82); 1.5006 (0.79); 1.4984 (0.77); 1.4913 (0.69); 1.4895 (0.69); 1.4865 (0.71); 1.4848 (0.71); 1.4777 (0.59); 1.4313 (3.55); 1.2568 (0.64); 1.1844 (9.58); 1.1700 (10.21); 1.1545 (1.79); 0.9508 (15.12); 0.9350 (16.00); 0.9300 (4.43); 0.9219 (0.93); 0.9068 (0.42); 0.8957 (0.39); 0.0695 (4.15); 0.0063 (0.40); −0.0002 (12.36); −0.0067 (0.65)

Example 13, Solvent: DMSO, Spectrometer: 300,16 MHz
9.2496 (1.23); 7.3260 (0.87); 7.2651 (0.63); 7.2401 (0.86); 7.1469 (2.07); 7.1358 (0.76); 7.1103 (1.44); 7.0847 (0.86); 7.0292 (1.12); 7.0065 (0.69); 6.9678 (0.99); 3.8286 (5.17); 3.3274 (40.69); 2.8133 (0.72); 2.7917 (1.55); 2.7698 (0.80); 2.5134 (2.86); 2.5074 (6.42); 2.5013 (9.03); 2.4952 (6.73); 2.4892 (3.29); 2.3891 (3.22); 1.5244 (0.94); 1.5019 (2.04); 1.4797 (0.93); 0.9332 (16.00); −0.0002 (5.81)

Example 14, Solvent: DMSO, Spectrometer: 300,16 MHz
9.4560 (1.22); 7.3159 (0.73); 7.2555 (0.43); 7.2293 (0.60); 7.1369 (2.03); 7.1133 (1.25); 7.0877 (0.74); 7.0343 (1.07); 7.0071 (0.66); 6.9573 (0.80); 5.7585 (3.35); 3.9186 (6.60); 3.3250 (85.40); 3.2592 (0.39); 2.8153 (0.75); 2.7934 (1.50); 2.7702 (0.86); 2.5133 (6.13); 2.5073 (13.51); 2.5012 (18.89); 2.4951 (13.93); 2.4891 (6.71); 2.4249 (3.23); 1.5253 (0.92); 1.5029 (2.03); 1.4807 (0.96); 0.9329 (16.00); 0.0107 (0.44); −0.0002 (15.83); −0.0112 (0.69)

Example 15, Solvent: DMSO, Spectrometer: 400,13 MHz
9.3928 (2.51); 7.3481 (1.71); 7.3459 (1.77); 7.3286 (2.15); 7.3262 (2.24); 7.2910 (1.44); 7.2649 (0.86); 7.2468 (1.30); 7.1995 (1.77); 7.1800 (2.32); 7.1566 (3.17); 7.0221 (1.43); 5.7667 (0.51); 3.9248 (14.48); 3.3919 (0.68); 3.3417 (83.14); 3.2921 (0.92); 2.7638 (0.64); 2.7512 (0.40); 2.7334 (0.69); 2.7206 (1.26); 2.7079 (0.68); 2.6589 (0.58); 2.6434 (0.78); 2.6357 (0.76); 2.6193 (0.79); 2.6000 (0.39); 2.5923 (0.44); 2.5767 (0.36); 2.5606 (0.35); 2.5329 (0.58); 2.5281 (0.94); 2.5194 (11.77); 2.5150 (24.67); 2.5105 (33.73); 2.5060 (24.21); 2.5015 (11.26); 2.4652 (0.33); 2.4607 (0.41); 1.7798 (0.60); 1.7746 (0.55); 1.7629 (0.71); 1.7576 (0.57); 1.7466 (0.76); 1.7305 (0.38); 1.6615 (0.52); 1.6549 (0.57); 1.6446 (0.65); 1.6371 (0.98); 1.6303 (0.75); 1.6197 (0.83); 1.6135 (0.71); 1.5661 (0.42); 1.5517 (0.47); 1.5421 (0.65); 1.5335 (0.53); 1.5273 (0.68); 1.5186 (0.59); 1.5097 (0.62); 1.5037 (0.41); 1.4948 (0.48); 1.2887 (16.00); 1.2396 (0.35); 1.1348 (14.66); 0.9720 (8.71); 0.9551 (8.23); 0.9142 (0.51); 0.8991 (0.54)

Example 16, Solvent: CDCl3, Spectrometer: 300,16 MHz
7.6861 (0.79); 7.6055 (0.67); 7.5893 (0.71); 7.5763 (0.77); 7.5602 (0.72); 7.2616 (3.70); 7.0788 (2.46); 6.9267 (0.90); 6.8987 (1.97); 6.8873 (0.99); 6.8580 (0.84); 3.9522 (11.61); 2.6404 (1.28); 2.6199 (2.71); 2.5988 (1.61); 1.8284 (0.39); 1.8189 (0.41); 1.8079 (0.97); 1.7975 (0.96); 1.7899 (1.27); 1.7760 (1.06); 1.7695 (1.44); 1.7551 (0.53); 1.7492 (0.59); 1.6599 (2.07); 1.6536 (1.48); 1.6412 (1.24); 1.6316 (1.13); 1.6222 (1.24); 1.5824 (1.22); 1.3832 (16.00); 1.3777 (16.00); −0.0002 (3.06)

Example 17, Solvent: CDCl3, Spectrometer: 300,16 MHz
8.6484 (0.51); 7.2995 (0.58); 7.2835 (0.62); 7.2703 (0.80); 7.2621 (4.19); 7.2551 (0.76); 7.1862 (0.74); 7.0060 (1.52); 6.9668 (0.62); 6.9379 (0.59); 6.9278 (0.67); 6.8990 (0.52); 6.8259 (0.76); 4.1543 (1.16); 4.1304 (3.49); 4.1066 (3.55); 4.0829 (1.21); 3.9237 (6.82); 2.6811 (0.78); 2.6608 (1.62); 2.6397 (1.01); 2.1682 (1.81); 2.0423 (16.00); 1.7823 (0.66); 1.7652 (0.91); 1.7497 (0.90); 1.7314 (0.53); 1.7236 (0.38); 1.6796 (0.42); 1.6688 (1.33); 1.6632 (1.30); 1.6498 (0.96); 1.6420 (0.92); 1.6321 (0.86); 1.5763 (1.45); 1.4003 (9.53); 1.3951 (9.60); 1.3561 (0.73); 1.3304 (0.56); 1.3067 (1.10); 1.2817 (6.06); 1.2664 (6.94); 1.2580 (13.11); 1.2341 (4.73); 0.9036 (2.42); 0.8818 (7.87); 0.8585 (2.96); −0.0002 (3.45)

Example 18, Solvent: DMSO, Spectrometer: 400,13 MHz
9.5352 (3.08); 7.8126 (2.18); 7.8097 (2.32); 7.7928 (2.44); 7.7899 (2.40); 7.4060 (1.79); 7.3890 (2.24); 7.3866 (2.14); 7.2784 (1.72); 7.2493 (2.05); 7.2296 (3.48); 7.2099 (1.57); 7.1441 (4.10); 7.0099 (1.92); 5.7529 (5.93); 4.2032 (2.01); 4.1857 (6.55); 4.1681 (6.67); 4.1505 (2.09); 3.8308 (11.79); 3.3071 (53.36); 2.6731 (2.21); 2.6568 (3.84); 2.6402 (2.33); 2.6191 (1.90); 2.6042 (3.12); 2.5888 (2.04); 2.5089 (7.55); 2.5045 (15.70); 2.4999 (21.40); 2.4954 (15.04); 2.4910 (6.95); 1.9875 (0.45); 1.7539 (0.60); 1.7376 (1.79); 1.7217 (2.42); 1.7070 (1.71); 1.6905 (0.52); 1.4363 (0.47); 1.3554 (0.49); 1.2845 (7.35); 1.2670 (16.00); 1.2494 (7.23); 0.0080 (0.61); −0.0002 (20.10); −0.0085 (0.67)

Example 19, Solvent: DMSO, Spectrometer: 400,13 MHz
9.5370 (2.03); 7.8019 (1.38); 7.7994 (1.43); 7.7822 (1.52); 7.7796 (1.48); 7.4148 (1.13); 7.3966 (1.42); 7.2773 (1.09); 7.2536 (1.25); 7.2339 (2.11); 7.2142 (0.96); 7.1430 (2.54); 7.0089 (1.23); 5.7527 (0.77); 3.9190 (16.00); 3.8307 (7.66); 3.7662 (0.62); 3.3076 (53.74); 2.6696 (1.50); 2.6533 (2.56); 2.6367 (1.56); 2.6196 (1.29); 2.6048 (2.09); 2.5892 (1.35); 2.5090 (5.78); 2.5045 (11.55); 2.5000 (15.40); 2.4955 (10.78); 2.4911 (5.02); 1.7527 (0.40); 1.7364 (1.19); 1.7209 (1.64); 1.7058 (1.12); 1.6896 (0.36); 0.0079 (0.43); −0.0002 (11.18); −0.0085 (0.43)

Example 20, Solvent: DMSO, Spectrometer: 300,16 MHz
9.7782 (0.74); 7.8164 (0.41); 7.8127 (0.42); 7.7900 (0.46); 7.7863 (0.45); 7.3783 (0.32); 7.3092 (0.33); 7.2609 (0.35); 7.2346 (0.58); 7.1299 (0.73); 6.9507 (0.35); 5.7577 (2.11); 4.2130 (0.37); 4.1897 (1.16); 4.1663 (1.19); 4.1429 (0.38); 3.9431 (2.76); 3.3221 (16.00); 2.6827 (0.68); 2.6618 (1.16); 2.6459 (0.61); 2.5128 (1.90); 2.5070 (3.96); 2.5009 (5.41); 2.4949 (3.98); 2.4890 (1.94); 1.7527 (0.35); 1.7314 (0.45); 1.7122 (0.34); 1.2908 (1.28); 1.2674 (2.78); 1.2440 (1.28); −0.0002 (3.96)

Example 21, Solvent: DMSO, Spectrometer: 400,13 MHz
9.7283 (3.31); 7.8157 (2.06); 7.8128 (2.20); 7.7959 (2.29); 7.7931 (2.28); 7.4117 (1.12); 7.3925 (1.33); 7.2763 (1.59); 7.2545 (1.72); 7.2348 (2.92); 7.2152 (1.31); 7.1419 (3.68); 7.0076 (1.76); 4.2040 (2.00); 4.1864 (6.52); 4.1689 (6.61); 4.1513 (2.10); 3.9217 (14.31); 3.3068 (72.09); 2.6752 (2.20); 2.6592 (5.38); 2.6432 (4.72); 2.6300 (2.06); 2.5090 (10.43); 2.5045 (21.67); 2.4999 (29.48); 2.4954 (20.60); 2.4909 (9.42); 1.9876 (0.48); 1.7636

-continued (0.60); 1.7475 (1.75); 1.7319 (2.26); 1.7167 (1.65); 1.6999 (0.52); 1.2850 (7.33); 1.2674 (16.00); 1.2498 (7.20); 0.0080 (1.05); −0.0002 (34.09); −0.0085 (1.11)
Example 22, Solvent: DMSO, Spectrometer: 400,13 MHz
9.1938 (1.15); 7.3253 (0.67); 7.3056 (0.88); 7.3001 (1.05); 7.1657 (1.78); 7.1362 (0.71); 7.1169 (1.33); 7.0976 (0.72); 7.0315 (0.85); 6.9592 (1.00); 6.9417 (0.81); 3.8324 (5.39); 3.3155 (2.87); 2.6742 (0.80); 2.6574 (1.58); 2.6406 (0.84); 2.5378 (3.21); 2.5255 (0.88); 2.5166 (5.39); 2.5121 (10.70); 2.5076 (14.45); 2.5030 (10.39); 2.4985 (5.20); 1.5480 (0.92); 1.5312 (1.92); 1.5142 (0.90); 0.9493 (16.00)
Example 23, Solvent: DMSO, Spectrometer: 300,16 MHz
9.4357 (1.37); 7.3181 (0.92); 7.3104 (0.60); 7.2828 (0.66); 7.1387 (2.26); 7.1123 (1.26); 7.0866 (0.67); 6.9589 (1.63); 6.9312 (0.81); 3.9384 (7.28); 3.3232 (10.60); 2.7310 (0.75); 2.7086 (1.57); 2.6867 (0.82); 2.5325 (3.09); 2.5128 (1.68); 2.5068 (3.42); 2.5007 (4.75); 2.4946 (3.54); 2.4886 (1.74); 1.9886 (0.36); 1.5493 (0.89); 1.5271 (1.91); 1.5046 (0.88); 1.3551 (0.80); 0.9425 (16.00); 0.9097 (0.41); −0.0002 (3.54)
Example 24, Solvent: CDCl3, Spectrometer: 300,16 MHz
7.5852 (0.77); 7.5690 (0.83); 7.5560 (0.90); 7.5399 (0.87); 7.4107 (0.80); 7.2627 (1.87); 7.1766 (1.25); 6.9972 (2.56); 6.9164 (0.95); 6.8870 (0.96); 6.8769 (1.02); 6.8476 (0.89); 6.8178 (1.30); 3.8496 (8.16); 2.6161 (1.39); 2.5956 (2.92); 2.5746 (1.71); 2.0426 (0.57); 1.8249 (0.42); 1.8151 (0.44); 1.8043 (1.03); 1.7937 (1.07); 1.7862 (1.40); 1.7723 (1.15); 1.7660 (1.53); 1.7513 (0.57); 1.7458 (0.63); 1.6564 (2.21); 1.6504 (1.61); 1.6375 (1.38); 1.6283 (1.24); 1.6186 (1.38); 1.6126 (1.02); 1.3788 (16.00); 1.3735 (15.75); 1.2577 (0.42); −0.0002 (1.64)
Example 25, Solvent: DMSO, Spectrometer: 400,13 MHz
9.3964 (1.09); 7.3238 (0.43); 7.3047 (0.53); 7.2953 (0.83); 7.1608 (1.48); 7.1394 (0.63); 7.1201 (1.17); 7.1008 (0.61); 7.0263 (0.71); 6.9623 (1.00); 6.9441 (0.79); 3.9242 (6.91); 3.3150 (2.95); 2.7113 (0.75); 2.6947 (1.58); 2.6775 (0.85); 2.5397 (3.12); 2.5164 (5.57); 2.5119 (11.07); 2.5074 (14.84); 2.5029 (10.37); 2.4985 (4.78); 1.5529 (0.92); 1.5360 (1.92); 1.5190 (0.85); 0.9499 (16.00)
Example 26, Solvent: DMSO, Spectrometer: 300,16 MHz
9.7855 (2.57); 7.8028 (1.53); 7.7796 (1.69); 7.4121 (0.91); 7.3873 (1.20); 7.3096 (1.18); 7.2655 (1.28); 7.2393 (2.02); 7.2129 (0.90); 7.1303 (2.58); 6.9510 (1.23); 5.7585 (0.56); 3.9431 (10.41); 3.9203 (16.00); 3.8877 (0.50); 3.8614 (0.42); 3.3257 (14.74); 2.6786 (2.49); 2.6577 (3.83); 2.6354 (2.00); 2.5069 (5.03); 2.5010 (6.73); 2.4950 (4.99); 1.7717 (0.47); 1.7508 (1.35); 1.7305 (1.75); 1.7104 (1.26); −0.0002 (4.30)
Example 27, Solvent: DMSO, Spectrometer: 400,13 MHz
9.4020 (1.32); 7.2991 (0.74); 7.1643 (1.70); 7.1420 (0.61); 7.1230 (1.60); 7.1041 (1.13); 7.0469 (0.94); 7.0295 (1.39); 6.9288 (0.84); 6.9116 (0.71); 3.9279 (6.81); 3.3148 (6.79); 2.7954 (0.62); 2.7805 (1.31); 2.7649 (0.74); 2.5164 (7.58); 2.5120 (15.54); 2.5075 (21.04); 2.5031 (14.95); 2.4987 (7.03); 1.7202 (0.48); 1.7076 (0.71); 1.6936 (0.76); 1.6776 (0.35); 1.6276 (1.05); 1.6144 (0.72); 1.6087 (0.73); 1.6012 (0.59); 1.3560 (16.00)
Example 28, Solvent: DMSO, Spectrometer: 400,13 MHz
9.7338 (2.04); 7.8062 (1.45); 7.7878 (1.49); 7.4237 (0.89); 7.4030 (1.06); 7.2759 (0.75); 7.2599 (0.89); 7.2401 (1.41); 7.2234 (0.64); 7.1414 (1.44); 7.0116 (0.67); 7.0075 (0.71); 5.7585 (2.55); 5.7548 (2.46); 5.7528 (3.56); 3.9242 (15.99); 3.9220 (16.00); 3.3120 (28.91); 3.3065 (39.73); 3.2629 (0.33); 2.6578 (3.59); 2.6455 (3.26); 2.5047 (25.16); 2.5004 (25.09); 1.9932 (0.47); 1.9876 (0.58); 1.7482 (1.31); 1.7337 (1.77); 1.7185 (1.30); 1.1745 (0.39); 0.0055 (8.29); 0.0019 (8.42); −0.0002 (12.67)
Example 29, Solvent: DMSO, Spectrometer: 400,13 MHz
9.2638 (1.29); 7.2998 (0.70); 7.1653 (1.67); 7.1335 (0.64); 7.1145 (1.68); 7.0956 (1.22); 7.0398 (0.99); 7.0310 (0.90); 7.0240 (0.62); 6.9557 (0.85); 6.9532 (0.84); 6.9368 (0.70); 3.8430 (4.98); 3.3147 (6.37); 2.7919 (0.62); 2.7769 (1.31); 2.7613 (0.73); 2.5297 (0.41); 2.5164 (7.83); 2.5120 (15.68); 2.5074 (21.03); 2.5029 (14.75); 2.4985 (6.82); 1.7177 (0.49); 1.7051 (0.72); 1.6919 (0.76); 1.6778 (0.41); 1.6278 (1.06); 1.6149 (0.74); 1.6092 (0.73); 1.6020 (0.58); 1.3281 (16.00)
Example 30, Solvent: DMSO, Spectrometer: 400,13 MHz
9.5370 (1.87); 7.8020 (1.26); 7.7993 (1.34); 7.7821 (1.41); 7.7794 (1.39); 7.4147 (1.04); 7.3968 (1.30); 7.2773 (1.04); 7.2535 (1.19); 7.2338 (2.02); 7.2142 (0.92); 7.1431 (2.49); 7.0089 (1.17); 5.7529 (0.79); 3.9190 (16.00); 3.8306 (7.02); 3.3073 (36.81); 2.6695 (1.34); 2.6534 (2.31); 2.6366 (1.43); 2.6196 (1.16); 2.6046 (1.89); 2.5894 (1.21); 2.5090 (4.46); 2.5045 (9.21); 2.4999 (12.55); 2.4954 (8.74); 2.4910 (3.99); 1.9876 (0.38); 1.7528 (0.37); 1.7366 (1.08); 1.7211 (1.44); 1.7058 (1.01); 0.0080 (0.32); −0.0002 (9.86); −0.0085 (0.33)
Example 31, Solvent: CDCl3, Spectrometer: 300,16 MHz
8.6933 (0.38); 7.3641 (0.48); 7.3385 (0.72); 7.2605 (12.90); 7.2391 (0.47); 7.2129 (0.80); 7.1873 (0.42); 7.1070 (0.68); 7.0811 (0.46); 7.0252 (0.86); 6.8451 (0.43); 3.9686 (4.29); 3.7046 (16.00); 2.7746 (0.64); 2.7522 (1.27); 2.7296 (0.70); 2.5989 (2.14); 1.6122 (0.75); 1.5901 (1.40); 1.5676 (4.38); 1.4323 (0.50); 1.2553 (1.02); 0.9878 (15.69); 0.0694 (0.39); 0.0106 (0.37); −0.0002 (11.89); −0.0111 (0.63)
Example 32, Solvent: CDCl3, Spectrometer: 300,16 MHz
7.2769 (0.56); 7.2727 (0.55); 7.2605 (22.22); 7.2279 (0.35); 7.2029 (0.45); 7.1612 (0.56); 7.1009 (0.46); 7.0763 (0.34); 6.9816 (1.01); 6.8019 (0.52); 3.8362 (2.13); 3.7053 (3.56); 2.7405 (0.63); 2.7184 (1.36); 2.6959 (0.75); 2.5925 (2.17); 1.5986 (0.62); 1.5765 (1.16); 1.5531 (0.67); 1.5413 (5.94); 0.9828 (16.00); 0.0106 (0.58); −0.0002 (19.90); −0.0111 (0.85)
Example 33, Solvent: CDCl3, Spectrometer: 300,16 MHz
7.2608 (6.69); 7.2118 (0.36); 7.0441 (0.38); 3.9306 (1.92); 3.7046 (16.00); 2.7411 (0.62); 2.7193 (0.33); 2.5981 (1.00); 1.6091 (0.35); 1.5867 (0.63); 1.5643 (0.32); 1.5492 (2.77); 0.9867 (8.58); −0.0002 (6.07)

NMR Peak Lists Intermediates

Example III-a-1, Solvent: DMSO, Spectrometer: 400,13 MHz
7.4072 (0.71); 7.4044 (0.74); 7.3882 (0.84); 7.3855 (0.85); 7.2403 (0.49); 7.2210 (1.27); 7.2019 (1.03); 7.1904 (1.29); 7.1868 (1.35); 7.1711 (0.54); 7.1676 (0.44); 2.7062 (0.88); 2.6903 (1.83); 2.6744 (1.04);2.5162 (9.57); 2.5118 (19.10); 2.5074 (25.59); 2.5029 (18.14); 2.4986 (8.56); 1.7854 (0.67); 1.7776 (0.69); 1.7710 (0.90); 1.7619 (0.73); 1.7558 (0.85); 1.7400 (0.32); 1.6198 (1.30); 1.6137 (0.99);1.6048 (1.00); 1.5984 (0.87); 1.5907 (0.89);1.2545 (16.00)
Example III-a-2, Solvent: CDCl3, Spectrometer: 300,16 MHz
7.3040 (4.46); 7.0623 (1.18); 7.0363 (2.78); 7.0104 (1.76); 6.8797 (1.99);6.8773 (1.97); 6.8537 (1.52); 6.5699 (2.00); 6.5664 (1.82); 6.5443 (1.81); 6.5408 (1.63); 5.3452 (2.27); 3.6752 (0.91); 2.9112 (0.60); 2.8890 (0.90);

-continued 2.8728 (0.59); 2.8662 (0.63); 2.0669 (0.65); 2.0584 (0.73); 2.0496 (0.66);2.0414 (0.52); 2.0243 (0.64); 2.0182 (0.70); 2.0037 (0.84); 1.9888 (1.24); 1.9491 (0.99); 1.9413 (1.01); 1.9016 (0.42); 1.8943 (0.52); 1.6840 (0.59); 1.6762 (0.90); 1.6685 (0.96); 1.6612 (0.99); 1.6561 (0.73); 1.6412 (0.56);1.6338 (0.79); 1.6276 (0.95); 1.6213 (1.10); 1.5558 (1.23); 1.5416 (0.73); 1.5145 (0.85); 1.5061 (0.71); 1.4980 (0.61); 1.3789 (16.00); 1.3362 (0.38); 1.3234 (0.49); 1.2960 (9.12); 1.2724 (10.77); 1.2647 (15.36); 0.0499 (2.65)
Example III-a-3, Solvent: DMSO, Spectrometer: 400,13 MHz
6.8851 (0.43); 6.8657 (1.12); 6.8464 (0.85); 6.8110 (0.93); 6.8085 (1.00);6.7916 (0.56); 6.7890 (0.52); 6.5491 (0.86); 6.5462 (0.85); 6.5301 (0.77); 6.5271 (0.74); 5.3316 (1.96); 4.9414 (1.99); 4.9403 (1.98); 4.7940 (1.46); 4.0372 (0.39); 4.0195 (0.39); 3.3304 (5.99); 2.5104 (0.61); 2.5059 (1.28);2.5014 (1.74); 2.4969 (1.23); 2.4925 (0.58); 2.4539 (0.71); 2.4372 (1.50); 2.4205 (0.77); 1.9889 (1.75); 1.6380 (1.14); 1.6213 (2.41); 1.6044 (1.12); 1.4487 (0.57); 1.2518 (0.39); 1.2345 (0.41); 1.1919 (0.58); 1.1741 (1.09);1.1563 (0.59); 1.0771 (0.57); 1.0734 (0.82); 1.0643 (16.00); −0.0002 (1.91)
Example III-a-4, Solvent: DMSO, Spectrometer: 400,13 MHz
6.8079 (1.90); 6.7887 (4.05); 6.7695 (2.41); 6.4182 (2.99); 6.4154 (3.70);6.3987 (2.94); 6.3959 (3.33); 6.3514 (3.12); 6.3331 (2.94); 4.6584 (0.96); 3.3307 (8.71); 2.6991 (0.34); 2.6816 (1.17); 2.6695 (1.33); 2.6642 (1.39); 2.6521 (1.29); 2.6345 (0.47); 2.5095 (1.25); 2.5050 (2.77); 2.5004 (3.95); 2.4959 (2.97); 2.4915 (1.53); 2.4594 (1.07); 2.4525 (0.82); 2.4441 (0.87); 2.4363 (0.78); 2.4171 (1.15); 2.4093 (1.29); 2.4007 (1.80); 2.3934 (1.25); 2.3154 (0.89); 2.2974 (1.07); 2.2903 (1.16); 2.2722 (1.53); 2.2544 (0.66); 2.2473 (0.75); 2.2292 (0.64); 1.8596 (0.44); 1.8514 (0.56); 1.8485 (0.64); 1.8404 (0.80); 1.8317 (1.09); 1.8233 (1.09); 1.8207 (0.99); 1.8145 (0.99); 1.8065 (0.85); 1.8034 (0.83); 1.7952 (0.67); 1.6553 (0.52); 1.6473 (0.57); 1.6371 (0.66); 1.6306 (1.06); 1.6225 (1.34); 1.6142 (1.33); 1.6036 (1.77); 1.5866 (1.01); 1.5769 (1.25); 1.5702 (0.68); 1.5593 (1.18); 1.5537 (0.73); 1.5496 (0.90); 1.5444 (0.72); 1.5332 (0.76); 1.5279 (0.63); 1.5167 (0.44); 1.5003 (0.34); 1.0254 (15.93); 1.0076 (16.00); 0.9759 (0.33); 0.9625 (0.35); 0.9470(14.42); 0.9298 (14.16); 0.9099 (0.74); −0.0002 (5.12)
Example III-a-5, Solvent: CDCl3, Spectrometer: 499,93 MHz
7.2423 (2.07); 6.9830 (0.98); 6.9676 (2.08); 6.9522 (1.13); 6.6258 (1.74); 6.6105 (1.59); 6.5127 (1.63); 6.4973 (1.52); 3.5341 (1.46); 2.4917 (0.36); 2.4833 (0.65); 2.4688 (1.37); 2.4593 (1.00); 2.4529 (1.68); 2.4457 (1.02); 2.4372 (1.68); 2.4225 (0.90); 2.4198 (0.89); 2.4050 (0.84); 1.8123 (0.56); 1.7980 (0.64); 1.7945 (0.65); 1.7855 (0.73); 1.7802 (0.60); 1.7710 (0.77); 1.7679 (0.79); 1.7534 (0.64); 1.5463 (2.05); 1.5177 (0.54); 1.5161 (0.54); 1.5067 (0.63); 1.5043 (0.65); 1.5025 (0.59); 1.4948 (0.58); 1.4926 (0.67); 1.4797 (0.55); 1.4777 (0.55); 1.4758 (0.49); 1.4682 (0.43); 1.4666 (0.42); 1.1673 (9.95); 1.1530 (9.84); 0.9358 (16.00); 0.9279 (15.46); −0.0002(1.44)
Example III-a-6, Solvent: DMSO, Spectrometer: 300,16 MHz
6.7886 (0.56); 6.7631 (1.23); 6.7377 (0.75); 6.4262 (1.05); 6.4005 (0.92); 6.3289 (0.91); 6.3038 (0.85); 4.6381 (1.70); 3.3301 (2.47); 2.6667 (0.96); 2.6448 (1.90); 2.6232 (1.09); 2.4992 (0.67); 2.4940 (0.53); 2.1355 (3.03); 1.4655 (1.20); 1.4434 (2.33); 1.4213 (1.15); 1.2321 (0.37); 1.0651 (0.52); 1.0443 (0.53); 0.9547 (16.00); −0.0002 (0.38)
Example III-a-8, Solvent: DMSO, Spectrometer: 400,13 MHz
6.6674 (0.87); 6.6460 (1.08); 6.6362 (0.93); 6.6147 (1.04); 6.4678 (1.46); 6.4562 (1.54); 6.4463 (1.26); 6.4347 (1.20); 4.5397 (2.95); 3.3237 (1.38); 2.5160 (1.32); 2.5118 (2.53); 2.5073 (3.35); 2.5030 (2.43); 2.3359 (1.54); 2.3202 (3.07); 2.3044 (1.69); 1.7242 (0.46); 1.7171 (0.46); 1.7086 (1.16); 1.7010 (1.10); 1.6946 (1.52); 1.6852 (1.13); 1.6794 (1.48); 1.6691 (0.50); 1.6636 (0.60); 1.5678 (2.25); 1.5623 (1.55); 1.5529 (1.55); 1.5461 (1.32); 1.5389 (1.47); 1.2905 (15.90); 1.2869 (16.00)
Example III-a-9, Solvent: DMSO, Spectrometer: 300,16 MHz
7.1435 (1.97); 7.1398 (2.05); 7.1174 (2.52); 7.1136 (2.40); 6.8988 (1.62); 6.8727 (3.21); 6.8466 (1.67); 6.6232 (2.69); 6.6191 (2.79); 6.5971 (2.37); 6.5931 (2.22); 4.9078 (4.76); 4.4534 (2.14); 4.1300 (6.97); 4.1065 (7.11); 4.0831 (2.29); 3.3251 (19.52); 2.6184 (2.30); 2.5975 (3.65); 2.5743 (2.71); 2.5130 (1.59); 2.5070 (3.41); 2.5009 (4.70); 2.4948 (3.44); 2.4887 (1.67); 2.4483 (1.94); 2.4279 (3.62); 2.4073 (2.22); 1.7683 (0.65); 1.7465 (1.88); 1.7256 (2.51); 1.7046 (1.76); 1.6829 (0.59); 1.2606 (7.36); 1.2372 (16.00); 1.2137 (7.18); −0.0002 (3.03)
Example III-a-10, Solvent: DMSO, Spectrometer: 300,16 MHz
7.1333 (1.07); 7.1296 (1.11); 7.1071 (1.37); 7.1034 (1.32); 6.9027 (0.88); 6.8766 (1.73); 6.8505 (0.91); 6.6299 (1.46); 6.6259 (1.50); 6.6039 (1.28); 6.5998 (1.21); 4.9164 (2.59); 3.8618 (16.00); 3.3272 (6.95); 2.6134 (1.30); 2.5924 (2.06); 2.5693 (1.55); 2.5127 (0.50); 2.5067 (1.04); 2.5006 (1.43); 2.4945 (1.06); 2.4886 (0.52); 2.4481 (1.09); 2.4276 (2.02); 2.4070 (1.26); 1.7672 (0.37); 1.7453 (1.07); 1.7244 (1.43); 1.7033 (1.00); 1.6819 (0.33); −0.0002 (0.74)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for 1H spectra, we use tetramethylsilane and/or the chemical shift of the solvent used, especially in the case of spectra measured in DMSO. Therefore in NMR peak lists, tetramethylsilane peak can occur but not necessarily.

The 1H-NMR peak lists are similar to classical 1H-NMR prints and contain therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity>90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical 1H-NMR interpretation.

Further details of NMR-data description with peak lists you find in the publication, Citation of NMR Peaklist Data within patent applications "of the Research Disclosure Database Number 564025.

Example

In Vivo Preventive Test on *Alternaria brassicae* (Leaf Spot on Radish)

The active ingredients tested are prepared by homogenization in a mixture of acetone/tween/DMSO, and then diluted with water to obtain the desired active material concentration.

Radish plants ("Pernod Clair" variety), sown in starter cups on a 50/50 peat soil-pozzolana substrate and grown at 17° C., are treated at the cotyledon stage by spraying with the active ingredient prepared as described above. Plants, used as controls, are treated with the mixture of acetone/tween/DMSO/water not containing the active material.

After 24 hours, the plants are contaminated by spraying the cotyledons with an aqueous suspension of *Alternaria brassicae* spores (50 000 spores per ml). The spores are collected from a 15-day-old culture. The contaminated radish plants are incubated at 20° C. and at 100% relative humidity.

Grading (% of efficacy) is carried out 6 days after the contamination, in comparison with the control plants.

Under these conditions, good (at least 70%) or total protection is observed at a dose of 500 ppm with the following compounds:

| Ex_no. | Eff. % |
| --- | --- |
| 1 | 93 |
| 3 | 93 |
| 4 | 92 |
| 6 | 97 |
| 7 | 97 |
| 8 | 97 |
| 14 | 71 |
| 18 | 83 |
| 19 | 96 |
| 22 | 80 |
| 24 | 75 |
| 25 | 70 |
| 30 | 96 |

Under these conditions, good (at least 70%) or total protection is observed at a dose of 100 ppm with the following compounds:

| Ex_no. | Eff. % |
| --- | --- |
| 32 | 75 |
| 33 | 75 |

Example

In Vivo Preventive Test on *Botrytis cinerea* (Grey Mould)

The active ingredients tested are prepared by homogenization in a mixture of acetone/tween/DMSO and then diluted with water to obtain the desired active material concentration.

Gherkin plants ("Vert petit de Paris" variety), sown in starter cups on a 50/50 peat soil-pozzolana substrate and grown at 24° C., are treated at the Z11 cotyledon stage by spraying with the active ingredient prepared as described above. Plants, used as controls, are treated with the mixture of acetone/tween/DMSO/water not containing the active material.

After 24 hours, the plants are contaminated by spraying the cotyledons with an aqueous suspension of cryopreserved *Botrytis cinerea* spores (50 000 spores per ml). The spores are suspended in a nutrient solution composed of 10 g/L of PDB, 50 g/L of D-Fructose, 2 g/L of $NH_4NO_3$ and 1 g/L of $KH_2PO_4$. The contaminated gherkin plants are incubated at 17° C. and at 90% relative humidity.

Grading (% of efficacy) is carried out 4 to 5 days after the contamination, in comparison with the control plants.

Under these conditions, good (at least 70%) or total protection is observed at a dose of 500 ppm with the following compounds:

| Ex_no. | Eff. % |
| --- | --- |
| 3 | 100 |
| 5 | 93 |
| 6 | 97 |
| 19 | 96 |
| 22 | 99 |
| 25 | 97 |
| 30 | 96 |

Under these conditions, good (at least 70%) or total protection is observed at a dose of 100 ppm with the following compounds:

| Ex_no. | Eff. % |
| --- | --- |
| 32 | 73 |

Example

In Vivo Preventive Test on *Pyrenophora teres* (Net Blotch on Barley)

The active ingredients tested are prepared by homogenization in a mixture of acetone/tween/DMSO, and then diluted with water to obtain the desired active material concentration.

Barley plants ("Plaisant" variety), sown in starter cups on a 50/50 peat soil-pozzolana substrate and grown at 22° C., are treated at the 1-leaf stage (10 cm height) by spraying with the active ingredient prepared as described above. Plants, used as controls, are treated with the mixture of acetone/tween/DMSO/water not containing the active material.

After 24 hours, the plants are contaminated by spraying the leaves with an aqueous suspension of *Pyrenophora teres* spores (12 000 spores per ml). The spores are collected from a 12-day-old culture. The contaminated barley plants are incubated for 48 hours at 20° C. and at 100% relative humidity, and then for 12 days at 20° C. at 70-80% relative humidity.

Grading (% of efficacy) is carried out 14 days after the contamination, in comparison with the control plants.

Under these conditions, good (at least 70%) or total protection is observed at a dose of 500 ppm with the following compounds:

| Ex_no. | Eff. % |
|---|---|
| 6 | 80 |
| 8 | 71 |
| 9 | 86 |
| 10 | 86 |
| 12 | 81 |
| 13 | 75 |
| 14 | 97 |
| 18 | 92 |
| 21 | 75 |
| 22 | 70 |

Under these conditions, good (at least 70%) or total protection is observed at a dose of 100 ppm with the following compounds:

| Ex_no. | Eff. % |
|---|---|
| 32 | 83 |

Example

In Vivo Preventive Test on *Pyricularia oryzae* (Rice Blast)

The active ingredients tested are prepared by homogenization in a mixture of acetone/tween/DMSO, and then diluted with water to obtain the desired active material concentration.

Rice plants ("Koshihikari" variety), sown in starter cups on a 50/50 peat soil-pozzolana substrate and grown at 26° C., are treated at the 2-leaf stage (10 cm height) by spraying with the active ingredient prepared as described above. Plants, used as controls, are treated with the mixture of acetone/tween/DMSO/water not containing the active material.

After 24 hours, the plants are contaminated by spraying the leaves with an aqueous suspension of *Pyricularia oryzae* spores (40 000 spores per ml). The spores are collected from a 15-day-old culture and are suspended in water containing 2.5 g/l of gelatin. The contaminated rice plants are incubated at 25° C. and at 80% relative humidity.

Grading (% of efficacy) is carried out 6 days after the contamination, in comparison with the control plants.

Under these conditions, good (at least 70%) or total protection is observed at a dose of 500 ppm with the following compounds:

| Ex_no. | Eff. % |
|---|---|
| 12 | 71 |

Example

In Vivo Preventive Test on *Puccinia recondita* (Brown Rust on Wheat)

The active ingredients tested are prepared by homogenization in a mixture of acetone/tween/DMSO, and then diluted with water to obtain the desired active material concentration.

Wheat plants ("Scipion" variety), sown in starter cups on a 50/50 peat soil-pozzolana substrate and grown at 22° C., are treated at the 1-leaf stage (10 cm height) by spraying with the active ingredient prepared as described above. Plants, used as controls, are treated with the mixture of acetone/tween/DMSO/water not containing the active material.

After 24 hours, the plants are contaminated by spraying the leaves with an aqueous suspension of *Puccinia recondita* spores (100 000 spores per ml). The spores are collected from an infected plant and are suspended in water containing 2.5 ml/l of Tween 80 at 10%. The contaminated wheat plants are incubated for 24 hours at 20° C. and at 100% relative humidity, and then for 10 days at 20° C. and at 70-80% relative humidity.

Grading (% of efficacy) is carried out 12 days after the contamination, in comparison with the control plants.

Under these conditions, good (at least 70%) or total protection is observed at a dose of 500 ppm with the following compounds:

| Ex_no. | Eff. % |
|---|---|
| 1 | 100 |
| 2 | 98 |
| 3 | 94 |
| 4 | 94 |
| 5 | 94 |
| 6 | 89 |
| 7 | 100 |
| 8 | 100 |
| 9 | 94 |
| 10 | 94 |
| 11 | 98 |
| 12 | 100 |
| 13 | 97 |
| 14 | 100 |
| 15 | 98 |
| 16 | 97 |
| 17 | 100 |
| 21 | 94 |
| 22 | 94 |
| 23 | 79 |
| 24 | 97 |
| 25 | 98 |

Under these conditions, good (at least 70%) or total protection is observed at a dose of 100 ppm with the following compounds:

| Ex_no. | Eff. % |
|---|---|
| 32 | 94 |
| 33 | 94 |

Example

In Vivo Preventive Test on *Septoria tritici* (Leaf Spot on Wheat)

The active ingredients tested are prepared by homogenization in a mixture of acetone/tween/DMSO, and then diluted with water to obtain the desired active material concentration.

Wheat plants ("Scipion" variety), sown in starter cups on a 50/50 peat soil-pozzolana substrate and grown at 22° C., are treated at the 1-leaf stage (10 cm height) by spraying with the active ingredient prepared as described above. Plants, used as controls, are treated with the mixture of acetone/tween/DMSO/water not containing the active material.

After 24 hours, the plants are contaminated by spraying the leaves with an aqueous suspension of cryopreserved *Septoria tritici* spores (500 000 spores per ml). The contaminated wheat plants are incubated for 72 hours at 18° C. and at 100% relative humidity, and then for 21 days at 90% relative humidity.

Grading (% of efficacy) is carried out 24 days after the contamination, in comparison with the control plants.

Under these conditions, good (at least 70%) or total protection is observed at a dose of 500 ppm with the following compounds:

| Ex_no. | Eff. % |
|---|---|
| 1 | 88 |
| 6 | 75 |
| 9 | 83 |
| 10 | 83 |
| 13 | 95 |
| 14 | 90 |
| 15 | 75 |
| 22 | 83 |
| 25 | 100 |

Example

In Vivo Preventive Test on *Sphaerotheca fuliginea* (Powdery Mildew on Cucurbits)

The active ingredients tested are prepared by homogenization in a mixture of acetone/tween/DMSO and then diluted with water to obtain the desired active material concentration.

Gherkin plants ("Vert petit de Paris" variety), sown in starter cups on a 50/50 peat soil-pozzolana substrate and grown at 24° C., are treated at the Z11 cotyledon stage by spraying with the active ingredient prepared as described above. Plants, used as controls, are treated with the mixture of acetone/tween/DMSO/water not containing the active material.

After 24 hours, the plants are contaminated by spraying the cotyledons with an aqueous suspension of *Sphaerotheca fuliginea* spores (100 000 spores per ml). The spores are collected from infected plants. The contaminated gherkin plants are incubated at about 20° C. and at 70-80% relative humidity.

Grading (% of efficacy) is carried out 12 days after the contamination, in comparison with the control plants.

Under these conditions, good (at least 70%) or total protection is observed at a dose of 500 ppm with the following compounds:

| Ex_no. | Eff. % |
|---|---|
| 6 | 70 |
| 8 | 85 |
| 9 | 100 |
| 10 | 89 |
| 12 | 100 |
| 13 | 98 |
| 14 | 98 |
| 15 | 70 |
| 22 | 100 |

Under these conditions, good (at least 70%) or total protection is observed at a dose of 100 ppm with the following compounds:

| Ex_no. | Eff. % |
|---|---|
| 32 | 98 |

Example

In Vivo Preventive Test on *Uromyces appendiculatus* (Bean Rust)

The active ingredients tested are prepared by homogenization in a mixture of acetone/tween/DMSO, and then diluted with water to obtain the desired active material concentration.

Bean plants ("Saxa" variety), sown in starter cups on a 50/50 peat soil-pozzolana substrate and grown at 24° C., are treated at the 2-leaf stage (9 cm height) by spraying with the active ingredient prepared as described above. Plants, used as controls, are treated with the mixture of acetone/tween/DMSO/water not containing the active material.

After 24 hours, the plants are contaminated by spraying the leaves with an aqueous suspension of *Uromyces appendiculatus* spores (150 000 spores per ml). The spores are collected from infected plants and are suspended in water containing 2.5 ml/1 of Tween 80 at 10%. The contaminated bean plants are incubated for 24 hours at 20° C. and at 100% relative humidity, and then for 10 days at 20° C. and at 70-80% relative humidity.

Grading (% of efficacy) is carried out 11 days after the contamination, in comparison with the control plants.

Under these conditions, good (at least 70%) or total protection is observed at a dose of 500 ppm with the following compounds:

| Ex_no. | Eff. % |
|---|---|
| 1 | 100 |
| 2 | 100 |
| 3 | 100 |
| 4 | 99 |
| 5 | 100 |
| 6 | 97 |
| 7 | 100 |
| 8 | 99 |
| 9 | 100 |
| 10 | 99 |
| 11 | 100 |
| 12 | 100 |
| 13 | 100 |
| 14 | 99 |
| 15 | 95 |
| 16 | 100 |
| 17 | 100 |
| 18 | 81 |
| 22 | 100 |
| 23 | 96 |
| 24 | 100 |
| 25 | 100 |

Under these conditions, good (at least 70%) or total protection is observed at a dose of 100 ppm with the following compounds:

| Ex_no. | Eff. % |
|---|---|
| 32 | 97 |
| 33 | 99 |

Example

In Vivo *Phakopsora* Test (Soybeans)/Preventive

Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of the causal agent of soybean rust (*Phakopsora pachyrhizi*) and stay for 24 h without light in an incubation cabinet at approximately 24° C. and a relative atmospheric humidity of 95%.

The plants remain in the incubation cabinet at approximately 24° C. and a relative atmospheric humidity of approximately 80% and a day/night interval of 12 h.

The test is evaluated 7 days after the inoculation. 0% means an efficacy which corresponds to that of the untreated control, while an efficacy of 100% means that no disease is observed.

In this test the following compounds according to the invention showed efficacy of 70% or even higher at a concentration of 10 ppm of active ingredient.

| Ex_no. | Eff. % |
|---|---|
| 2 | 96 |

Example

In Vivo *Fusarium nivale* (Var. *Majus*)-Test (Wheat)/Preventive

Solvent: 49 parts by weight of N,N-dimethylacetamide

Emulsifier: 1 part by weight of alkylaryl polyglycol ether

To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are slightly injured by using a sandblast and afterwards they are sprayed with a conidia suspension of *Fusarium nivale* (var. *majus*).

The plants are placed in the greenhouse under a translucent incubation cabinet at a temperature of approximately 10° C. and a relative atmospheric humidity of approximately 100%.

The test is evaluated 5 days after the inoculation. 0% means an efficacy which corresponds to that of the untreated control, while an efficacy of 100% means that no disease is observed.

In this test the following compounds according to the invention showed an efficacy of 70% or even higher at a concentration of 500 ppm of active ingredient.

| Ex_no. | Eff. % |
|---|---|
| 1 | 92 |
| 2 | 86 |

Experimental Examples

Process (a)

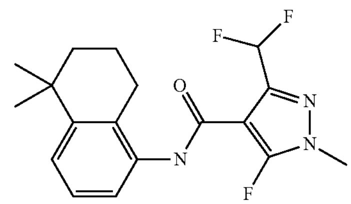

5-fluoro-3-(difluoromethyl)-N-(5,5-dimethyl-5,6,7,8-tetrahydronaphthalen-1-yl)-1-methyl-1H-pyrazole-4-carboxamide Example 1

In a 25 ml round bottom flask, a solution of 5,5-dimethyl-5,6,7,8-tetrahydronaphthalen-1-amine hydrochloride (200 mg, 0.954 mmol, 1 eq.) in 5 ml of DCM is cooled to 0° C. and triethylamine (0.290 ml, 2.078 mmol, 2.2 eq) is added followed by DMAP (11 mg, 0.094 mmol, 0.1 eq). A solution of 5-fluoro-3-(difluoromethyl)-1-methyl-1H-pyrazole-4-carbonyl chloride (220 mg, 1.039 mmol, 1.1 eq) in 1 ml of DCM is added dropwise. Stirring is allowed for 4 h at r.t. The reaction is quenched with 1N aq. HCl, and diluted with EtOAc. The aqueous layer was separated and extracted with EtOAc. The organics were combined, washed with NaOH 1N, dried over MgSO4 and concentrated. The crude material was purified by chromatography on silica gel to give pure material (70%)

Process (b)

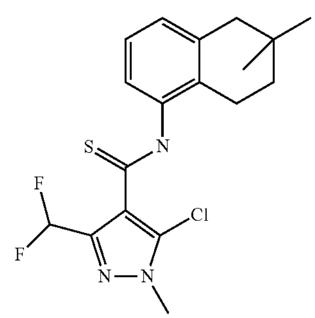

5-chloro-3-(difluoromethyl)-N-(6,6-dimethyl-5,6,7,8-tetrahydronaphthalen-1-yl)-1-methyl-1H-pyrazole-4-carbothioamide Example 33

In a microwave sealable tube, $P_2S_5$ (25 mg, 0.116 mmol, 0.5 eq) is added to a solution of 5-chloro-3-(difluoromethyl)-N-(6,6-dimethyl-5,6,7,8-tetrahydronaphthalen-1-yl)-1-methyl-1H-pyrazole-4-carboxamide (85 mg, 0.231 mmol, 1 eq) in 2 ml of dioxane. The tube is sealed and the reaction is microwaved 20 min at 130° C. The resulting solution is filtered through alumina and washed with dioxane. The solvent is evaporated and the residue purified by chromatography on silica gel to give pure material (94%)

Process (c)

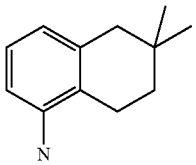

6,6-dimethyl-5,6,7,8-tetrahydronaphthalen-1-amine

Example III-a-12

In a sealable reactor, 5-bromo-2,2-dimethyl-1,2,3,4-tetrahydronaphthalene (1 eq) is dissolved in 1,4-dioxane (15 ml for 250 mg of SM), tBu-carbamate (1.5 eq) is added followed by XPHOS (0.1 eq) and cesium carbonate (2 eq). Argon is bubbled in solvent for 5 min and the reactor purged with Ar, Pd(OAc)$_2$ (0.05 eq) is added and the tube sealed. The reaction is heated at 100° C. until LCMS indicate no starting material left. The reaction is diluted with EA and filtered through celite. Solvent is removed under vac. and the residue dissolved in DCM. TFA (10 eq) is added. The reaction is refluxed for 5 h, cooled and quenched with NaHCO$_3$ sat., extracted with EA. Dried over MgSO$_4$ and concentrated. The residue is purified on silica gel to give pure material.

Process (d)

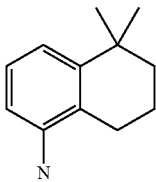

5,5-dimethyl-5,6,7,8-tetrahydronaphthalen-1-amine

Example III-a-1

1-(2-bromophenyl)-4-methylpentan-3-ol (17 g, 88.09 mmol) was added to polyphosphoric acid (170 g, 265.4 mmol). The mixture was heated to 130° C. for 20 minutes. The reaction progress was monitored by TLC (TLC system: 5% Ethyl acetate in hexanes, R$_f$=0.2). The reaction mass was cooled to room temperature, water (800 mL) was added and the mixture was further cooled to 0° C. and the pH of the mixture was adjusted to 10-12 using 50% solution of Sodium hydroxide. The mixture was extracted with Ethyl acetate (3×600 mL) and the organic layer was concentrated to dryness to obtain the crude product as a colorless oil (6.9 g, 49%)

The invention claimed is:

1. A 1-Methyl-3-dihalogenomethyl-5-halogenopyrazole (thio)tetrahydronaphthyl carboxamide compound of formula (I)

(I)

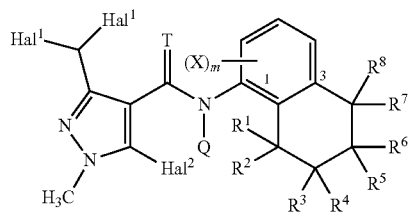

in which

Hal$^1$ represents chlorine or fluorine;
Hal$^2$ represents chlorine or fluorine;
T represents an oxygen or sulfur atom;
Q represents hydrogen, $C_1$-$C_6$-alkylsulfonyl, $C_1$-$C_4$-alkoxy-$C_1$-$C_4$-alkyl, $C_1$-$C_4$-haloalkylsulfonyl, halo-$C_1$-$C_4$-alkoxy-$C_1$-$C_4$-alkyl;
X represents halogen, nitro, cyano, $C_1$-$C_{12}$-alkyl; $C_1$-$C_6$-haloalkyl having 1 to 9 identical or different halogen atoms; $C_1$-$C_6$-alkoxy; $C_1$-$C_6$-haloalkoxy having 1 to 9 identical or different halogen atoms; $C_1$-$C_6$-alkylsulfanyl; $C_1$-$C_6$-haloalkylsulfanyl having 1 to 9 identical or different halogen atoms; $C_1$-$C_6$-alkylsulfonyl; $C_1$-$C_6$-haloalkylsulfonyl having 1 to 9 identical or different halogen atoms; $C_2$-$C_{12}$-alkenyl; $C_2$-$C_{12}$-alkynyl; $C_3$-$C_7$-cycloalkyl; phenyl; tri($C_1$-$C_8$)alkylsilyl; tri($C_1$-$C_8$)alkylsilyl-$C_1$-$C_8$-alkyl;
m represents 0, 1, 2 or 3
$R^1$, $R^2$, $R^3$, $R^4$, $R^5$, $R^6$, $R^7$ and $R^8$ independently one to another represent hydrogen; halogen; cyano; $C_1$-$C_{16}$-alkyl; $C_2$-$C_{16}$-haloalkyl having 1 to 9 identical or different halogen atoms; $C_3$-$C_8$-cycloalkyl; $C_3$-$C_7$-halocycloalkyl having 1 to 9 identical or different halogen atoms; $C_1$-$C_6$-haloalkyl having 1 to 9 identical or different halogen atoms; ($C_3$-$C_8$-cycloalkyl)-$C_1$-$C_8$-alkyl; ($C_3$-$C_8$-cycloalkyl)-$C_3$-$C_8$-cycloalkyl; $C_2$-$C_{16}$-alkenyl; $C_2$-$C_{16}$-alkynyl; $C_2$-$C_{16}$-alkenyl-$C_1$-$C_{16}$-alkyl; $C_2$-$C_{16}$-alkynyl-$C_1$-$C_{16}$-alkyl; $C_1$-$C_{16}$-alkoxy; $C_3$-$C_8$-cycloalkyloxy; ($C_3$-$C_8$-cycloalkyl)-$C_1$-$C_8$-alkyloxy; $C_1$-$C_8$-alkylsulfanyl; $C_3$-$C_8$-cycloalkylsulfanyl; ($C_3$-$C_8$-cycloalkyl)-$C_1$-$C_8$-alkylsulfanyl; $C_2$-$C_{16}$-alkenyloxy; $C_3$-$C_8$-alkynyloxy; aryl-$C_1$-$C_8$-alkyloxy which is optionally substituted by up to 6 identical or different groups $R^b$; aryl-$C_1$-$C_8$-alkylsulfanyl which is optionally substituted by up to 6 identical or different groups $R^b$; aryloxy which is optionally substituted by up to 6 identical or different groups $R^b$; arylsulfanyl which is optionally substituted by up to 6 identical or different groups $R^b$; ($C_3$-$C_8$-cycloalkyl)-$C_2$-$C_8$-alkenyl; ($C_3$-$C_8$-cycloalkyl)-$C_2$-$C_8$-alkynyl; tri($C_1$-$C_8$)alkylsilyl; tri($C_1$-$C_8$)alkylsilyl-$C_1$-$C_8$-alkyl; aryl-$C_1$-$C_8$-alkyl which is optionally substituted by up to 6 identical or different groups $R^b$; aryl-$C_2$-$C_8$-alkenyl which is optionally substituted by up to 6 identical or different groups $R^b$; aryl-$C_2$-$C_8$-alkynyl which is optionally substituted by up to 6 identical or different groups $R^b$; $C_1$-$C_8$-alkylamino; di-$C_1$-$C_8$-alkylamino; arylamino which is optionally substituted by up to 6 identical or different groups $R^b$; $C_1$-$C_8$-alkylcarbonyl; $C_1$-$C_8$-alkylcarbonyloxy; $C_1$-$C_8$-alkylcarbonylamino; $C_1$-$C_8$-alkoxycarbonyl; $C_1$-$C_8$-alkyloxycarbonyloxy; $C_1$-$C_8$-alkylcarbamoyl; di-$C_1$-$C_8$-alkylcarbamoyl; $C_1$-$C_8$-alkylaminocarbonyloxy; di-$C_1$-$C_8$-alkylaminocarbonyloxy; N—($C_1$-$C_8$-alkyl)hydroxycarbamoyl; $C_1$-$C_8$-alkoxycarbamoyl; N—($C_1$-$C_8$-alkyl)-$C_1$-$C_8$-alkoxycarbamoyl; aryl-$C_1$-$C_8$-alkylamino which is optionally substituted by up to 6 identical or different groups $R^b$; ($C_1$-$C_8$-alkoxyimino)-$C_1$-$C_8$-alkyl; ($C_2$-$C_8$-cycloalkoxyimino)-$C_1$-$C_8$-alkyl; $C_1$-$C_8$-alkyliminoxy; $C_1$-$C_8$-alkyliminoxy-$C_1$-$C_8$-alkyl; each of which is optionally substituted;
provided that $R^1$, $R^2$, $R^3$, $R^4$, $R^5$, $R^6$ and $R^7$ do not represent hydrogen at the same time when $R^8$ represents hydrogen or trifluoromethyl;
$R^1$ and $R^2$ can form together with the carbon to which they are attached a $C_3$-$C_8$-cycloalkyl; $C_3$-$C_8$-cycloalkenyl, or a saturated 5, 6 or 7 membered heterocycle; each of which is optionally substituted; or may represent a group =C($Y^1$)$Y^2$ or a group =N—O—$R^c$;
$R^3$ and $R^4$ can form together with the carbon to which they are attached a $C_3$-$C_8$-cycloalkyl; $C_3$-$C_8$-cycloalkenyl, or a saturated 5, 6 or 7 membered heterocycle; each of which is optionally substituted; or may represent a group =C(Y$^1$)Y$^2$ or a group =N—O—R$^c$;

R$^5$ and R$^6$ can form together with the carbon to which they are attached a C$_3$-C$_8$-cycloalkyl; C$_3$-C$_8$-cycloalkenyl, or a saturated 5, 6 or 7 membered heterocycle; each of which is optionally substituted; or may represent a group =C(Y$^1$)Y$^2$ or a group =N—O—R$^c$;

R$^7$ and R$^8$ can form together with the carbon to which they are attached a C$_3$-C$_8$-cycloalkyl; C$_3$-C$_8$-cycloalkenyl, or a saturated 5, 6 or 7 membered heterocycle; each of which is optionally substituted; or may represent a group =C(Y$^1$)Y$^2$ or a group =N—O—R$^c$;

R$^1$ and R$^3$ or R$^3$ and R$^5$ or R$^5$ and R$^7$ can form with the carbons to which they are attached a C$_3$-C$_8$-cycloalkyl; C$_3$-C$_8$-cycloalkenyl, or a saturated 5, 6 or 7 membered heterocycle; each of which is optionally substituted;

R$^b$ represents halogen; nitro, cyano, C$_1$-C$_{12}$-alkyl; C$_1$-C$_6$-haloalkyl having 1 to 9 identical or different halogen atoms; C$_1$-C$_6$-alkoxy; C$_1$-C$_6$-haloalkoxy having 1 to 9 identical or different halogen atoms; C$_1$-C$_6$-alkylsulfanyl; C$_1$-C$_6$-haloalkylsulfanyl having 1 to 9 identical or different halogen atoms; C$_1$-C$_6$-alkylsulfonyl; C$_1$-C$_6$-haloalkylsulfonyl having 1 to 9 identical or different halogen atoms; C$_2$-C$_{12}$-alkenyl; C$_2$-C$_{12}$-alkynyl; C$_3$-C$_7$-cycloalkyl; phenyl; tri(C$_1$-C$_8$)alkylsilyl; tri(C$_1$-C$_8$)alkylsilyl-C$_1$-C$_8$-alkyl;

Y$^1$ and Y$^2$ independently of one another represent hydrogen, halogen, C$_1$-C$_{12}$-alkyl; C$_1$-C$_6$-haloalkyl having 1 to 9 identical or different halogen atoms; C$_1$-C$_8$-alkylsulfanyl; phenyl; each of which is optionally substituted; or Y$^1$ and Y$^2$ can form together with the carbon to which they are attached a C$_3$-C$_8$-cycloalkyl or a C$_3$-C$_8$-cycloalkenyl or a saturated 5, 6 or 7 membered heterocycle; each of which is optionally substituted;

R$^c$ represents C$_1$-C$_{16}$-alkyl; C$_1$-C$_6$-haloalkyl having 1 to 9 identical or different halogen atoms; C$_3$-C$_8$-cycloalkyl; (C$_3$-C$_8$-cycloalkyl)-C$_1$-C$_8$-alkyl; (C$_3$-C$_8$-cycloalkyl)-C$_3$-C$_8$-cycloalkyl; C$_2$-C$_8$-alkenyl-C$_1$-C$_{16}$-alkyl; C$_2$-C$_8$-alkynyl-C$_1$-C$_{16}$-alkyl; aryl-C$_1$-C$_8$-alkyl which is optionally substituted by up to 6 identical or different groups R$^b$; each of which is optionally substituted.

2. 1-Methyl-3-dihalogenomethyl-5-halogenopyrazole (thio)tetrahydronaphthyl carboxamide of formula (I) according to claim 1, wherein Hal$^1$ represents chlorine or fluorine;
Hal$^2$ represents chlorine or fluorine;
T represents an oxygen atom;
Q represents hydrogen, C$_1$-C$_4$-alkylsulfonyl, C$_1$-C$_3$-alkoxy-C$_1$-C$_3$-alkyl, C$_1$-C$_4$-haloalkylsulfonyl, halo-C$_1$-C$_3$-alkoxy-C$_1$-C$_3$-alkyl having in each case 1 to 9 fluorine, chlorine and/or bromine atoms;
X represents fluorine, chlorine, methyl or trifluoromethyl;
m represents 0, 1 or 2;
R$^1$, R$^2$, R$^3$, R$^4$, R$^5$, R$^6$, R$^7$ and R$^8$ independently one to another represent hydrogen, halogen; cyano; C$_1$-C$_{16}$-alkyl; C$_1$-C$_6$-haloalkyl having 1 to 9 identical or different halogen atoms; C$_3$-C$_8$-cycloalkyl; (C$_3$-C$_8$-cycloalkyl)-C$_1$-C$_8$-alkyl; (C$_3$-C$_8$-cycloalkyl)-C$_3$-C$_8$-cycloalkyl; C$_2$-C$_8$-alkenyl; C$_2$-C$_8$-alkynyl; C$_2$-C$_8$-alkenyl-C$_1$-C$_{16}$-alkyl; C$_2$-C$_8$-alkynyl-C$_1$-C$_{16}$-alkyl; C$_1$-C$_{16}$-alkoxy; C$_3$-C$_8$-cycloalkyloxy; (C$_3$-C$_8$-cycloalkyl)-C$_1$-C$_8$-alkyloxy; C$_1$-C$_8$-alkylsulfanyl; C$_3$-C$_8$-cycloalkylsulfanyl; (C$_3$-C$_8$-cycloalkyl)-C$_1$-C$_8$-alkylsulfanyl; C$_2$-C$_8$-alkenyloxy; C$_3$-C$_8$-alkynyloxy; aryl-C$_1$-C$_8$-alkyloxy which is optionally substituted by up to 6 identical or different groups R$^b$; aryl-C$_1$-C$_8$-alkylsulfanyl which is optionally substituted by up to 6 identical or different groups R$^b$; aryloxy which is optionally substituted by up to 6 identical or different groups R$^b$; arylsulfanyl which is optionally substituted by up to 6 identical or different groups R$^b$; (C$_3$-C$_8$-cycloalkyl)-C$_2$-C$_8$-alkenyl; (C$_3$-C$_8$-cycloalkyl)-C$_2$-C$_8$-alkynyl; tri(C$_1$-C$_8$)alkylsilyl; tri(C$_1$-C$_8$)alkylsilyl-C$_1$-C$_8$-alkyl; aryl-C$_1$-C$_8$-alkyl which is optionally substituted by up to 6 identical or different groups R$^b$; aryl-C$_2$-C$_8$-alkenyl which is optionally substituted by up to 6 identical or different groups R$^b$; aryl-C$_2$-C$_8$-alkynyl which is optionally substituted by up to 6 identical or different groups R$^b$; each of which is optionally substituted; provided that R$^1$, R$^2$, R$^3$, R$^4$, R$^5$, R$^6$ and R$^7$ do not represent hydrogen at the same time when R$^8$ represents hydrogen or trifluoromethyl;

R$^1$ and R$^2$ can form together with the carbon to which they are attached an optionally substituted C$_3$-C$_8$-cycloalkyl; or may form the group =C(Y$^1$)Y$^2$ (where Y$^1$ and Y$^2$ independently of one another represent hydrogen, halogen, C$_1$-C$_{12}$-alkyl, C$_1$-C$_6$-haloalkyl having 1 to 9 identical or different halogen atoms or form together with the carbon to which they are attached an optionally substituted cyclopropyl, cyclobutyl, cyclopentyl, cyclohexyl) or a group =N—O—R$^c$ (where R$^c$ represents C$_1$-C$_{12}$-alkyl; C$_1$-C$_6$-haloalkyl having 1 to 9 identical or different halogen atoms; C$_3$-C$_6$-cycloalkyl; (C$_3$-C$_6$-cycloalkyl)-C$_1$-C$_6$-alkyl; (C$_3$-C$_6$-cycloalkyl)-C$_3$-C$_6$-cycloalkyl; C$_2$-C$_6$-alkenyl-C$_1$-C$_{12}$-alkyl; C$_2$-C$_6$-alkynyl-C$_1$-C$_{12}$-alkyl; aryl-C$_1$-C$_6$-alkyl which is optionally substituted by up to 6 identical or different groups R$^b$; each of which is optionally substituted);

R$^3$ and R$^4$ can form together with the carbon to which they are attached an optionally substituted C$_3$-C$_8$-cycloalkyl; or may form the group =C(Y$^1$)Y$^2$ (where Y$^1$ and Y$^2$ independently of one another represent hydrogen, halogen, C$_1$-C$_{12}$-alkyl, C$_1$-C$_6$-haloalkyl having 1 to 9 identical or different halogen atoms or form together with the carbon to which they are attached an optionally substituted cyclopropyl, cyclobutyl, cyclopentyl, cyclohexyl) or a group =N—O—R$^c$ (where R$^c$ represents C$_1$-C$_{12}$-alkyl; C$_1$-C$_6$-haloalkyl having 1 to 9 identical or different halogen atoms; C$_3$-C$_6$-cycloalkyl; (C$_3$-C$_6$-cycloalkyl)-C$_1$-C$_6$-alkyl; (C$_3$-C$_6$-cycloalkyl)-C$_3$-C$_6$-cycloalkyl; C$_2$-C$_6$-alkenyl-C$_1$-C$_{12}$-alkyl; C$_2$-C$_6$-alkynyl-C$_1$-C$_{12}$-alkyl; aryl-C$_1$-C$_6$-alkyl which is optionally substituted by up to 6 identical or different groups R$^b$; each of which is optionally substituted);

R$^5$ and R$^6$ can form together with the carbon to which they are attached an optionally substituted C$_3$-C$_8$-cycloalkyl; or may form the group =C(Y$^1$)Y$^2$ (where Y$^1$ and Y$^2$ independently of one another represent hydrogen, halogen, C$_1$-C$_{12}$-alkyl, C$_1$-C$_6$-haloalkyl having 1 to 9 identical or different halogen atoms or form together with the carbon to which they are attached an optionally substituted cyclopropyl, cyclobutyl, cyclopentyl, cyclohexyl) or a group =N—O—R$^c$ (where R$^c$ represents C$_1$-C$_{12}$-alkyl; C$_1$-C$_6$-haloalkyl having 1 to 9 identical or different halogen atoms; C$_3$-C$_6$-cycloalkyl; (C$_3$-C$_6$-cycloalkyl)-C$_1$-C$_6$-alkyl; (C$_3$-C$_6$-cycloalkyl)-C$_3$-C$_6$-cycloalkyl; C$_2$-C$_6$-alkenyl-C$_1$-C$_{12}$-alkyl; C$_2$-C$_6$-alkynyl-C$_1$-C$_{12}$-alkyl; aryl-C$_1$-C$_6$-alkyl which is optionally substituted by up to 6 identical or different groups R$^b$; each of which is optionally substituted);

R$^7$ and R$^8$ can form together with the carbon to which they are attached an optionally substituted C$_3$-C$_8$-cycloalkyl; or may form the group =C(Y$^1$)Y$^2$ (where Y$^1$ and Y$^2$ independently of one another represent hydrogen, halogen, C$_1$-C$_{12}$-alkyl, C$_1$-C$_6$-haloalkyl having 1 to 9 identical or different halogen atoms or form together with the carbon to which they are attached an optionally substituted cyclopropyl, cyclobutyl, cyclopentyl, cyclohexyl) or a group =N—O—R$^c$ (where R$^c$ represents C$_1$-C$_{12}$-alkyl; C$_1$-C$_6$-haloalkyl having 1 to 9 identical or different halogen atoms; $C_3$-$C_6$-cycloalkyl; ($C_3$-$C_6$-cycloalkyl)-$C_1$-$C_6$-alkyl; ($C_3$-$C_6$-cycloalkyl)-$C_3$-$C_6$-cycloalkyl; $C_2$-$C_6$-alkenyl-$C_1$-$C_{12}$-alkyl; $C_2$-$C_6$-alkynyl-$C_1$-$C_{12}$-alkyl; aryl-$C_1$-$C_6$-alkyl which is optionally substituted by up to 6 identical or different groups $R^b$; each of which is optionally substituted);

$R^1$ and $R^3$ or $R^3$ and $R^5$ or $R^5$ and $R^7$ can form with the carbons to which they are attached an optionally substituted $C_3$-$C_8$-cycloalkyl;

$R^b$ represents halogen; nitro, cyano, $C_1$-$C_8$-alkyl; $C_1$-$C_4$-haloalkyl having 1 to 9 identical or different halogen atoms; $C_1$-$C_6$-alkoxy; $C_1$-$C_4$-haloalkoxy having 1 to 9 identical or different halogen atoms; $C_1$-$C_6$-alkylsulfanyl; $C_1$-$C_4$-haloalkylsulfanyl having 1 to 9 identical or different halogen atoms; $C_1$-$C_6$-alkylsulfonyl; $C_1$-$C_4$-haloalkylsulfonyl having 1 to 9 identical or different halogen atoms; $C_2$-$C_8$-alkenyl; $C_2$-$C_8$-alkynyl; $C_3$-$C_6$-cycloalkyl; phenyl; tri($C_1$-$C_6$)alkylsilyl; tri($C_1$-$C_6$)alkylsilyl-$C_1$-$C_6$-alkyl.

3. 1-Methyl-3-dihalogenomethyl-5-halogenopyrazole (thio)tetrahydronaphthyl carboxamide of formula (I) according to claim 1, wherein
Hal$^1$ represents chlorine or fluorine;
Hal$^2$ represents chlorine or fluorine;
T represents an oxygen atom;
Q represents hydrogen, methylsulfonyl, ethylsulfonyl, n- or isopropylsulfonyl, n-, iso-, sec- or tert-butylsulfonyl, methoxymethyl, methoxyethyl, ethoxymethyl, ethoxyethyl, trifluoromethylsulfonyl, trifluoromethoxymethyl;
X represents fluorine, chlorine, methyl or trifluoromethyl located in the 4-, 5- or 6-position;
m represents 0 or 1;
$R^1$, $R^2$, $R^3$, $R^4$, $R^5$, $R^6$, $R^7$ and $R^8$ independently of one another represent hydrogen, fluorine, chlorine, bromine, iodine; $C_1$-$C_{12}$-alkyl; $C_1$-$C_6$-haloalkyl having 1 to 9 identical or different halogen atoms; $C_3$-$C_6$-cycloalkyl; ($C_3$-$C_6$-cycloalkyl)-$C_1$-$C_6$-alkyl; ($C_3$-$C_6$-cycloalkyl)-$C_3$-$C_6$-cycloalkyl; $C_1$-$C_{12}$-alkoxy; $C_3$-$C_6$-cycloalkyloxy; ($C_3$-$C_6$-cycloalkyl)-$C_1$-$C_6$-alkyloxy; each of which is optionally substituted; provided that $R^1$, $R^2$, $R^3$, $R^4$, $R^5$, $R^6$ and $R^7$ do not represent hydrogen at the same time when $R^8$ represents hydrogen or trifluoromethyl;

$R^1$ and $R^2$ can form together with the carbon to which they are attached an optionally substituted cyclopropyl, cyclobutyl, cyclopentyl, cyclohexyl; or may form the group =C($Y^1$)$Y^2$ (where $Y^1$ and $Y^2$ independently of one another represent hydrogen, fluorine, chlorine, bromine, methyl; ethyl, propyl, isopropyl) or a group =N—O—$R^c$ (where $R^c$ represents $C_1$-$C_8$-alkyl; $C_1$-$C_4$-haloalkyl having 1 to 9 identical or different fluorine, chlorine or bromine atoms; $C_3$-$C_6$-cycloalkyl; ($C_3$-$C_6$-cycloalkyl)-$C_1$-$C_4$-alkyl; $C_2$-$C_6$-alkenyl-$C_1$-$C_8$-alkyl; $C_2$-$C_6$-alkynyl-$C_1$-$C_8$-alkyl; aryl-$C_1$-$C_4$-alkyl which is optionally substituted by up to 5 identical or different groups $R^b$; each of which is optionally substituted);

$R^3$ and $R^4$ can form together with the carbon to which they are attached an optionally substituted cyclopropyl, cyclobutyl, cyclopentyl, cyclohexyl; or may form the group =C($Y^1$)$Y^2$ (where $Y^1$ and $Y^2$ independently of one another represent hydrogen, fluorine, chlorine, bromine, methyl; ethyl, propyl, isopropyl) or a group =N—O—$R^c$ (where $R^c$ represents $C_1$-$C_8$-alkyl; $C_1$-$C_4$-haloalkyl having 1 to 9 identical or different fluorine, chlorine or bromine atoms; $C_3$-$C_6$-cycloalkyl; ($C_3$-$C_6$-cycloalkyl)-$C_1$-$C_4$-alkyl; $C_2$-$C_6$-alkenyl-$C_1$-$C_8$-alkyl; $C_2$-$C_6$-alkynyl-$C_1$-$C_8$-alkyl; aryl-$C_1$-$C_4$-alkyl which is optionally substituted by up to 5 identical or different groups $R^b$; each of which is optionally substituted);

$R^5$ and $R^6$ can form together with the carbon to which they are attached an optionally substituted cyclopropyl, cyclobutyl, cyclopentyl, cyclohexyl; or may form the group =C($Y^1$)$Y^2$ (where $Y^1$ and $Y^2$ independently of one another represent fluorine, chlorine, bromine, methyl; ethyl, propyl, isopropyl) or a group =N—O—$R^c$ (where $R^c$ represents $C_1$-$C_8$-alkyl; $C_1$-$C_4$-haloalkyl having 1 to 9 identical or different fluorine, chlorine or bromine atoms; $C_3$-$C_6$-cycloalkyl; ($C_3$-$C_6$-cycloalkyl)-$C_1$-$C_4$-alkyl; $C_2$-$C_6$-alkenyl-$C_1$-$C_8$-alkyl; $C_2$-$C_6$-alkynyl-$C_1$-$C_8$-alkyl; aryl-$C_1$-$C_4$-alkyl which is optionally substituted by up to 5 identical or different groups $R^b$; each of which is optionally substituted);

$R^7$ and $R^8$ can form together with the carbon to which they are attached an optionally substituted cyclopropyl, cyclobutyl, cyclopentyl, cyclohexyl; or may form the group =C($Y^1$)$Y^2$ (where $Y^1$ and $Y^2$ independently of one another represent hydrogen, fluorine, chlorine, bromine, methyl; ethyl, propyl, isopropyl) or a group =N—O—$R^c$ (where $R^c$ represents $C_1$-$C_8$-alkyl; $C_1$-$C_4$-haloalkyl having 1 to 9 identical or different fluorine, chlorine or bromine atoms; $C_3$-$C_6$-cycloalkyl; ($C_3$-$C_6$-cycloalkyl)-$C_1$-$C_4$-alkyl; $C_2$-$C_6$-alkenyl-$C_1$-$C_8$-alkyl; $C_2$-$C_6$-alkynyl-$C_1$-$C_8$-alkyl; aryl-$C_1$-$C_4$-alkyl which is optionally substituted by up to 5 identical or different groups $R^b$; each of which is optionally substituted);

$R^1$ and $R^3$ or $R^3$ and $R^5$ or $R^5$ and $R^7$ can form together with the carbons to which they are attached an optionally substituted cyclopropyl, cyclobutyl, cyclopentyl, cyclohexyl;

$R^b$ represents fluorine, chlorine, bromine; $C_1$-$C_6$-alkyl; $C_1$-$C_4$-haloalkyl having 1 to 9 identical or different halogen atoms; $C_1$-$C_4$-alkoxy; $C_1$-$C_4$-haloalkoxy having 1 to 9 identical or different halogen atoms; $C_1$-$C_4$-alkylsulfanyl; $C_1$-$C_4$-haloalkylsulfanyl having 1 to 9 identical or different halogen atoms; $C_1$-$C_4$-alkylsulfonyl; $C_1$-$C_4$-haloalkylsulfonyl having 1 to 9 identical or different halogen atoms; $C_2$-$C_6$-alkenyl; $C_2$-$C_6$-alkynyl; $C_3$-$C_6$-cycloalkyl; phenyl; tri($C_1$-$C_4$)alkylsilyl; tri($C_1$-$C_4$)alkylsilyl-$C_1$-$C_4$-alkyl.

4. Process for preparing a compound of formula (I) according to claim 1, comprising in a Process (a) reacting one or more carbonyl halides or acids of formula (II)

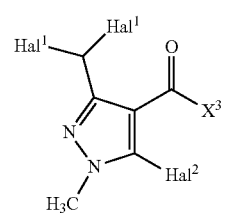

(II)

in which $X^3$ represents halogen or hydroxyl,
with one or more amines of formula (III-a)

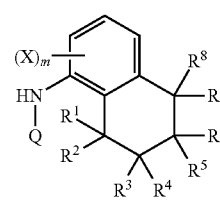

(III-a)

optionally in the presence of a coupling agent, optionally in the presence of an acid binder and optionally in the presence of a diluent to obtain a compound of formula (I-a),

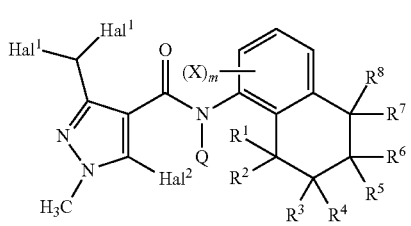
(I-a)

which is optionally reacted with a thionating agent and optionally in the presence of a catalytic or stoichiometric or more quantity of a base to obtain a compound of formula (I-b)

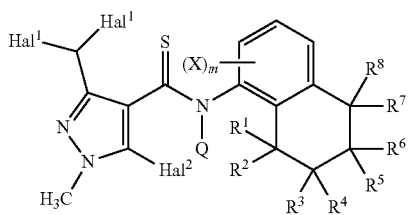
(I-b)

5. Method for controlling phytopathogenic harmful fungi, comprising applying a compound of formula (I) according to claim 1 to the phytopathogenic harmful fungi and/or a habitat thereof.

6. Composition for controlling phytopathogenic harmful fungi, comprising a content of at least one compound of formula (I) according to claim 1, in addition to one or more extenders and/or surfactants.

7. A Composition according to claim 6 comprising at least one further active ingredient selected from the group consisting of insecticides, attractants, sterilants, bactericides, acaricides, nematicides, fungicides, growth regulators, herbicides, fertilizers, safeners and semiochemicals.

8. A compound of formula (I) according to claim 1 capable of being used for control of phytopathogenic harmful fungi.

9. A Process for producing a composition for controlling phytopathogenic harmful fungi, comprising mixing a compound of formula (I) according to claim 1 with one or more extenders and/or surfactants.

10. A method according to claim 5 comprising treatment of one or more transgenic plants.

11. A method compound of formula (I) according to claim 5 comprising treatment of seed or seed of one or more transgenic plants.

12. Process for preparing a compound of formula (I) according to claim 4, comprising in a Process (a) reacting one or more carbonyl halides or acids of formula (II)

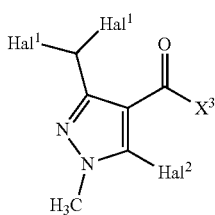
(II)

in which $X^3$ represents halogen or hydroxyl, with one or more amines of formula (III-a)

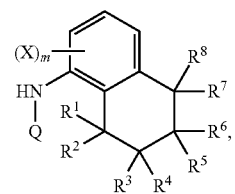
(III-a)

in the presence of a coupling agent, in the presence of an acid binder and in the presence of a diluent to obtain a compound of formula (I-a),

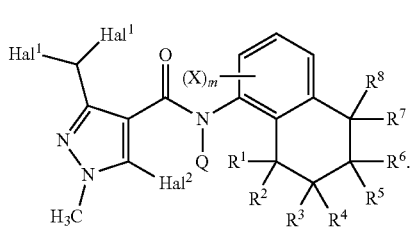
(I-a)

which is optionally reacted with a thionating agent and in the presence of a catalytic or stoichiometric or more quantity of a base to obtain a compound of formula (I-b)

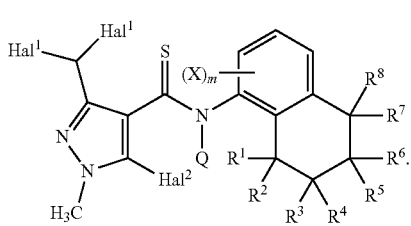
(I-b)

13. A compound according to claim 1, wherein m is 1, 2, or 3.

14. A compound according to claim 1, wherein Q is $C_1$-$C_6$-alkylsulfonyl, $C_1$-$C_4$-alkoxy-$C_1$-$C_4$-alkyl, $C_1$-$C_4$-haloalkylsulfonyl, or halo-$C_1$-$C_4$-alkoxy-$C_1$-$C_4$-alkyl.

15. A compound according to claim 1, wherein Hal1 is fluorine, T is oxygen, m is zero, and Q is hydrogen.

16. A compound according to claim 1, wherein $R^1$, $R^2$, $R^3$, $R^4$, $R^5$, $R^6$, $R^7$ and $R^8$ independently of one another represent hydrogen or methyl.

17. A compound according to claim 1, wherein T is sulfur.

* * * * *